United States Patent
Marchi et al.

(10) Patent No.: US 11,028,086 B2
(45) Date of Patent: Jun. 8, 2021

(54) PYRIDO-IMIDAZO RIFAMYCINS

(71) Applicant: Biofer S.p.A., Medolla (IT)

(72) Inventors: Egidio Marchi, Casalecchio di Reno (IT); Alessandro Lapini Sacchetti, Forte dei Marmi (IT); Claudia Ori, Castelvetro di Modena (IT); Lisa Preti, Carpi (IT)

(73) Assignee: BIOFER S.P.A., Medolla (IT)

( * ) Notice: Subject to any disclaimer, the term of this patent is extended or adjusted under 35 U.S.C. 154(b) by 0 days.

(21) Appl. No.: 16/718,634

(22) Filed: Dec. 18, 2019

(65) Prior Publication Data

US 2020/0157104 A1     May 21, 2020

Related U.S. Application Data

(63) Continuation-in-part of application No. PCT/IB2018/054645, filed on Jun. 25, 2018.

(30) Foreign Application Priority Data

Jun. 26, 2017    (EP) ..................................... 17177894
Aug. 8, 2017    (IT) ......................... 102017000091912

(51) Int. Cl.
    *C07D 471/22*     (2006.01)
    *A61P 31/04*     (2006.01)

(52) U.S. Cl.
    CPC ............ *C07D 471/22* (2013.01); *A61P 31/04* (2018.01)

(58) Field of Classification Search
None
See application file for complete search history.

(56) References Cited

U.S. PATENT DOCUMENTS

| | | |
|---|---|---|
| 4,179,438 A | 12/1979 | Marchi et al. |
| 4,341,785 A | 7/1982 | Marchi et al. |
| 7,045,620 B2 | 5/2006 | Viscomi et al. |

FOREIGN PATENT DOCUMENTS

| | | |
|---|---|---|
| WO | 2006/094662 | 9/2006 |
| WO | 2010/122436 | 10/2010 |
| WO | 2014/026254 | 2/2014 |
| WO | 2019/003076 | 1/2019 |

OTHER PUBLICATIONS

International Preliminary Report on Patentability dated May 28, 2019 in International (PCT) Application No. PCT/IB2018/054645.
Marchi et al., "4-Deoxypyrido[1',2':1,2]imidazo[5,4-c]rifamycin SV Derivatives. A New Series of Semisynthetic Rifamycins with High Antibacterial Activity and Low Gastroenteric Absorption", J. Med. Chem., 1985, vol. 28, 960-963.
Darkoh et al., "Bile Acids Improve the Antimicrobial Effect of Rifaximin", Antimicrobial Agents and Chemotherapy, Sep. 2010, vol. 54, No. 9, pp. 3618-3624.
Zullo et al., "Rifaximin therapy and hepatic encephalopathy: Pros and cons", World J Gastrointest Pharmacol Ther., Aug. 6, 2012, vol. 3, No. 4, pp. 62-67.
Cheng et al., "Chronic Exposure to Rifaximin Causes Hepatic Steatosis in Pregnane X Receptor-Humanized Mice", Toxicological Sciences, Jul. 2012, vol. 129, No. 2, pp. 456-468.
Bajaj et al., "Drug Therapy: Rifaximin", Diagnostic and Therapeutic Advances in Hepatology, Hepatology, vol. 52, No. 4, 2010, pp. 1484-1488.
Manguso et al., "Prevalence of H. Pylori Infection in Patients With Peptic Ulcer Disease Complicated by Hemorrhage After Assumption of Nonsteroidal Anti-Inflammatory Drugs: The Emofans Study", Abstracts/Digestive and Liver Disease, vol. 42S, 2010, S61-S192.
Cellai et al., "A Study of Structure-Activity Relationships in 4-Deoxypyrido(1',2'-1,2] imidazo[5,4-c]rifamycin SV Derivatives by Electron Spectroscopy for Chemical Analysis and $^1$H NMR", Molecular Pharmacology, vol. 27, pp. 103-108.
Bellomo et al., "Synthesis and Antibacterial Activity of Some Esters, Amides, and Hydrazides of 3-Carboxyrifamycin S. Relationship between Structure and Activity of Ansamycins", J. Med. Chem., 1981, vol. 24, pp. 1310-1314.
Dampier et al., "Electronegative Groups at C-3 of Rifamycin S Enhance Its Activity toward DNA-Dependent RNA Polymerase", Journal of the American Chemical Society, vol. 97, No. 21, Oct. 15, 1975, pp. 6254-6256.
Stahl et al., "Ch. 5, Biological Effects of the Drug Salt Form", Handbook of Pharmaceutical Salts Properties, Selection, and Use, Pharmaceutical Salts, 2008, pp. 125-133.

*Primary Examiner* — Samantha L Shterengarts
(74) *Attorney, Agent, or Firm* — Wenderoth, Lind & Ponack, L.L.P.

(57) ABSTRACT

The present invention relates to novel pyrido-imidazo rifamycins, characterized by a highly selective antibacterial activity and low absorption by oral route.

28 Claims, 40 Drawing Sheets

Example 1
¹H NMR Spectrum, CDCl₃

Example 1
$^{13}$C NMR Spectrum, CDCl$_3$

Example 2
4'-formyl-4-desoxypyrido[1',2'-1,2]imidazo[5,4-c]rifamycin S
1H NMR Spectrum, CDCl3

Example 2
4'-formyl-4-desoxypyrido[1',2'-1,2]imidazo[5,4-c]rifamycin S
13C NMR Spectrum, CDCl3

Example 2
4'-formyl-4-desoxypyrido[1',2'-1,2]imidazo[5,4-c]rifamycin SV
¹H NMR Spectrum, CDCl₃

Example 2
4'-formyl-4-desoxypyrido[1',2'-1,2]imidazo[5,4-c]rifamycin SV
$^{13}$C NMR Spectrum, CDCl$_3$ Example 3
1H NMR Spectrum, CDCl3

Example 3
$^{13}$C NMR Spectrum, CDCl$_3$

Example 4
¹H NMR Spectrum, CDCl₃

Example 4
$^{13}$C NMR Spectrum, CDCl$_3$

Example 5
$^1$H NMR Spectrum, $CDCl_3$

Example 5
13C NMR Spectrum, CDCl3

Example 6
¹H NMR Spectrum, MeOD

Example 6
$^{13}C$ NMR Spectrum, MeOD

Example 7
$^1$H NMR Spectrum, CDCl$_3$

Example 7
$^{13}$C NMR Spectrum, CDCl$_3$

Example 8
¹H NMR Spectrum, CDCl₃

Example 8
$^{13}C$ NMR Spectrum, $CDCl_3$

Example 9
$^1$H NMR Spectrum, CDCl$_3$

Example 9
$^{13}$C NMR Spectrum, CDCl$_3$

Example 10
$^1$H NMR Spectrum, $CDCl_3$

Example 10
$^{13}$C NMR Spectrum, $CDCl_3$

Example 11
1H NMR Spectrum, MeOD

Example 11
13C NMR Spectrum, MeOD

Example 12
1H NMR Spectrum, MeOD

Example 12
$^{13}$C NMR Spectrum, MeOD

PYRIDO-IMIDAZO RIFAMYCINS

The present invention relates to new pyrido-imidazo rifamycins, characterized by a highly selective antibacterial activity and low absorption by oral route.

STATE OF THE ART

Pyrido(1',2':1,2)imidazo(5,4-c)rifamycins are antibiotics obtained by synthesis starting from rifamycin S or rifamycin O, characterized, on the one hand, by a low oral absorption and, on the other hand, by a good antibacterial activity against both Gram-positive and Gram-negative bacteria. The progenitor of this class of antibiotics is Rifaximin, which was synthesized by Marchi et al. at the end of the seventies (U.S. Pat. No. 4,341,785A).

Currently, this antibiotic is on the European and American market, where it has been particularly successful for the treatment of many diseases of the gastrointestinal tract in humans, such as Crohn's disease, diverticulosis, irritable bowel, porto-systemic ammoniemia, etc., and especially in the USA in the prevention of traveler's diarrhea.

The antibiotic is also on the veterinary market for bacterial diseases of the genital apparatus and mastitis diseases in cows.

Since 1988, the year in which Rifaximin was placed on the Italian market, the study of this antibiotic has continued both from a biological point of view and from a chemical point of view. On the one hand, there are many formulation technology patents and, on the other hand, patents claiming polymorphs or pseudopolymorphs, also called solvates, which are given fundamental importance because a different solubility is linked to polymorphs and solvates, to which a different bioavailability and toxicity seem to correspond: in the U.S. Pat. No. 7,045,620 and WO2006094662 patents, the polymorphic forms $\alpha$, $\beta$, $\gamma$, $\varepsilon$ and $\delta$ are claimed, respectively. It is very difficult to establish whether the various claimed products are indeed polymorphic on the basis of the partial X-ray refractometric measurements on the crystalline powders. In fact, data such as the melting point of the compounds, which could highlight the differences between polymorphic forms and possibly derivatives in a solvated form, are not provided. These polymorphic forms seem to possess a different solubility, to which a different bioavailability and toxicity seem to be related (WO2006094662). All this appears very confused and, if we want, contradictory. In fact, to perform its activity, the antibiotic must be dissolved in the medium, in this case in the intestinal fluid, so if it were more soluble it should be more active and, therefore, lower doses should be sufficient. Furthermore, the presence of bile acids (Bile acids improve the antimicrobial effect of Rifaximin. Darkoh., et Al., Antimicrob. Agents Chemother.: 2010; 54 (9), 3618-3624) increases the activity of the product just because it increases the amount of dissolved antibiotic. In this case, however, bile acids increase the bioavailability of all the polymorphic forms and, therefore, also the possible toxicity of the form used in therapy, if the absorption were related to the amount of dissolved drug. Furthermore, in an aqueous environment, it is difficult to understand which is the stable polymorphic form, since the various forms described, $\alpha$, $\beta$, $\gamma$, $\varepsilon$ and $\delta$, can be transformed into one another by absorption of moisture, even in the solid state (WO2006094662). As it can be seen, one of Rifaximin crucial points is indeed related to its bioavailability (Rifaximin therapy and hepatic encephalopathy: pros and cons. Zullo A., et Al., Word Gastrointest. Pharmacol. Ther.: 2012; 3(4):62-67; Chronic Exposure to Rifaximin Causes Hepatic Steatosis in Pregnane X Receptor-Humanized Mice. Jie Cheng, Kristopher W. Krausz, Naoki Tanaka, and Frank, J. Gonzalez, Toxicol. Sciences:2012; 129(2), 456-468), which should be limited by its insolubility, but which is instead dependent either on the pseudopolymorphic or solvated forms used, or the presence of bile acids in the intestinal fluid, and the intestinal inflammatory state, as described in the work cited on porto-systemic encephalopathy.

Of further interest is the activity that the antibiotic has on the eukaryotic bacterial flora, e.g. on the macrobiota. Rifaximin has an assessable activity on the bacterial species that constitute intestinal eukaryotic flora in humans. For example, Rifaximin has a noticeable antibacterial activity on Lactobacilli, Bifidobacteria, Enterococci, Enterobacteria, etc., strains, even if not all species are inhibited in the same way.

Clearly, being able to have an antibiotic that was devoid or, in any case, had a high selectivity for the bacterial species in the intestinal macrobiota would be a further important innovation that, combined with a low oral bioavailability, would represent a fundamental therapeutic improvement for the product. In fact, today the therapeutic use of Rifaximin as of all other antibiotics, whether topical or not, is associated with supplementation with eukaryotic strain supplements, since the use of antibiotics on the one hand eliminates and/or reduces the intestinal presence of pathogenic strains, but at the same time results in a significant decrease and alteration of the eukaryotic strains mix that form the macrobiota. Therefore, to have an antibiotic showing a good selectivity towards eukaryotic strains that reduces, for example, the intestinal presence of the species by a single factor of 10, or at most 100, could be considered a fundamental therapeutic innovation, considering that the use of these antibiotics is mostly chronic, except for the occasional use for traveler's diarrhea.

Precisely to highlight the importance of a selectivity towards eukaryotic strains, it is recalled that an important characteristic of this class of antibiotics is the possibility to repeat the therapy three or four weeks after the previous treatment, since the selection of resistant strains is greatly hampered by the particular mechanism of action of rifamycins. These, in fact, are active on the DNA-dependent bacterial RNA polymerase, so that the strains that can be selected as resistant during treatment are, in fact, easily controlled by non-resistant strains, since they have a limited replication capacity. In addition, unlike what happens for other antibiotics, such as penicillins, etc., resistance to rifamycins is not transmissible through plasmids. Obviously, these characteristics, together with the fact that pyrido-imidazorifamycins, such as Rifaximin, are poorly absorbed by oral route, make this class of antibiotics particularly important for gastroenteric tract diseases, which are often chronic diseases. It is therefore very clear the importance to have an antibiotic which is active on the pathogenic strains possibly involved in intestinal colonization, has a good selectivity towards the eukaryotic strains that form the microbiota and, just as important, shows a very low absorption.

Taking up what already described above, Rifaximin shows a variable absorption, depending also on the used solvate, which can range from 0.5% to more than 1%, with a renal excretion of about 0.36% (Bajaj J. S., Riggio O., Drug therapy: rifaximin. Hepatology 2010; 52: 1484-148). This absorption is related to the solubility of the solvate itself, so that the forms with the lowest water content are the most absorbed. The amorphous form is also very soluble, and it is thus shown to be absorbed 5-6 times more than Rifaximin α in the healthy volunteer (Marzo A., Ismaili S., Dig. Liv. Dis. 2010; 42(s2):s191-s192), and it is therefore considered at risk for possible selection of resistant bacteria to a systemic level. It is apparent that this risk, linked to solubility/absorption, is certainly present also for Rifaximin α, since it has been demonstrated (Darkoh C., Lichtenberger L. M., Ajami N., et al. Antimicrob. Agents Chemother. 2010; 54:3618-24) that Rifaximin, in the presence of bile acids, goes from a solubility of 0.6% in water to a solubility of 72.6%, i.e. more than one hundred times greater, in the presence of as low as 20 mM bile acids. Since Rifaximin is administered in high doses, ranging from a minimum of 400 mg/day in traveler's diarrhea, to 800 mg/day in diverticulitis, to 2400 mg/day in porto-systemic ammoniemia, even without considering solubility in the presence of bile acids, it is clear that even a limited absorption, such as that of Rifaximin, could represent a problem both for the potential for selection of resistant bacterial strains to a systemic level, including also the mycobacterium of tuberculosis, and for the possible interaction with drugs, such as statins, which share common enzymatic mediators, at the liver level. For example, an increase in sodium and potassium concentrations in blood was reported for Rifaximin during therapeutic treatment for porto-systemic ammoniemia. In addition, Rifaximin has an appreciable activity, as illustrated above, also on the bacterial strains constituting the intestinal macrobiota, therefore it is necessary to intervene with a supplementation of eukaryotic bacterial strains in order to restore the intestinal probiotic complex after each period of administration of the antibiotic.

In addition, having Rifaximin an agonist activity on the hepatic PXR receptor, from which its anti-inflammatory intestinal action derives, it has been highlighted how Rifaximin, although not very absorbed, provokes a massive steatosis in mice with such humanized receptor. (Cheng, Kristopher W. Krausz, Naoki Tanaka, and Frank, J. Gonzalez, Toxicological Sciences, 129(2), 456-468 (2012)).

In the light of these results, the need is therefore felt for new rifamycin derivatives with a pyrido-imidazo structure characterized by a highly selective antibacterial activity and low absorption by the oral route, for example 50% less than Rifaximin.

GENERAL DESCRIPTION OF THE INVENTION

The products active as antibiotics in the field of rifamycins must comply with conformational and chemical requirements and must possess an appropriate balance between lipophilia and hydrophilia (L. Cellai, S. Cerrini, A. Segre, C. Battistoni, G. Cossu, G. Mattogno, M. Brufani and E. Marchi. Mol. Pharm. 1985, 27:103-108).

Therefore, in the present invention, to maintain the pyrido-imidazo structure on Rifamycin SV, an easily functionalizable group was introduced on the pyridine core, so that it was subsequently possible to obtain new derivatives with very different chemical and physical-chemical characteristics. In this way, the inventors have surprisingly found molecules with suitable characteristics, namely: an intestinal absorption of at least 50% lower than that of Rifaximin, a good antibacterial activity on the pathogenic strains, and a negligible activity on the bacterial strains constituting the intestinal macrobiota, and in any case lower than that of Rifaximin. Among the various possible chemical structures, the inventors experimentally found that the introduction in the 4'- or 5'-position of the pyridine core of a formyl group, provides a 4'- or 5'-formyl-4-desoxy-pyrido [1',2'-1,2]imidazo[5,4-c]rifamycin SV derivative which is completely devoid of activity in itself, but time it is at the same susceptible to be easily transformed into an hydrazone, or oxime, or imine. The aldehyde group in the two positions 4'- or 5'-significantly increases the dissociation of the hydroxy group in position 8—that, being a strongly electron withdrawing group, results therefore devoid of antibacterial activity since its ability to cross the bacterial wall is hindered (P. Bellomo, E. Marchi, G. Mascellani, J. Med. Chem, 1981, 24 (11), 1310-1314; M. F. Dampier, H. W. Whitlock, Jr. J. Am. Chem. Soc. 1975, 97:21, 6254-6256). Surprisingly, however, its electronic contribution can be favorably modified, by transforming the carbonyl group into an hydrazone, oxime or imine. These derivatives, being characterized by a different inductive/mesomeric effect, generally positive, have surprisingly shown to have more modulable and suitable biological characteristics.

Since the reaction between Rifamycin O and 2-aminopyridine bearing a formyl group in position 4- or in position 5 is difficult, due to the reactivity of the formyl group, the inventors tried to use 2-amino-4-formylpyridine protected as acetal. The reaction is possible but, in any case, difficult, since obtaining the protected 2-amino-4-formylpyridine is not easy and leads to a particularly dirty reagent. The inventors, therefore, hypothesized to obtain the formyl group on the condensed pyridine core after having introduced a pyrido-imidazo group on the rifamycin SV which had a further functionalizable group. Surprisingly, after having obtained 4'-methylol-4-desoxypyrido[1',2'-1,2]imidazo[5,4-c]rifamycin SV in good yields, by reaction of Rifamycin O with 2-amino-4-methylol-pyridine, it was possible to obtain 4'-formyl-4-desoxypyrido[1',2'-1,2]imidazo[5,4-c]rifamycin SV, by oxidation of the methylol group with manganese dioxide in a suitable solvent, and subsequent reduction with ascorbic acid. The inventors were therefore able to verify that the product thus obtained is stable and further functionalizable into a hydrazone, oxime, or imine. Subsequently, the inventors were able to verify that, surprisingly, other ways to obtain hydrazones, oximes, or imines of 4'-formyl-4-desoxypyrido[1',2'-1,2]imidazo[5,4-c]rifamycin SV were possible, by reacting Rifamycin O or 3-iodo or 3-bromorifamicin S with a suitable derivative of 2-amino-4/5-formylpyridine. By using these synthetic routes, they were able to synthesize several hydrazones, among which those in 4'- and 5'-position, which were shown to have a good antibacterial activity. Among these products, in particular, 4'-[(4-methyl-1-piperazinyl)iminomethyl]-4-desoxypyrido[1',2'-1,2]imidazo[5,4-c]rifamycin SV (hereinafter Example 3) showed good antibacterial activity on Gram-positive and Gram-negative strains, and surprisingly showed an intestinal absorption 7-8 times lower, i.e. about 15%, compared to that shown and confirmed in the literature by Rifaximin. Furthermore, an even more striking characteristic of this derivative is represented by the high selectivity shown towards the tested eukaryotic strains, which are essential components of the intestinal macrobiota.

DEFINITIONS

Figure 1:
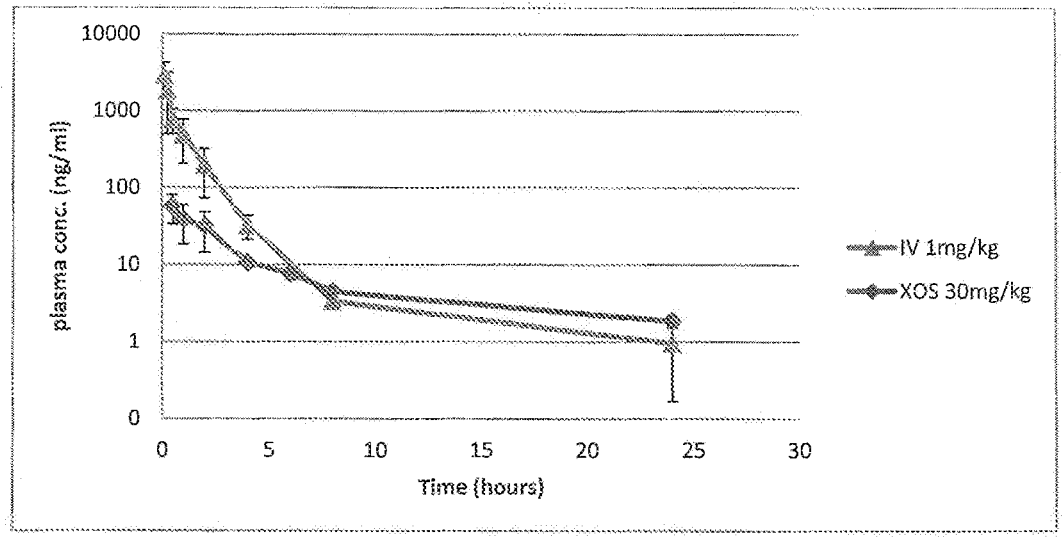
FIG. 1 shows a comparison of the blood levels of Rifaximin (RFX) after IV and oral administration.
Figure 2:
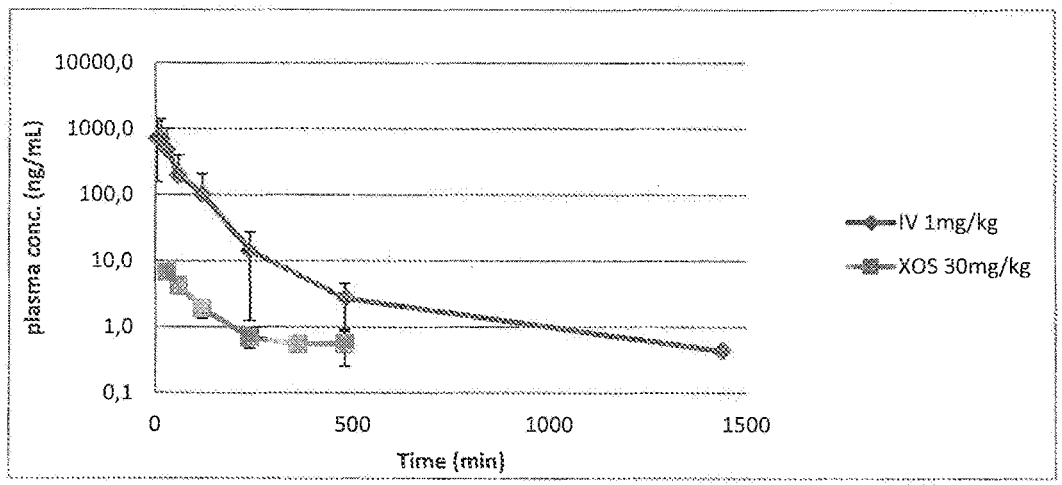
FIG. 2 shows a comparison of the blood levels of the compound of Example 3 after IV and oral administration.

Unless otherwise defined, all terms of the art, notations, and other scientific terms used herein are intended to have the meanings commonly understood by those skilled in the art to which this description belongs. In some cases, terms with meanings that are commonly understood are defined herein for clarity and/or ready reference; therefore, the inclusion of such definitions in the present description should not be interpreted as being representative of a substantial difference with respect to what is generally understood in the art.

The term "halogen" herein refers to fluorine (F), chlorine (Cl), bromine (Br), or iodine (I).

The term "$C_1$-$C_{10}$ alkyl" herein refers to a branched or linear hydrocarbon containing from 1 to 10 carbon atoms. Example of $C_1$-$C_{10}$ alkyl groups include, but are not limited to, methyl, ethyl, n-propyl, isopropyl, n-butyl, sec-butyl, isobutyl, tert-butyl, n-pentyl, n-hexyl.

The term "aryl" herein refers to aromatic mono- and polycarbocyclic ring systems, wherein the individual carbocyclic rings in the polycarbocyclic ring systems may be fused or attached to each other by a single bond. Suitable aryl groups comprise, but are not limited to, phenyl, naphthyl, and biphenyl.

The term "aryloxy" herein refers to an O-aryl group, wherein "aryl" is defined above.

The term "alcoxy" herein refers to an O-alkyl group, wherein "alkyl" is defined above.

The term "heterocycle" herein refers to a 4-, 5-, 6-, 7- or 8-membered monocyclic ring, which is saturated or unsaturated, and which is comprised of carbon atoms and one or more heteroatoms selected from N, O and S, and wherein the nitrogen and sulfur heteroatoms may optionally be oxidized, and the nitrogen heteroatom may be optionally quaternized. The heterocyclic ring may be attached to any heteroatom or carbon atom, provided that the attachment translates into the creation of a stable structure. The term comprises also any bicyclic systems wherein any of the above heterocyclic rings is fused to an aryl or to another heterocycle. When the heterocyclic ring is an aromatic heterocyclic ring, it may be defined as "heteroaromatic ring".

The term "unsaturated ring" herein refers to a ring that is partially or completely unsaturated. For example, an unsaturated C6 monocyclic ring refers to cyclohexene, cyclohexadiene, and benzene.

The term "substituted" herein refers to a mono- or poly-substitution with a defined (or not defined) substituent to the extent that such a single or multiple substitution is chemically allowed.

The term "physiologically acceptable excipient" refers to a substance devoid of any pharmacological effects of its own, and that does not produce adverse reactions when administered to a mammal, preferably a human being.

Physiologically acceptable excipients are well known in the art and are described, for example, in *Handbook of Pharmaceutical Excipients, sixth edition* 2009, incorporated herein by reference.

The term "pharmaceutically acceptable salts or derivatives" refers to those salts or derivatives which possess the biological effectiveness and properties of the salified compound, and that do not produce adverse reactions when administered to a mammal, preferably a human being. The pharmaceutically acceptable salts may be inorganic or organic salts; examples of pharmaceutically acceptable salts include, but are not limited to: carbonate, hydrochloride, hydrobromide, sulfate, hydrogen sulfate, citrate, maleate, fumarate, trifluoroacetate, 2-naphthalenesulfonate, and para-toluenesulfonate. Additional information on pharmaceutically acceptable salts may be found in *Handbook of pharmaceutical salts*, P. Stahl, C. Wermuth, WILEY-VCH, 127-133, 2008, incorporated herein by reference.

The terms "comprising", "having", "including" and "containing" are to be construed as open-ended terms (i.e., meaning "comprising, but not limited to"), and are to be considered as a support also for terms such as "consist essentially of", "consisting essentially of", or "consisting of".

The terms "consists essentially of", "consisting essentially of" are to be construed as semi-closed terms, meaning that no other ingredients which materially affects the novel characteristics of the invention are included.

The terms "consists of", "consisting of" are to be construed as closed terms.

DETAILED DESCRIPTION OF THE INVENTION

The inventors have experimentally found that hydrazones of Rifamicin SV with a pyrido-imidazo structure show a highly selective antibacterial activity and are poorly absorbed by oral route.

According to a first aspect, the present invention relates to compounds of Formula (I) or pharmaceutical acceptable salts thereof

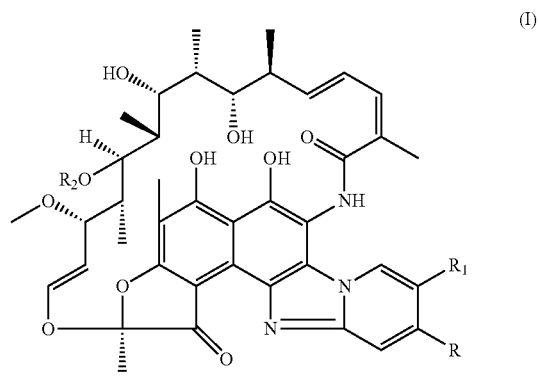

(I)

wherein

R and $R_1$ may be H,

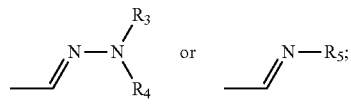

with the proviso that:
when

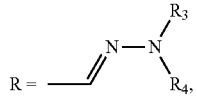

then $R_1$=H and $R_2$=CH$_3$CO— or H;
when

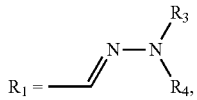

then R=H and $R_2$=CH$_3$CO— or H;
when

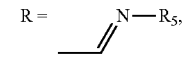

then $R_1$=H and $R_2$=CH$_3$CO— or H;
and when

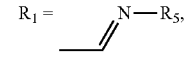

then R=H and $R_2$=CH$_3$CO— or H;
wherein $R_3$ and $R_4$ are the same or different and selected from the group comprising hydrogen, linear or branched $C_1$-$C_{10}$ alkyl optionally substituted with one or more substituents selected from aminoalkyl, alkoxy, phenoxy or sulfo, and aryl optionally mono- or disubstituted with $C_1$-$C_4$ alkyl or alkoxy groups, halogen, amino, nitro; or
$R_3$ and $R_4$ taken together with two consecutive carbon atoms of the pyridine core may form a phenyl ring, optionally substituted with $C_1$-$C_4$ alkyl, or a 5- or 6-membered heterocyclic ring, optionally substituted with $C_1$-$C_4$ alkyl,
$R_5$ is selected from the group comprising hydrogen, hydroxy, linear or branched $C_1$-$C_{10}$ alkyl optionally substituted with one or more substituents selected from aminoalkyl, alkoxy, phenoxy or sulfo, and aryl optionally mono- or disubstituted with $C_1$-$C_4$ alkyl or alkoxy groups, halogen, amino, nitro.

A class of preferred compounds comprise compounds of Formula (I)
wherein R and $R_1$ may be H or

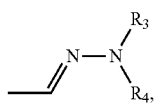

wherein the aryl, optionally mono- or disubstituted with $C_1$-$C_4$ alkyl or alkoxy groups, halogen, amino, nitro, is selected from phenyl and benzyl.

A further class of more preferred compounds comprise compounds of Formula (I) wherein R and $R_1$ may be H or

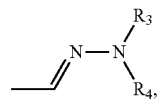

wherein the 5- or 6-membered heterocyclic ring is selected from the group comprising pyrrolidine, piperidine, piperazine, and morpholine.

The following compounds of Formula (I), or pharmaceutically acceptable salts thereof, are particularly preferred:
4'-[(4-methyl-1-piperazinyl)iminomethyl]-4-desoxypyrido[1',2'-1,2]imidazo[5,4-c]rifamycin SV (Example 3);
4'-[(1-piperidinyl)iminomethyl]-4-desoxypyrido[1',2'-1,2]imidazo[5,4-c]rifamycin SV (Example 4);
4'-[(N, N-dimethylamino)iminomethyl]-4-desoxypyrido[1',2'-1,2]imidazo[5,4-c]rifamycin SV (Example 5);
4'-[(4-carboxyamidopyridyl)iminomethyl]-4-desoxypyrido[1',2'-1,2]imidazo[5,4-c]rifamycin SV (Example 6);
5'-[(N, N-dimethylamino)iminomethyl]-4-desoxypyrido[1',2'-1,2]imidazo[5,4-c]rifamycin SV (Example 7);
5'-[(1-piperidinyl)iminomethyl]-4-desoxypyrido[1',2'-1,2]imidazo[5,4-c]rifamycin SV (Example 8);
5'-[(N, N-dimethylamino)iminomethyl]-4-desoxypyrido[1',2'-1,2]imidazo[5,4-c]rifamycin SV (Example 9);
4'-[(-4-methyl-1-piperazinyl)iminomethyl]-4-desoxypyrido[1',2'-1,2]imidazo[5,4-c]rifamycin S (Example 10);
25-desacetyl-5'-[(1-piperidinyl)iminomethyl]-4-desoxypyrido[1',2'-1,2]imidazo[5,4-c]rifamycin SV (Example 11);
25-desacetyl-5'-[(N, N-dimethylamino)iminomethyl]-4-desoxypyrido[1',2'-1,2]imidazo[5,4-c]rifamycin SV (Example 12);
4'-[(N-morpholinyl)iminomethyl]-4-desoxypyrido[1',2'-1,2]imidazo[5,4-c]rifamycin SV;
5'-[(N-morpholinyl)iminomethyl]-4-desoxypyrido[1',2'-1,2]imidazo[5,4-c]rifamycin SV;
25-desacetyl-4'-[(N-morpholinyl)iminomethyl]-4-desoxypyrido[1',2'-1,2]imidazo[5,4-c]rifamycin SV;
25-desacetyl-5'-[(N-morpholinyl)iminomethyl]-4-desoxypyrido[1',2'-1,2]imidazo[5,4-c]rifamycin SV;
4'-[(N-propyl, N-butyl)iminomethyl]-4-desoxypyrido[1',2'-1,2]imidazo[5,4-c]rifamycin SV;
5'-[(N-propyl, N-butyl)iminomethyl]-4-desoxypyrido[1',2'-1,2]imidazo[5,4-c]rifamycin SV;
25-desacetyl-4'-[(N-propyl, N-butyl)iminomethyl]-4-desoxypyrido[1',2'-1,2]imidazo[5,4-c]rifamycin SV;
25-desacetyl-5'-[(N-propyl, N-butyl)iminomethyl]-4-desoxypyrido[1',2'-1,2]imidazo[5,4-c]rifamycin SV;
4'-[(N, N-dipentyl)iminomethyl]-4-desoxypyrido[1',2'-1,2]imidazo[5,4-c]rifamycin SV;
5'-[(N, N-dipentyl)iminomethyl]-4-desoxypyrido[1',2'-1,2]imidazo[5,4-c]rifamycin SV;
25-desacetyl-4'-[(N, N-dipentyl)iminomethyl]-4-desoxypyrido[1',2'-1,2]imidazo[5,4-c]rifamycin SV;
25-desacetyl-5'-[(N, N-dipentyl)iminomethyl]-4-desoxypyrido[1',2'-1,2]imidazo[5,4-c]rifamycin SV;
4'-[(4-ethyl-1-piperazinyl)iminomethyl]-4-desoxypyrido[1',2'-1,2]imidazo[5,4-c]rifamycin SV;
5'-[(4-ethyl-1-piperazinyl)iminomethyl]-4-desoxypyrido[1',2'-1,2]imidazo[5,4-c]rifamycin SV;
25-desacetyl-4'-[(4-ethyl-1-piperazinyl)iminomethyl]-4-desoxypyrido[1',2'-1,2]imidazo[5,4-c]rifamycin SV;
25-desacetyl-5'-[(4-ethyl-1-piperazinyl)iminomethyl]-4-desoxypyrido[1',2'-1,2]imidazo[5,4-c]rifamycin SV;

4'-[(4-propyl-1-piperazinyl)iminomethyl]-4-desoxypyrido[1',2'-1,2]imidazo[5,4-c]rifamycin SV;

5'-[(4-propyl-1-piperazinyl)iminomethyl]-4-desoxypyrido[1',2'-1,2]imidazo[5,4-c]rifamycin SV;

25-desacetyl-4'-[(4-propyl-1-piperazinyl)iminomethyl]-4-desoxypyrido[1',2'-1,2]imidazo[5,4-c]rifamycin SV; and 25-desacetyl-5'-[(4-propyl-1-piperazinyl)iminomethyl]-4-desoxypyrido[1',2'-1,2]imidazo[5,4-c]rifamycin SV.

According to a second aspect, the present invention relates to a first process for producing a compound of Formula (I), comprising the steps of:

reacting Rifamycin O with 2-amino-4-hydroxymethylpyridine to obtain 4'-hydroxymethyl-4-desoxypyrido[1',2'-1,2]imidazo[5,4-c]rifamycin S or SV;

oxidizing in liquid phase, preferably in an aprotic solvent, 4'-hydroxymethyl-4-desoxypyrido[1',2'-1,2]imidazo[5,4-c]rifamycin S or SV with a suitable oxidant, preferably manganese dioxide, to obtain 4'-formyl-4-desoxypyrido[1',2'-1,2]imidazo[5,4-c]rifamycin S or SV;

reacting 4'-formyl-4-desoxypyrido[1',2'-1,2]imidazo[5,4-c]rifamycin S or SV with an hydrazine of Formula (II) $NH_2—N(R_3)(R_4)$, wherein $R_3$ and $R_4$ are as defined in Formula (I), to obtain the corresponding hydrazone.

In a preferred embodiment of the first process according to the invention, from about 1 to about 6 molar equivalents of 2-amino-4-hydroxymethylpyridine are used per mole of Rifamycin O and/or from about 1 to about 6 molar equivalents of hydrazine are used per mole of 4'-formyl-4-desoxypyrido[1',2'-1,2]imidazo[5,4-c]rifamycin S or SV.

According to a third aspect, the present invention relates to a second process for producing a compound of Formula (I), comprising the steps of:

reacting an hydrazine of Formula (II) $NH_2—N(R_3)(R_4)$, wherein $R_3$ and $R_4$ are as defined in Formula (I), with 2-amino-4-formylpyridine or with 2-amino-5-formylpyridine to obtain the corresponding hydrazone;

reacting the obtained hydrazone with Rifamycin O, 3-iodorifamycin S, 3-bromorifamycin S or 25-desacetyl-25-hydroxyrifamycin S.

In preferred embodiment of the second process according to the invention, from about 1 to about 6 molar equivalents of the obtained hydrazone are used per mole of Rifamycin O or 3-iodo/bromo rifamycin S.

Preferably, in the processes according to the invention, the solvent used is an organic solvent selected from an aliphatic alkanol containing 1 to 4 carbon atoms, alone or in a mixture with water, or with DMF, or in a short-chain halogenated solvent, preferably dichloromethane.

Preferably, in the processes according to the invention, the reaction temperature may vary from the temperature of 10° C. to the solvent boiling point, preferably not above 80° C., and/or the reaction time may vary from a few minutes to 24 h.

According to a preferred embodiment, the compounds of Formula (I) can be oxidized by treatment with a suitable oxidant, preferably manganese dioxide.

According to a fourth aspect, the present invention relates to the product 4'-hydroxymethyl-4-desoxypyrido[1',2'-1,2]imidazo[5,4-c]rifamycin S or SV, usable as an intermediate for obtaining 4'-formyl-4-desoxypyrido[1',2'-1,2]imidazo[5,4-c]rifamycin S or SV.

The product is preferably obtained by reaction of 1 mole of Rifamycin O with 1 to 5 moles of 2-amino-4-hydroxymethylpyridine.

According to a fifth aspect, the present invention relates to the product 4'-formyl-4-desoxypyrido[1',2'-1,2]imidazo[5,4-c]rifamycin S or SV, as an intermediate for obtaining compounds of Formula (I).

The product is preferably obtained starting from the product 4'-hydroxymethyl-4-desoxypyrido[1',2'-1,2]imidazo[5,4-c]rifamycin S or SV by oxidation in liquid phase with, e.g., manganese dioxide.

According to a sixth aspect, the present invention relates to compounds of Formula (I) for use as a medicament.

In a preferred embodiment, the compounds of Formula (I) are used in the treatment and/or prevention of gastrointestinal tract diseases, preferably selected from the group comprising diseases due to bacterial dismicrobism, IBD, Crohn's disease, diverticulosis, and traveler's diarrhea, or in skin, eye, vaginal or dental infections, preferably in the treatment of diseases requiring a chronic treatment.

In a further preferred embodiment, the compounds of Formula (I) are used in the treatment and/or prevention of dry mastitis, in vaginal diseases in cows, in intestinal diseases in pets, or as auxinic therapy in animal husbandry, preferably for chickens, turkeys, ducks or rabbits.

According to a seventh aspect, the present invention relates to a pharmaceutical composition comprising at least one compound of Formula (I), together with at least one pharmaceutically acceptable excipient.

Preferably, the above formulation is suitable to be administered topically, preferably in the form of immediate release or programmed release solids, or liquids or gels.

General Synthetic Scheme

The compounds described in the present invention may be prepared using the following methods.

1° Method

A first method consists in reacting Rifamycin O in a protic solvent, such as methyl, ethyl, propyl alcohol, etc., alone or in a mixture with other solvents, such as acetonitrile, dioxane, etc., with 2-amino-4-methylolpyridine to obtain 4'-methylol-pyrido[1',2'-1,2]imidazo(5,4-c)rifamycin SV. This compound is oxidized to the corresponding carbonyl derivative 4'-formylpyrido[1',2'-1,2]imidazo(5,4-c)rifamycin S with manganese dioxide in an aprotic solvent, such as acetonitrile or dichloromethane, and subsequently reduced with con ascorbic acid to the SV form, and then reacted with a suitable hydrazine, hydroxylamine, or amine according to Scheme 1:

Scheme 1

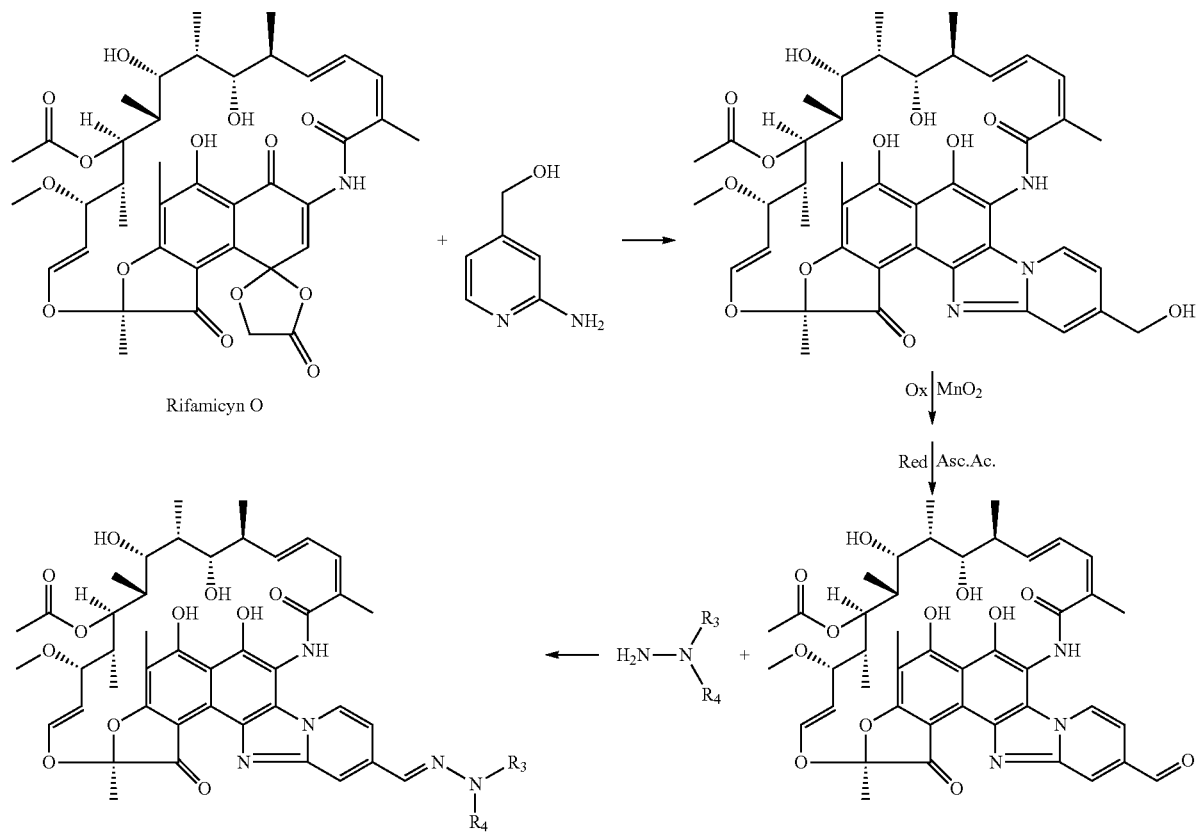

Wherein $R_3$ and $R_4$ have the same meaning reported in Formula (I).

With this method, it is also possible to obtain imines and oximes, using suitable reagents.

With Scheme 1, it is also possible to obtain 5' derivatives starting, for example, from (2-amino-5-pyridin)methanol.

2° Method

A second method consists in reacting 2-amino-4/5-carbonylpyridine with the appropriate amine, hydrazine, or hydroxylamine obtaining the addition product which is subsequently reacted with 3-iodo/bromorifamycin S (obtained according to the U.S. Pat. No. 4,179,438 patent) or with Rifamycin O according to Scheme 2:

Scheme 2

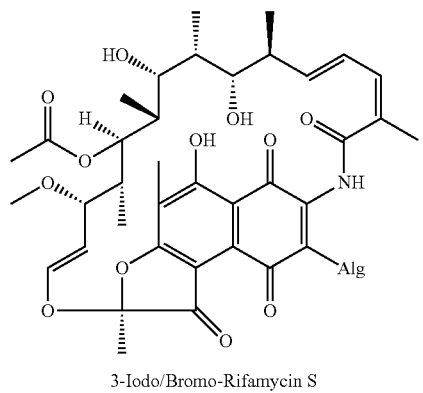

3-Iodo/Bromo-Rifamycin S

-continued
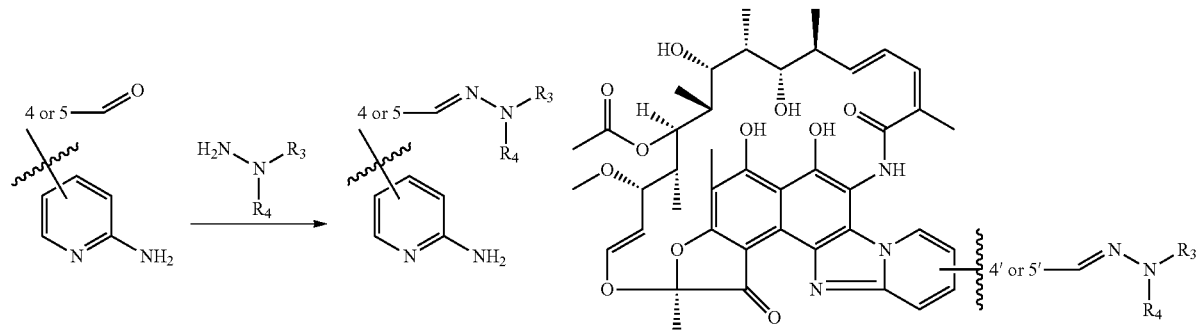
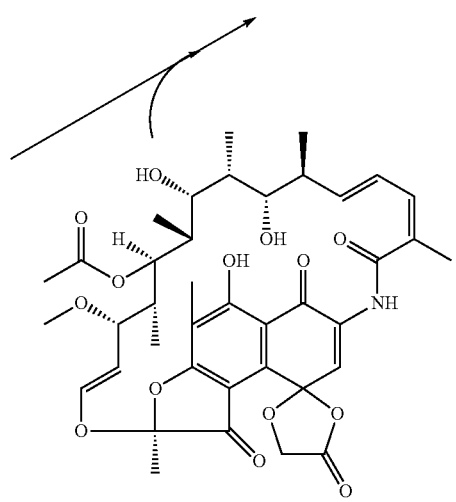
Rifamycin O

Wherein R₃ and R₄ have the same meaning seen for Scheme 1.

Using this synthesis scheme, starting from 3-iodo/bromorifamycin S or from Rifamycin O and a hydrazone of 2-amino-4/5-formylpyridine, the hydrazone derivatives of 4'/5'-formyl-4-desoxy-pyrido[1',2'-1,2]imidazo[5,4-c]rifamycin SV were obtained.

In particular, from about 1 to about 6 moles of an hydrazone, obtained by condensation of 2-amino-4-formylpyridine or 2-amino-5-formylpyridine with a suitable substituted hydrazine wherein the substituents R₃ and R₄ are as defined above, are used per mole of Rifamycin O or 3-iodo/bromo rifamycin S.

The final products obtained are all in the reduced form, i.e. in the SV form; it is however possible to obtain also derivatives in the S form, i.e. in the oxidized form, using a suitable oxidizing agent, usually with manganese dioxide which is easily eliminated by filtration (see Scheme 3).

Scheme 3

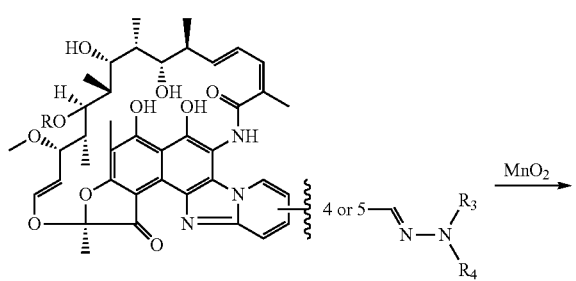

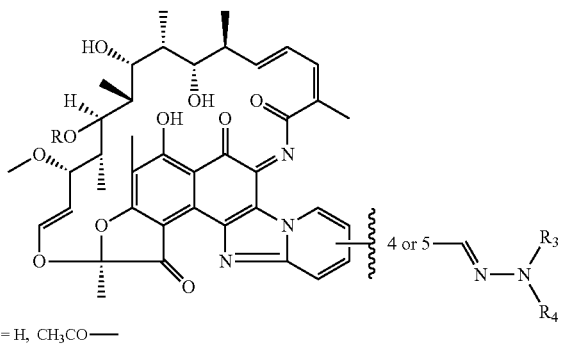

R = H, CH₃CO—

Wherein R₃ and R₄ have the same meaning as described for Scheme 1.

Likewise, starting from 25-desacetylrifamycin S, it is possible to obtain all the derivatives considered in the present invention, deacylated in position 25-, following, for example, the synthesis scheme below (Scheme 4). Starting from 3-halo-25-desacetylrifamycin S, it is reacted with the desired hydrazone of 2-amino-4/5-formylpyridine, or with 2-amino-4-methylolrifamycin S, the condensation product is oxidized with a suitable oxidant to 25-desacetyl-4'-formyl-4-desoxypyrido[1',2'-1,2]imidazo[5,4-c]rifamycin SV, and it is condensed with the desired hydrazine (Scheme 4).

Scheme 4

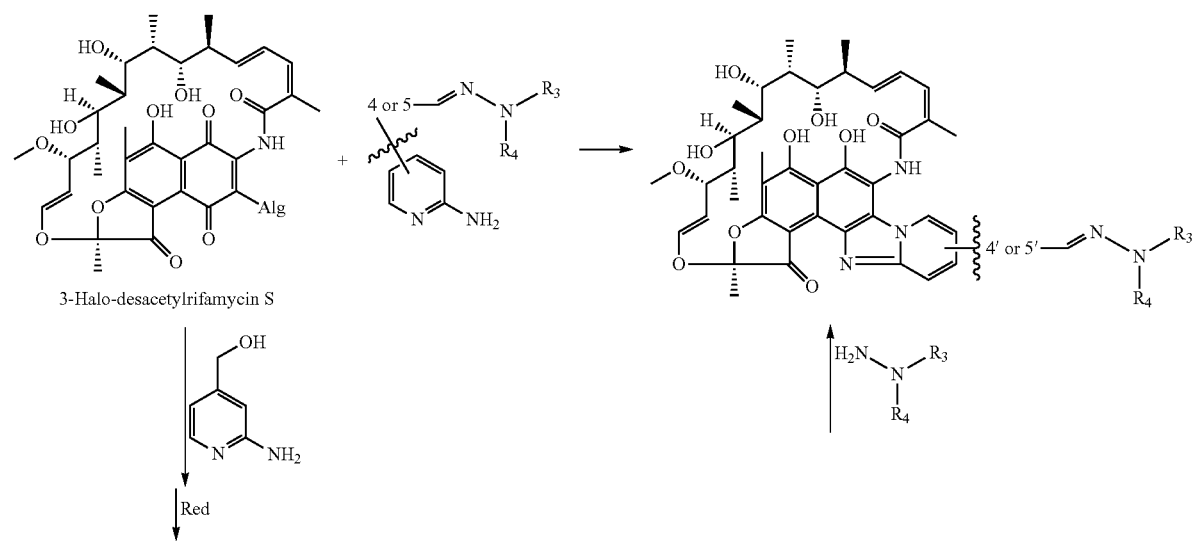

-continued

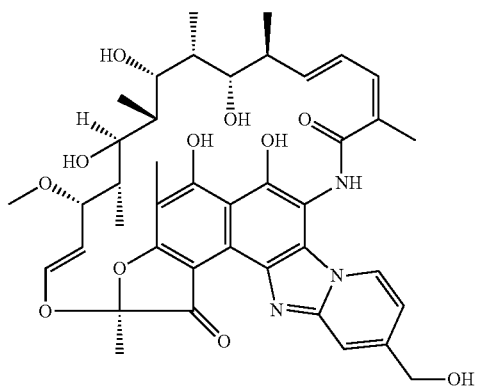

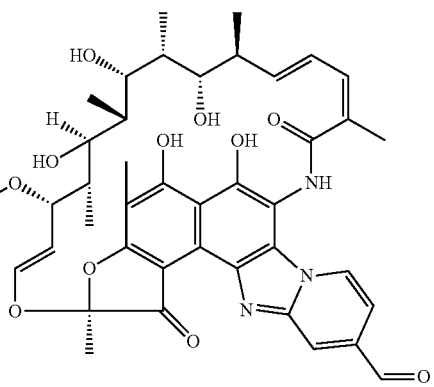

$R_3$ and $R_4$ have the same meaning as described for Scheme 1.

In the Schemes 1-4, organic solvents selected from an aliphatic alkanol containing from 1 to 4 carbon atoms, alone or in a mixture with water, or with DMF, or in a short-chain halogenated solvent, such as dichloromethane, are used.

Preferably, the reaction temperature may vary from a temperature of 10° C. to the solvent boiling point, however not above 80° C., while the reaction time may vary from a few minutes to 24 h.

EXAMPLES

A) Products Obtained Following the Method Illustrated in Scheme 1

Example 1. Obtainment of 4'-methylol-4-desoxy-pyrido[1',2'-1,2]imidazo[5,4-c]rifamycin SV

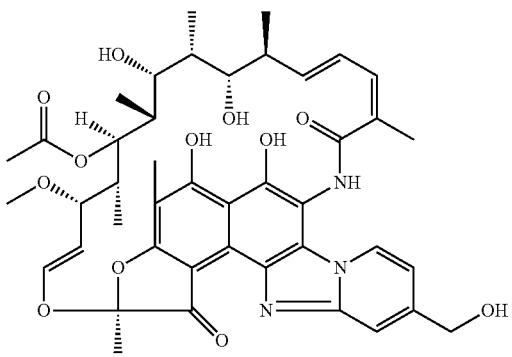 [SMILES: CO[C@H]1/C=C/O[C@@]2(C)Oc3c(C)c(O)c4c(O)c(c5c(nc6cc(CO)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

5.03 g of Rifamycin O (6.67 mmol) are suspended in 38 mL of ethanol at 70° C.; 2.48 g of 2-amino-4-hydroxymethylpyridine (19.97 mmol) are added, and the mixture is left under stirring at 70° C. for 4 h.

The solution is brought to room temperature and diluted with 190 mL of dichloromethane, the organic layer is washed twice with 10% ascorbic acid, and once with saturated sodium chloride solution, and finally with distilled water. The dried organic layer is filtered and evaporated, the crude residue is crystallized by a 1:5.5 ethanol/diethyl ether mixture obtaining 3.60 g of product as a red-orange solid.

Example 2. Obtainment of 4'-formyl-4-desoxy-pyrido[1',2'-1,2]imidazo[5,4-c]rifamycin SV

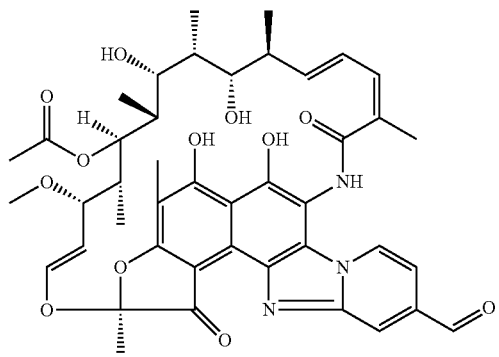 [SMILES: CO[C@H]1/C=C/O[C@@]2(C)Oc3c(C)c(O)c4c(O)c(c5c(nc6cc(C=O)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

4.52 g of 4'-methylol-4-desoxypyrido[1',2'-1,2]imidazo[5,4-c]rifamycin SV (5.64 mmol) are dissolved in 32 mL of dichloromethane, and 22.6 g of manganese dioxide are added to the solution at 40° C. for 1 h. After returning the reaction mixture to room temperature, the manganese dioxide is filtered off and taken up in dichloromethane. 3.73 g of 4'-formyl-4-desoxypyrido[1',2'-1,2]imidazo[5,4-c]rifamycin S are obtained by evaporation of the solvent. 3.73 g of 4'-formyl-4-desoxypyrido[1',2'-1,2]imidazo[5,4-c]rifamycin S are then dissolved in 45 mL of acetonitrile and vigorously stirred with 10 mL of 15% ascorbic acid for 30'.

The reaction mixture is diluted with 200 mL of dichloromethane and washed several times with distilled water, then dried and, after evaporation of the solvent, the reaction crude is washed with diethyl ether, obtaining 3.03 g of product as a purplish solid.

Example 2A. General method for the obtainment of 4'-[(alkyloxy-iminomethyl]-4-desoxypyrido[1',2'-1,2]imidazo[5,4-c]rifamycin SV 0.79 g of 4'-formyl-4-desoxypyrido[1',2'-1,2]imidazo[5,4-c]rifamycin SV (1 mMol, 1 eq), obtained according to Example 2, are dissolved at 10% (w/v) in acetonitrile. An O-alkyl-hydroxylamine (1,5-4 eq) is added and left under stirring for a time of between 60-120', monitoring the reaction by TLC. The reaction mixture is diluted with ethyl acetate (3 volumes) and washed several times with water. The organic layer is evaporated to dryness, and the residue is purified by crystallization from isopropanol to obtain the corresponding 4'-alkyloxy-iminomethyl rifamycin (55-80% yield).

With this method, O-methyl, -ethyl, -propyl, -isopropyl, -butyl, -pentylhydroxylamine oximes are preferably obtained.

Example 2B. General method for the obtainment of 4'-[N-alkyliminomethyl]-4-desoxypyrido[1',2'-1,2]imidazo[5,4-c]rifamycin SV 0.79 g of 4'-formyl-4-desoxypyrido[1',2'-1,2]imidazo[5,4-c]rifamycin SV (1 mMol, 1 eq), obtained according to Example 2, are dissolved at 20% (w/v) in dichloromethane and catalytic trifluoroacetic acid (5 drops). A N-alkyl-amine (4-10 eq) is added and left under stirring for a time of between 2-6 h, monitoring the reaction by TLC. The reaction mixture is diluted with ethyl acetate (5 volumes) and washed several times with 0.1N HCl, and finally with water. The organic layer is evaporated to dryness, and the residue purified by column chromatography to obtain the corresponding 4'-N-alkyliminomethyl rifamycin (30-70% yield).

With this method, methyl-, ethyl-, propyl-, isopropyl-, butyl-, pentyl-, and hexylamine imines are preferably obtained.

Example 3. Obtainment of 4'-[(4-methyl-1-piperazinyl)iminomethyl]-4-desoxypyrido[1',2'-1,2]imidazo[5,4-c]rifamycin SV

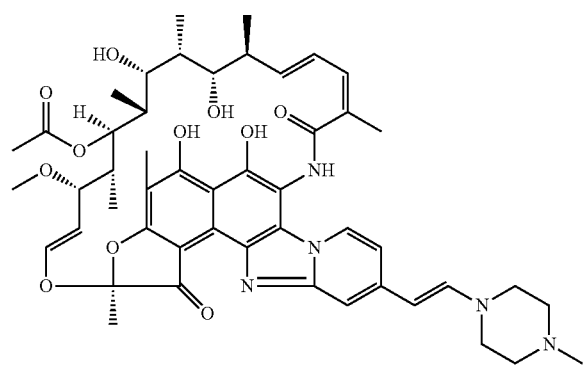 [SMILES: CO[C@H]1/C=C/O[C@@]2(C)Oc3c(C)c(O)c4c(O)c(c5c(nc6cc(/C=C/N7CCN(C)CC7)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

To 3.03 g (3.79 mmol) of 4'-formyl-4-desoxypyrido[1',2'-1,2]imidazo[5,4-c]rifamycin SV, obtained according to Example 2 and dissolved in 30 mL of acetonitrile, 2.5 equivalents of 1-amino-4-methyl-piperazine are added. The solution is left under stirring for about 1 h at room temperature, then it is diluted with 250 mL of dichloromethane, and washed with a 10% ascorbic acid solution, and several times with distilled water; 3.38 g of crude product are obtained by evaporating the solvent which are purified on silica gel using a 95:5 dichloromethane/methanol mixture and obtaining 1.06 g of product.

Example 4. Obtainment of 4'-[(1-piperidinyl)iminomethyl]-4-desoxypyrido[1',2'-1,2]imidazo[5,4-c]rifamycin SV

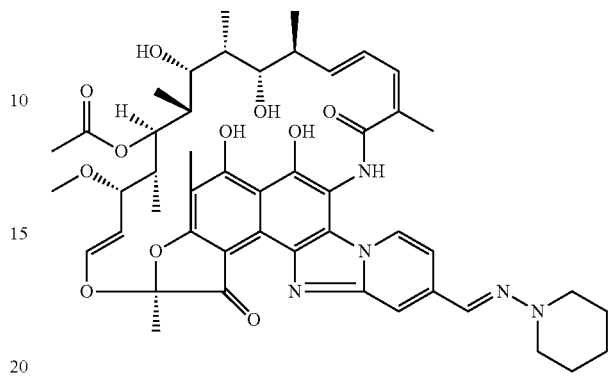

To 0.40 g (0.5 mmol) of reduced product obtained from Example 2, dissolved in 10 mL of acetonitrile, 0.25 g of 1-amino-piperidine (2.5 mmol) are added. The solution is left at room temperature for 3.5 h, then it is diluted with 100 mL of ethyl acetate, and washed with a 10% ascorbic acid solution, then with ammonium chloride at pH 5.2-5.3, saturated sodium chloride solution, and distilled water. The organic layer is dried and, after evaporation of the solvent, the crude is purified on silica gel using a 95:5 dichloromethane/methanol mixture and obtaining 0.15 g of product.

Example 5. Obtainment of 4'-[(N,N-dimethylamino)iminomethyl]-4-desoxypyrido[1',2'-1,2]imidazo[5,4-c]rifamycin SV

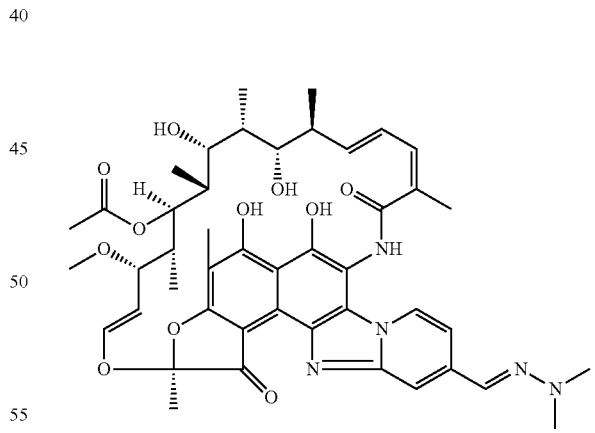

To 0.55 g (0.675 mmol) of reduced product obtained from Example 2, dissolved in 20 mL of acetonitrile, 0.203 g of dimethylhydrazine (3.38 mmol) are added, and the solution is left under stirring at room temperature for 3.5 h. The reaction mixture is diluted with 80 mL of ethyl acetate, and the organic layer is washed twice with 10% ascorbic acid, once with a saturated sodium chloride solution, and twice with distilled water. The organic layer is evaporated, and the residue purified on silica gel using a 95:5 dichloromethane/methanol mixture and obtaining 0.25 g of product.

Example 6. Obtainment of 4'-[(4-carboxyamidopyridyl)iminomethyl]-4-desoxypyrido[1',2'-1,2]imidazo[5,4-c]rifamycin SV

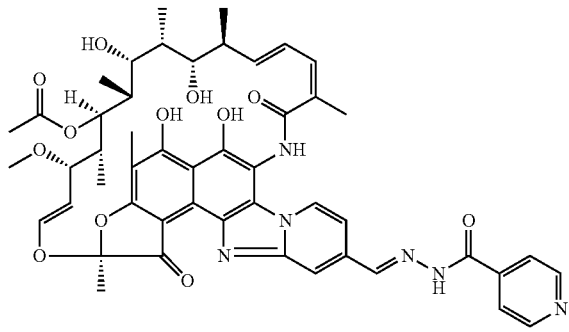 [SMILES: CO[C@H]1/C=C/O[C@@]2(C)Oc3c(C)c(O)c4c(O)c(c5c(nc6cc(/C=N/NC(=O)c7ccncc7)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

To 0.35 g (0.44 mmol) of reduced product obtained from Example 2, dissolved in 7 mL of acetonitrile, 0.30 g of isoniazid (2.19 mmol) are added. The solution is left under stirring at room temperature for 18 h, then it is diluted with 80 mL of ethyl acetate and washed once with a saturated solution of ammonium chloride, and three times with water. The organic layer is evaporated, and the residue purified on silica gel using a 1:3:1 dichloromethane/ethyl acetate/methanol mixture. 0.11 g of product are obtained.

B) Products Obtained Following the Method Shown in Scheme 2

Example 7. Obtainment of 5'-[(N,N-dimethylamino)iminomethyl]-4-desoxypyrido[1',2'-1,2]imidazo[5,4-c]rifamycin SV starting from 3-iodo-rifamycin S

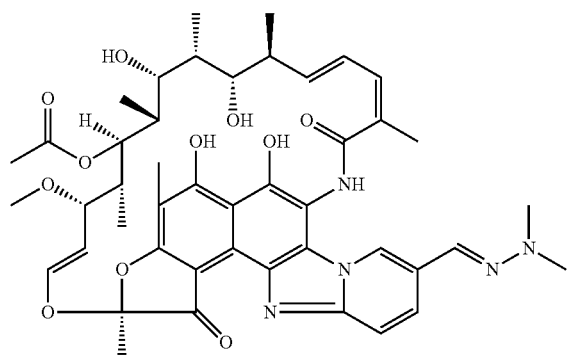 [SMILES: CO[C@H]1/C=C/O[C@@]2(C)Oc3c(C)c(O)c4c(O)c(c5c(nc6ccc(/C=N/N(C)C)cn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

0.20 g of 3-iodo-rifamycin S (0.26 mmol), obtained according to U.S. Pat. No. 4,179,438 patent, are reacted with 1.5 equivalents of 5-(N,N-dimethylamino)-iminomethyl-2-amino-pyridine in dichloromethane (5% solution) at room temperature. This is allowed to react for 20 h, diluted with 2 volumes of dichloromethane, and two washings with 10% ascorbic acid, two washings with 0.1M hydrochloric acid, one washing with a saturated sodium chloride solution, and two washings with distilled water are performed. The organic layer is evaporated, and the residue purified on silica gel using a 9:1 dichloromethane/methanol mixture, obtaining 0.15 g of product.

Example 8. Obtainment of 5'-[(1-piperidinyl)iminomethyl]-4-desoxypyrido[1',2'-1,2]imidazo[5,4-c]rifamycin SV starting from 3-iodo-rifamycin S

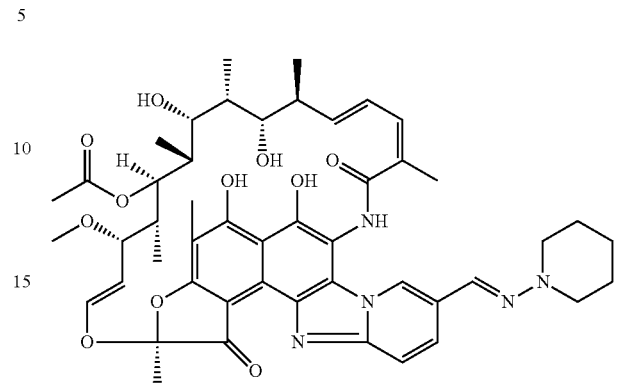

0.35 g of 3-iodo-rifamycin S (0.45 mmol) obtained according to U.S. Pat. No. 4,179,438 patent, are reacted with 1.5 equivalents of 5-(1-piperidinyl)-iminomethyl-2-aminopyridine at room temperature in dichloromethane (5% solution). This is allowed to react for 20 h, diluted with 2 volumes of dichloromethane, and two washings with 10% ascorbic acid, two washings with 0.1M hydrochloric acid, one washing with a saturated sodium chloride solution, and two washings with distilled water are performed. The organic layer is evaporated, and the residue purified on silica gel using a 9:1 dichloromethane/methanol mixture, obtaining 0.13 g of product.

Example 9. Obtainment of 5'-[(N,N-dimethylamino)iminomethyl]-4-desoxypyrido[1',2'-1,2]imidazo[5,4-c]rifamycin SV starting from Rifamycin O

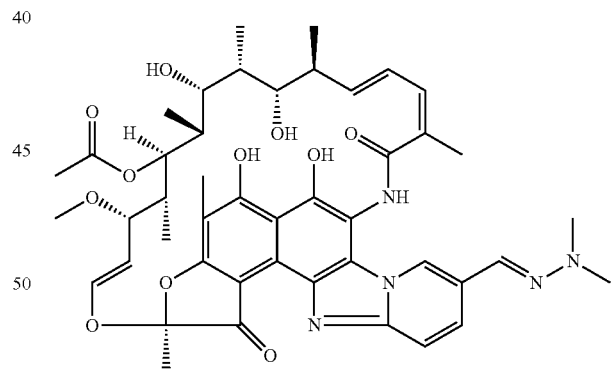

0.30 g of Rifamycin O (0.40 mmol) are dissolved in 30 mL of ethanol and reacted with 2 equivalents of 5-(N,N-dimethylamino)-iminomethyl-2-amino-pyridine. This is allowed to react for about 10 h, then 80 mL of dichloromethane are added, and several washings with 10% ascorbic acid, 0.1N hydrochloric acid and distilled water are performed, then it is dried and evaporated to dryness. The residue is purified on silica gel using a 9:1 dichloromethane/methanol mixture, and obtaining 0.13 g of product.

By operating in the same way as in Example 9, all the substituted derivatives in 4- and 5-position can also be obtained starting from the corresponding 2-aminopyridine.

C) Products Obtained Following the Method Shown in Scheme 3

Example 10. Obtainment of 4'-[(4-methyl-1-piperazinyl)iminomethyl]-4-desoxypyrido[1',2'-1,2]imidazo[5,4-c]rifamycin S

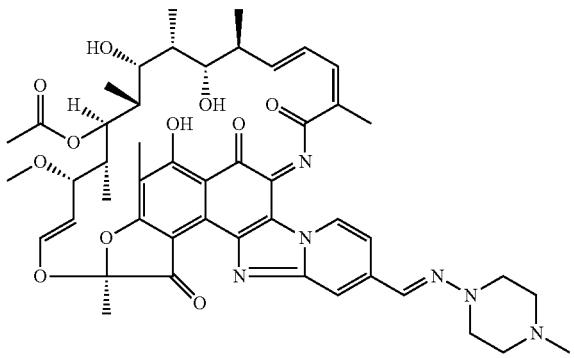

0.50 g of the product 4'-[(-4-methyl-1-piperazinyl)iminomethyl]-4-desoxypyrido[1',2'-1,2]imidazo[5,4-c]rifamycin SV (0.56 mmol), obtained from Example 3, are dissolved in 32 mL of dichloromethane; 1.3 g of manganese dioxide are added to the solution; this is allowed to react for 30 min at room temperature, then the manganese dioxide is filtered off and taken up with dichloromethane. 0.45 g of product are obtained by evaporation of the solvent.

With the method used in Example 10, it is possible to obtain the oxidized form of all the products that were synthesized as a reduced form.

D) Products Obtained Following the Method Shown in Scheme 4

Example 11. Obtainment of 25-desacetyl-5'-[(1-piperidinyl)iminomethyl]-4-desoxypyrido[1',2'-1,2]imidazo[5,4-c]rifamycin SV

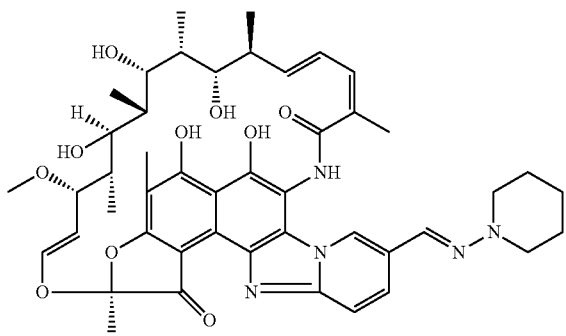 [SMILES: CO[C@H]1/C=C/O[C@@]2(C)Oc3c(C)c(O)c4c(O)c(c5c(nc6ccc(/C=N/N7CCCCC7)cn65)c4c3C2=O)NC(=O)/C(C)=C\C=C\[C@H](C)[C@H](O)[C@@H](C)[C@@H](O)[C@@H](C)[C@H](O)[C@@H]1C]

0.050 g of 3-iodo-25-desacetylrifamycin S (0.066 mmol), obtained according to U.S. Pat. No. 4,179,438 patent, are reacted at room temperature with 2.5 equivalents of 5-(1-piperidinyl)-iminomethyl-2-amino-pyridine in dichloromethane (1.25% solution). The reaction is left under stirring for 12 h and the product crystallizes in the same solvent. Washings with ethyl acetate are performed to eliminate any impurities and obtaining 0.055 g of product.

Example 12. Obtainment of 25-desacetyl-5'-[(N,N-dimethylamino)iminomethyl]-4-desoxypyrido[1',2'-1,2]imidazo[5,4-c]rifamycin SV

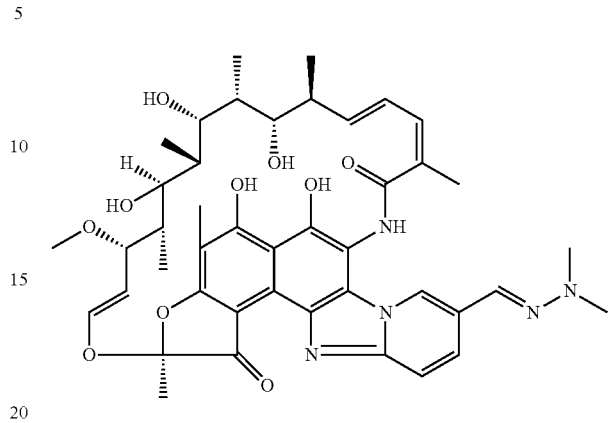

0.20 g of 3-iodo-25-desacetylrifamycin S (0.26 mmol), obtained according to U.S. Pat. No. 4,179,438 patent, are reacted at room temperature with 2.5 equivalents of 5-(N,N-dimethylamino)-iminomethyl-2-amino-pyridine in dichloromethane (3% solution). The reaction is left under stirring for 18 h and the product crystallizes in the same solvent giving, by filtration, 0.09 g of product.

Example 13. Obtainment of 4'-(N-methoxy)-iminomethyl-4-desoxypyrido[1',2'-1,2]imidazo[5,4-c]rifamycin SV

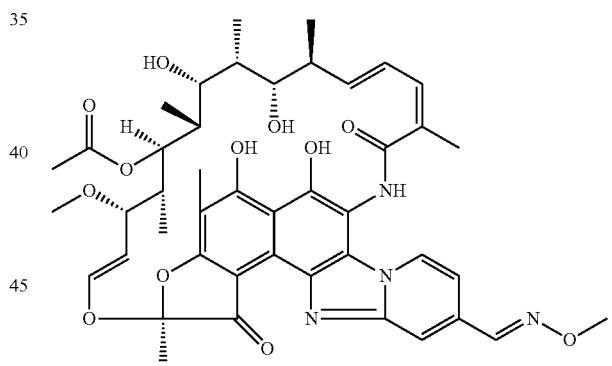

To 168 mg (0.21 mmol) of 4'-formyl-4-desoxypyrido[1',2'-1,2]imidazo[5,4-c]rifamycin SV, obtained according to Example 2 of the present International patent application No. PCT/IB2018/054645 and dissolved in 2.5 mL of a solution of water/THF (1:1.5), 1.5 equivalents of sodium acetate and 1.7 equivalents of methoxyamine hydrochloride are added. The solution is left under stirring for about 4 h at room temperature. The reaction mixture is evaporated to dryness and the crude is purified on silica gel using a 97:3 dichloromethane/methanol mixture and obtaining 97.6 mg of a dark-red product. Yield=56%. Purity estimated by NMR titration with internal standard 1,3,5-trimethoxybenzene was >85%.

$^1$H NMR (600 MHz, CDCl$_3$) δ 16.91 (s, 1H), 15.29 (s, 1H), 8.46-8.37 (m, 1H), 8.25 (d, J=8.6 Hz, 1H), 8.07 (s, 1H), 7.58 (s, 1H), 7.49 (dd, J=7.3, 1.6 Hz, 1H), 6.76 (dt, J=15.9, 11.5 Hz, 1H), 6.30 (d, J=10.7 Hz, 1H), 6.03 (dd, J=16.0, 6.5 Hz, 1H), 5.97 (m, 1H), 4.94 (dd, J=12.6, 5.6 Hz, 1H), 4.81

(dd, J=10.5, 6.0 Hz, 1H), 4.15 (s, 1H), 4.04 (s, 2H), 3.76 (bm, 1H), 3.55 (d, J=9.7 Hz, 1H), 3.25 (td, J=8.1, 6.1, 3.6 Hz, 1H), 2.92 (d, J=4.0 Hz, 3H), 2.80 (d, J=10.1 Hz, 1H), 2.26-2.18 (m, 4H), 1.92-1.85 (m, 9H), 1.54-1.49 (m, 1H), 1.36 (s, 1H), 1.24 (m, 1H), 1.09 (m, 1H), 0.87 (d, J=7.0, Hz, 3H), 0.67 (m, 3H), 0.12 (m, 3H), −0.64 (m, 3H).

$^{13}$C NMR (150.8 MHz, CDCl$_3$) 188.76, 188.59, 182.21, 182.06, 172.00, 171.93, 171.72, 170.44, 170.34, 155.47, 155.37, 151.47, 144.47, 142.36, 142.21, 141.81, 141.71, 141.37, 138.42, 138.22, 138.15, 135.75, 133.45, 129.13, 128.21, 125.47, 125.35, 123.58, 123.53, 120.73, 120.34, 115.84, 115.38, 115.13, 114.87, 114.80, 112.82, 112.24, 112.10, 111.91, 109.23, 108.92, 108.90, 104.74, 104.59, 104.18, 104.11, 98.06, 98.02, 97.93, 77.78, 77.67, 76.81, 74.00, 73.93, 72.76, 72.71, 63.92 (OMe), 63.31 (OMe), 57.13, 57.08, 38.46, 38.10, 37.80, 37.73, 36.89, 36.83, 34.18, 32.88, 32.86, 30.28, 29.65, 21.19, 21.16, 21.14, 20.75, 20.37, 20.36, 17.46, 10.77, 8.46, 8.37, 7.93, 7.81, 6.95, 6.92.

The $^1$H and $^{13}$C spectra show two set of resonances due to the presence of the E/Z isomers of the oxime.

Example 14. Obtainment of 4'-(N-isopropyl)-iminomethyl]-4-desoxypyrido[1',2'-1,2]imidazo[5,4-c]rifamycin SV

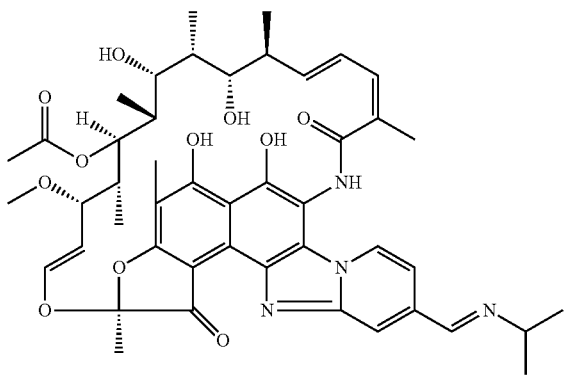 [SMILES: CO[C@H]1/C=C/O[C@@]2(C)Oc3c(C)c(O)c4c(O)c(c5c(nc6cc(/C=N/C(C)C)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

To 50 mg (0.063 mmol) of 4'-formyl-4-desoxypyrido[1', 2'-1,2]imidazo[5,4-c]rifamycin SV, obtained according to Example 2 of the present International patent application No. PCT/IB2018/054645 and dissolved in 2.0 mL of dichloromethane, 5.0 equivalents of magnesium sulfate anhydrous and 3.0 equivalents of isopropyl amine are added. The solution is left under stirring for about 20 minutes at room temperature. The reaction mixture is evaporated to dryness. The crude is dissolved in 10 mL of dichloromethane and filtered to give 50.4 mg of a dark-red product. Yield=95%. Purity estimated by NMR titration with internal standard 1,3,5-trimethoxybenzene was >85%. The NMR spectrum in CDCl$_3$ must be prepared by passing the CDCl$_3$ through a basic Al$_2$O$_3$ plug, to remove any trace of acidity.

$^1$H NMR (600 MHz, CDCl$_3$) δ 17.36 (bs, 1H), 15.87 (bs, 1H), 8.52 (d, J=7.2 Hz, 1H), 8.41 (s, 1H), 7.98 (s, 1H), 7.90 (t, J=1.2 Hz, 1H), 7.74 (dd, J=7.2, 1.6 Hz, 1H), 6.92 (dd, J=16.0, 10.7 Hz, 1H), 6.39 (d, J=10.5 Hz, 1H), 6.18-6.11 (m, 2H), 5.12 (dd, J=12.4, 5.5 Hz, 1H), 5.00-4.95 (m, 1H), 3.90 (d, J=5.4 Hz, 1H), 3.75-3.68 (m, 2H), 3.59 (s, 1H), 3.40 (ddd, J=5.7, 2.5, 1.3 Hz, 1H), 3.05 (s, 3H), 2.93 (d, J=10.2 Hz, 1H), 2.32 (h, J=6.9 Hz, 1H), 2.25 (d, J=1.3 Hz, 3H), 2.16 (s, 3H), 2.01 (s, 3H), 1.88 (s, 3H), 1.64 (m, 1H), 1.46 (m, 1H), 1.31 (d, J=7.8, 3H), 1.30 (d, J=7.8, 3H), 1.23-1.20 (m, 1H), 0.98 (d, J=7.0 Hz, 3H), 0.92-0.81 (m, 1H), 0.78 (d, J=7.0 Hz, 3H), 0.37 (d, J=6.8 Hz, 3H), −0.36 (d, J=7.1 Hz, 3H).

$^{13}$C NMR (150.8 MHz, CDCl$_3$) 188.73, 182.17, 171.95, 171.77, 170.31, 155.32, 153.85 (CH), 142.29, 141.80, 141.71, 138.58, 129.28, 127.84, 125.41, 123.51, 120.51, 115.18, 114.84, 113.13, 112.15, 110.47, 108.83, 104.59, 104.21, 98.00, 77.96, 73.97, 72.62, 61.90 (CH), 57.11, 38.38, 37.87, 36.89, 32.86, 23.89 (CH$_3$), 23.85 (CH$_3$), 21.15, 20.78, 20.36, 17.40, 10.81, 8.53, 7.95, 6.97

Example 15. Obtainment of 4'-(4-morpholyl)-iminomethyl)-4-desoxypyrido[1',2'-1,2]imidazo[5,4-c]rifamycin SV

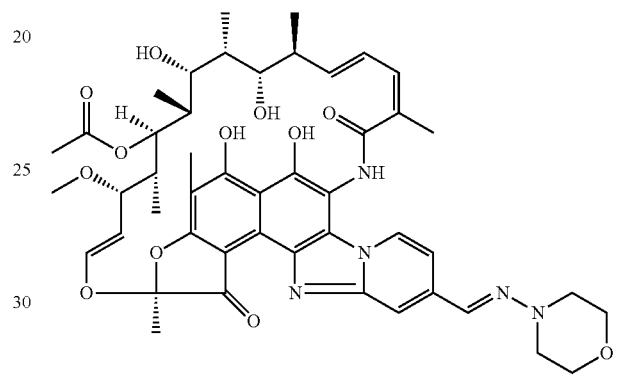

To 200 mg (0.25 mmol) of 4'-formyl-4-desoxypyrido[1', 2'-1,2]imidazo[5,4-c]rifamycin S, obtained according to Example 2 of the present International patent application No. PCT/IB2018/054645 and dissolved in 2.0 mL of acetonitrile, 2.5 equivalents of 4-aminomorpholine are added. The solution is left under stirring for about 2 h at room temperature. After this time it is diluted with 3 mL of acetonitrile and to the reaction 0.5 mL of 15% ascorbic acid solution are added. The solution is left under stirring for about 30 minutes at room temperature. The reaction mixture is evaporated to dryness and the crude is purified on silica gel using a 96:4 dichloromethane/methanol mixture and obtaining 107.5 mg of a red product. Yield=49%. Purity estimated by NMR titration with internal standard 1,3,5-trimethoxybenzene was >92%.

$^1$H NMR (600 MHz, CDCl$_3$) δ 16.98 (bs, 1H), 14.80 (s, 1H), 8.37 (d, J=7.3 Hz, 1H), 8.32 (bs, 1H), 7.55 (d, J=7.3 Hz, 1H), 7.49 (s, 1H), 7.43 (s, 1H), 6.80 (dd, J=16.0, 10.6 Hz, 1H), 6.33 (d, J=10.6 Hz, 1H), 6.10-6.02 (m, 2H), 5.02 (dd, J=12.5, 6.0 Hz, 1H), 4.88 (d, J=10.3 Hz, 1H), 3.92 (m, 4H), 3.77 (s, 1H), 3.62 (d, J=9.5 Hz, 1H), 3.38 (m, 4H), 3.28 (m, 1H), 2.97 (s, 3H), 2.85 (dd, J=10.2, 2.4 Hz, 1H), 2.29 (m, 1H), 2.24 (s, 3H), 1.96 (s, 3H), 1.94 (s, 3H), 1.90 (s, 3H), 1.58 (m, 1H), 1.30 (m, 1H), 1.17 (bs, 2H), 0.93 (d, J=7.0 Hz, 3H), 0.84 (m, 1H), 0.74 (d, J=7.0 Hz, 3H), 0.17 (d, J=6.5 Hz, 3H), −0.54 (d, J=6.9 Hz, 3H).

$^{13}$C NMR (150.8 MHz, CDCl$_3$) 188.95, 181.46, 171.95, 171.82, 170.45, 154.96, 143.01, 142.04, 141.88, 139.26, 136.61, 128.63, 127.46, 125.39, 123.34, 119.90, 115.47, 114.72, 112.27, 111.98, 108.84, 105.39, 104.34, 104.21, 98.11, 78.00, 73.93, 72.65, 66.04 (CH$_2$), 56.99, 50.96 (CH$_2$), 38.55, 37.91, 36.95, 32.90, 21.32, 20.78, 20.39, 17.46, 10.80, 8.37, 8.12, 7.05

Example 16. Biological Test Results

Table 1 shows the minimum inhibitory concentrations (MIC) in μg/mL of the various compounds listed in the examples in comparison to Rifaximin (RFX). The MICs were calculated using the serial dilution method, and are expressed as the range between the last concentration at which the bacterial strain grows and the first concentration at which the strain tested no longer grows.

TABLE 1

| Example | Strain A | Strain B | Strain C | Strain D |
|---------|----------|----------|----------|----------|
| 1 | 8-16 | 2-4 | 8-16 | 4-8 |
| 2 | >64 | >64 | >64 | >64 |
| 3 | 0.03-0.06 | 0.125-0.25 | 4-8 | 0.02-0.04 |
| 4 | 0.03-0.06 | 0.062-0.125 | 4-8 | 8-16 |
| 5 | 0.03-0.06 | 0.062-0.125 | 32-64 | 32-64 |
| 6 | >64 | 8-16 | >64 | 32-64 |
| 7 | 0.03-0.06 | 0.062-0.125 | 32-64 | 32-64 |
| 8 | 0.03-0.06 | 0.062-0.125 | 4-8 | 8-16 |
| 9 | — | — | — | — |
| 10 | — | — | — | — |
| 11 | 8-16 | 4-8 | 32-64 | 32-64 |
| 12 | 8-16 | 4-8 | >64 | >64 |
| 13 | <0.015 | <0.015 | 8-16 | 8-16 |
| 14 | 0.03-0.06 | 8-16 | 8-16 | 8-16 |
| 15 | <0.015 | 8-16 | 8-16 | 4-8 |
| RFX | 0.25-0.5 | 0.125-0.25 | 2-4 | 4-8 |

Strain A) *Staphylococcus aureus* IM149;
Strain B) *Bacillus Subtilis* ATCC 6633;
Strain C) *Escherichia Coli* ATCC 25922;
Strain D) *Escherichia Coli* NK12

As it can be seen from Table 1, Example 3, 13, 14 and 15 showed an antibacterial activity fully comparable to that of RFX, in particular they show a MIC against strain A lower than RFX.

The other examples, despite the non-optimal hydrophilicity/lipophilicity ratio, were nevertheless microbiologically active.

Example 17. Pharmacokinetic Test Results

Pharmacokinetic studies were set with administration of compound 3 (4'-[(4-methyl-1-piperazinyl)iminomethyl]-4-desoxypyrido[1',2'-1,2]imidazo[5,4-c]rifamycin SV) and Rifaximin (RFX), both orally and parenterally, in the rat at the same dose. The pharmacokinetic study of derivative 3 in comparison to RFX was planned by administering the two compounds intravenously and orally, and calculating the kinetic parameters AUC, $C_{max}$, $T_{max}$, and the oral bioavailability compared to the parenteral one.

Intravenous Administration of RFX and Derivative 3: the two products were dissolved, independently, in DMSO obtaining a 4 mg/mL stock solution. To 0.250 mL of this solution, 4.750 mL of saline are added, obtaining a final 0.2 mg/mL (5% DMSO, 95% saline) solution. A volume of 5 mL/Kg is administered to 3 rats in each group to have a 1 mg/Kg dose for each of the two products.

Oral Administration of RFX and Derivative 3: the two products were dissolved in DMSO obtaining two solutions having a 60 mg/mL concentration (stock solutions). To 0.5 mL of each solution, 2.0 mL of PEG 400 and 7.5 mL of saline solution were added under stirring, obtaining a stable suspension with a nominal concentration of 3 mg/mL. A volume equal to a 30 mg/kg dose is administered to the animal.

Male Sprague Dawley rats, weighing between 250 and 300 g, were used in the study. The animals were housed and observed before the experiment according to an approved GMP protocol according to Italian legislation.

The rats were divided into three groups:
Group 1: i.v. treatment
Group 2: oral treatment for blood sampling
Group 3: oral treatment for urine and stool collection
Group 1: blood sampling at: 5, 15, 30, 60, 120, 240, 480, 1440 min. from caudal vein.
Group 2: blood sampling at: 30, 60, 120, 240, 360, 480, 1440 min. from caudal vein.
Group 3: collection of stool and urine in metabolic cages at: 0-4 h, 4-8 h, 8-24 h, 24-48 h, 48-72 h. At the end of the experiment, the blood at 72 h was sampled also from this group of rats as a check.

The analytical method used to analyze the various blood, stool, and urine samples was developed on:
UFLC Shimadzu AC20 coupled with an API 3200 Triple Quadrupole ABSciex.
Injected Volume: 10 μL
Column: Gemini—Nx 5μ C18 110A (50×2.00 mm), column T 35° C.
Gradient: Flow 0.3 mL/min
Mobile Phase A: 15 mM ammonium acetate in water
Mobile Phase B: MeOH
Analysis Range: 1-1000 ng/mL for plasma. Urine: 1-500 ng/mL. Stool: 1-1000 ng/mL.

TABLE 2

| Chromatographic Gradients | |
|---|---|
| Time (min) | % B |
| 0.01 | 30 |
| 0.5 | 30 |
| 1.5 | 98 |
| 3.5 | 98 |
| 4 | 30 |
| 5 | 30 |

A MRN analysis in positive ESI was performed, monitoring the fragments resulting from the main peak according to Table 2.

TABLE 3

| Positive MS ESI Results. | | |
|---|---|---|
| Compound | Parent Ion | Product Ion |
| Rifaximin | 786.3 | 754.3 |
| <u>3</u> | 897.2 | 865.3 |

Sample Preparation

Plasma: the calibration curve and the QC samples were prepared in untreated rat plasma, adding 5 μL of each stock solution to 45 μL of untreated rat plasma. The 50 μL of plasma obtained were diluted up to 100 μL with cold acetonitrile containing the Internal Standard (I.S.) at the final concentration of 50 ng/mL, and centrifuged for 5 min. at 9000 rpm at 5° C. The supernatant was transferred to a 96-well plate for analysis. The samples of Groups 1 and 2 were similarly prepared using 50 μL of plasma from the treated rats.

Urine: the calibration curve and the QC samples were prepared in untreated rat urine, adding 5 μL of each stock solution to 45 μL of untreated rat urine. The 50 μL of urine obtained were diluted up to 100 μL with cold acetonitrile, containing the I.S. at the final concentration of 50 ng/mL, and centrifuged for 5 min. at 9000 rpm at 5° C. The supernatant was transferred to a 96-well plate for analysis. The samples of Groups 1 and 2 were similarly prepared using 50 μL of plasma from the treated rats.

Stool: Stool samples were homogenized by suspending 1 g of stool in 3 mL of 15 mM ammonium acetate buffer at pH 4.3. The calibration curve and the QC samples were prepared in untreated rat stool, by adding 5 μL of each stock solution to 45 μL of homogenized untreated rat stool. The 50 μL of homogenized stool obtained were diluted up to 200 μL with cold acetonitrile, containing the I.S. at the final concentration of 50 ng/mL, in a 96-well plate. The samples were centrifuged for 15 min. at 3000 rpm and the supernatant was transferred into a clean plate for analysis.

Analytical Data—Pharmacokinetic Analysis

A non-compartmental analysis was applied, and the following pharmacokinetic parameters were considered for each subject:

$C_{max}$: Maximum Plasma Concentration $C_{last}$: Plasma concentration at the last sampling $t_{max}$: Time of maximum plasma concentration $AUC_{0-last}$: AUC from $t_0$ to the time of the last detectable concentration $AUC_{inf}$: AUC extrapolated from time 0 to infinite time=$\int_0^\infty C\,dt$ $MRT_{inf}$:

$$\text{Average Residence Time} = \frac{1}{N}\sum_{i=1}^{m} t_i n_i$$

$t_{1/2}$:

$$\text{Half-life time} = \frac{\ln(2)}{k_e}$$

The concentration data were extrapolated using the Analyst™ 6.1 software (Applied Biosystems); the AUCs were calculated using a linear-trapezoidal method, and a weight uniformity was performed as the first approach. The concentration/time graphs were performed after logarithmic transformation of the results using PK Solver 2.0 software, Excel 2007 Microsoft add in.

Results

TABLE 4

Pharmacokinetic parameters of 3 and Rifaximin (RFX) after intravenous (IV) and oral (PO) administration in male rats.

| Parameter | Unit of Measure | Compound 3 Average | SD | RFX Average | SD |
|---|---|---|---|---|---|
| IV | | | | | |
| $t_{1/2}$ | min | 241 | 108 | 147 | 32 |
| $T_{max}$ | min | 8.3 | 5.8 | 5 | 0 |
| $C_{max}$ | ng/mL | 768 | 647.2 | 2881 | 1320 |
| $C_0$ | ng/mL | 771 | 514.6 | 3755 | 1210 |
| AUC 0-t | ng/mL × min | 49593 | 48159 | 119249 | 52327 |
| AUC 0-inf | ng/mL × min | 49743 | 48110 | 119476 | 52114 |
| MRT 0-inf | min | 97 | 22 | 71 | 19 |
| Cl_obs | mL/min × kg | 38.3 | 32.3 | 9.8 | 5.2 |
| Vss_obs | L/kg | 4.2 | 3.9 | 0.757 | 0.563 |
| PO | | | | | |
| $t_{1/2}$ | min | 138 | 18 | 578 | 78 |
| $T_{max}$ | min | 30 | 0 | 30 | 0 |
| $C_{max}$ | ng/mL | 6.7 | 0.5 | 57.1 | 23.3 |
| AUC 0-t | ng/mL × min | 747 | 146 | 11795 | 2837 |
| AUC 0-inf | ng/mL × min | 855 | 204 | 13341 | 2482 |
| MRT 0-inf | min | 196 | 28 | 553 | 162 |
| FPO % | | 0.06 | | 0.4 | |

TABLE 5

Concentration of 3 and Rifaximin (RFX) in rat urine after oral administration at 30 mg/Kg.

| Time (h) | Comp. 3 Average | SD | RFX Average | SD |
|---|---|---|---|---|
| Urine Concentration (ng/mL) | | | | |
| 0-4 | 157.0 | 210.9 | 156.7 | 28.7 |
| 4-8 | 27.0 | 25.2 | 147.3 | 74.6 |
| 8-24 | 49.2 | 64.0 | 605.3 | 743.9 |
| 24-48 | 103.0 | 131.9 | 682.7 | 942.8 |
| 48-72 | 9.5 | 6.3 | 348.1 | 3917 |
| Total Urine Concentration (ng) | | | | |
| 0-4 | 507.5 | 671.6 | 509 | 168 |
| 4-8 | 30.4 | 23.6 | 254 | 105 |
| 8-24 | 212.2 | 287.7 | 2908 | 3706 |
| 24-48 | 422.9 | 567.9 | 3743 | 5167 |
| 48-72 | 43.1 | 34.0 | 2110 | 2974 |

TABLE 6

Concentration of 3 and Rifaximin (RFX) in rat stool after oral administration at 30 mg/Kg.

| Time (h) | Comp. 3 Average | SD | RFX Average | SD |
|---|---|---|---|---|
| Stool Concentration (ng/g) | | | | |
| 0-4 | <LOQ | | 248 | 226 |
| 4-8 | 27258 | 9114 | 35774 | 49879 |
| 8-24 | 20409 | 4357 | 64032 | 15505 |
| 24-48 | 1609 | 1195 | 5796 | 6387 |
| 48-72 | 112 | 119 | 446 | 31 |
| Total Stool Concentration (ng) | | | | |
| 0-4 | <LOQ | | 137 | 70 |
| 4-8 | 61364 | 14568 | 122016 | 171859 |
| 8-24 | 157285 | 32439 | 562304 | 136734 |
| 24-48 | 12291 | 8520 | 60616 | 66716 |
| 48-72 | 1495 | 1310 | 5883 | 1285 |

Example 3 according to the invention showed intestinal absorption 7-8 times lower, i.e. about 15%, compared to that shown and confirmed in the literature by Rifaximin.

Example 18

Antibacterial activity against eukaryotic bacterial strains of *Bifidobacterium, Enterococcus, Enterobacteriacaee*, and Lactobacillus species was detected after oral administration of product 3 and Rifaximin, as a comparison, in Sprague Dawley rats.

Treatment

Two groups of 6 Sprague Dawley rats weighing approximately 250 g/rat were treated, after the acclimatization period, by means of a gastric probe, for 5 days at a 50 mg/kg dose of 3 and Rifaximin, as a comparison. The stools were collected at T0 and the day after the last treatment.

The two products were first dissolved in DMSO at the concentration of 100 mg/mL (stock solution), then to 0.5 mL of each solution 2.0 mL of PEG 400 and 7.5 mL of saline solution were added, under stirring. A stable suspension at the nominal concentration of 5 mg/mL is obtained. A volume of 10 mL/kg, equal to 50 mg/kg, is administered.

Method

The detection method is based on isolation of the total genomic DNA from each stool sample, using a specific commercial kit. After the quali-quantitative evaluation of the DNA, the same DNA samples were stored at −20° C. Quantitative analyzes were performed using qPCR Real Time with the use of a DNA primer couples specific for *Bifidobacterium, Enterococcus, Enterobacter*, and *Lactobacillus* species.

DNA isolation was performed using the PowerFecal® DNA Isolation Kit (MO BIO Laboratories) commercial kit on a sample of 250 mg stool, each time. After isolation, the DNA samples were evaluated by spectrophotometric analysis. Each DNA sample was quantified in the 60-100 ng/μL range (high in proteins and sugars), as typical for stool-derived DNA.

Quantitative Analysis of qPCR

Each sample was evaluated three times. For each DNA sample and for each specific DNA primer couple, the analysis provided a CT value that resulted to be correlated to the amount of DNA specific to the bacterial species, therefore closely correlated to the number of bacterial cells of that species present in the stool sample.

For relative quantification, a "generalized linear mixed model (GLMM) under Poisson-lognormal error" was applied. MCMC.qPCR R package was used to convert CT values into bacterial cell numbers. For the conversion, the formula: Number of cells=$E^{(Ct1-Ct)}$ was used, where E represents the efficiency of amplification, which in the present case assumes the value of 2. Ct1 represents the number of qPCR cycles needed to detect a single target molecule (in this study Ct1 is supposed to have the value of 39).

The Markov Chain Monte Carlo algorithm (MCMC) was used to estimate the effect of time on the development levels of each microbial genus. The GLMM method was used to verify if the levels of each bacterial genus at T0 and T5 differ. Furthermore, a statistical analysis to evaluate the significance of the differences between the T0 and T5 values was performed.

Results

Figure 3:
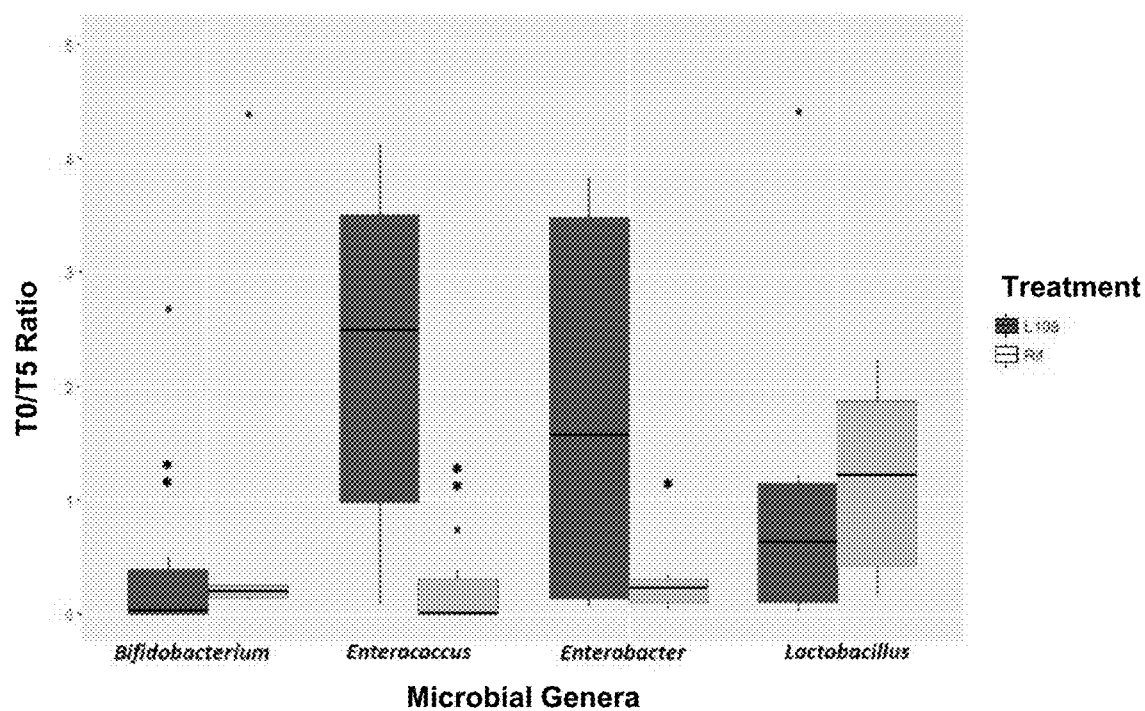
FIG. 3 shows the effect of the compound of Example 3 and Rifaximin on the tested eukaryotic bacterial strains. Above the bars the statistical analyzes between the treatments are reported (*P<0.1; **P<0.05)
Figure 4:
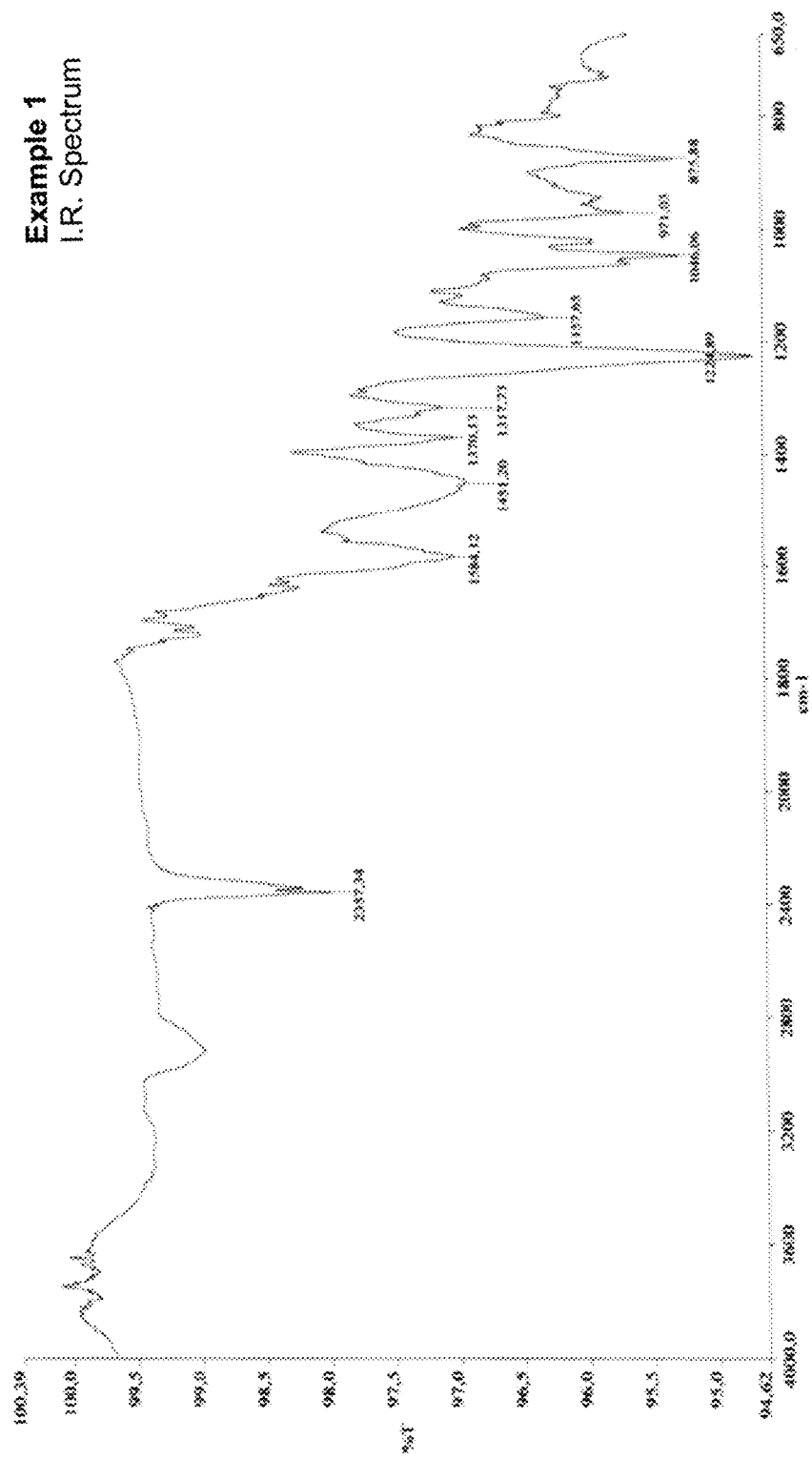
FIG. 4 shows the I.R. spectrum of the compound 4'-methylol-4-desoxypyrido[1',2'-1,2]imidazo[5,4-c]rifamycin SV obtained in the Example 1.
Figure 5:
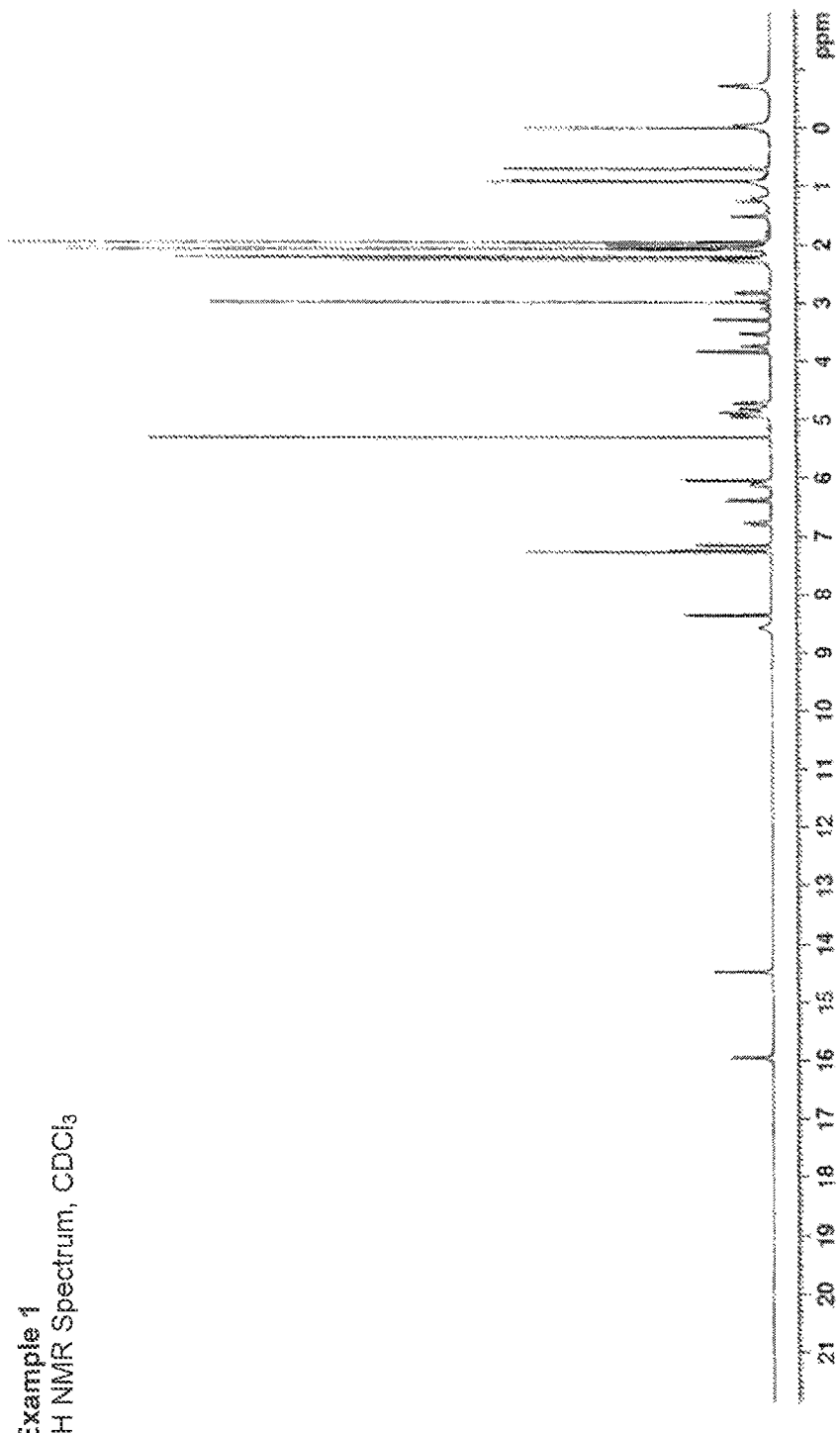
FIG. 5 shows the $^1$H NMR spectrum in CDCl$_3$ of the compound 4'-methylol-4-desoxypyrido[1',2'-1,2]imidazo[5,4-c]rifamycin SV obtained in the Example 1.
Figure 6:
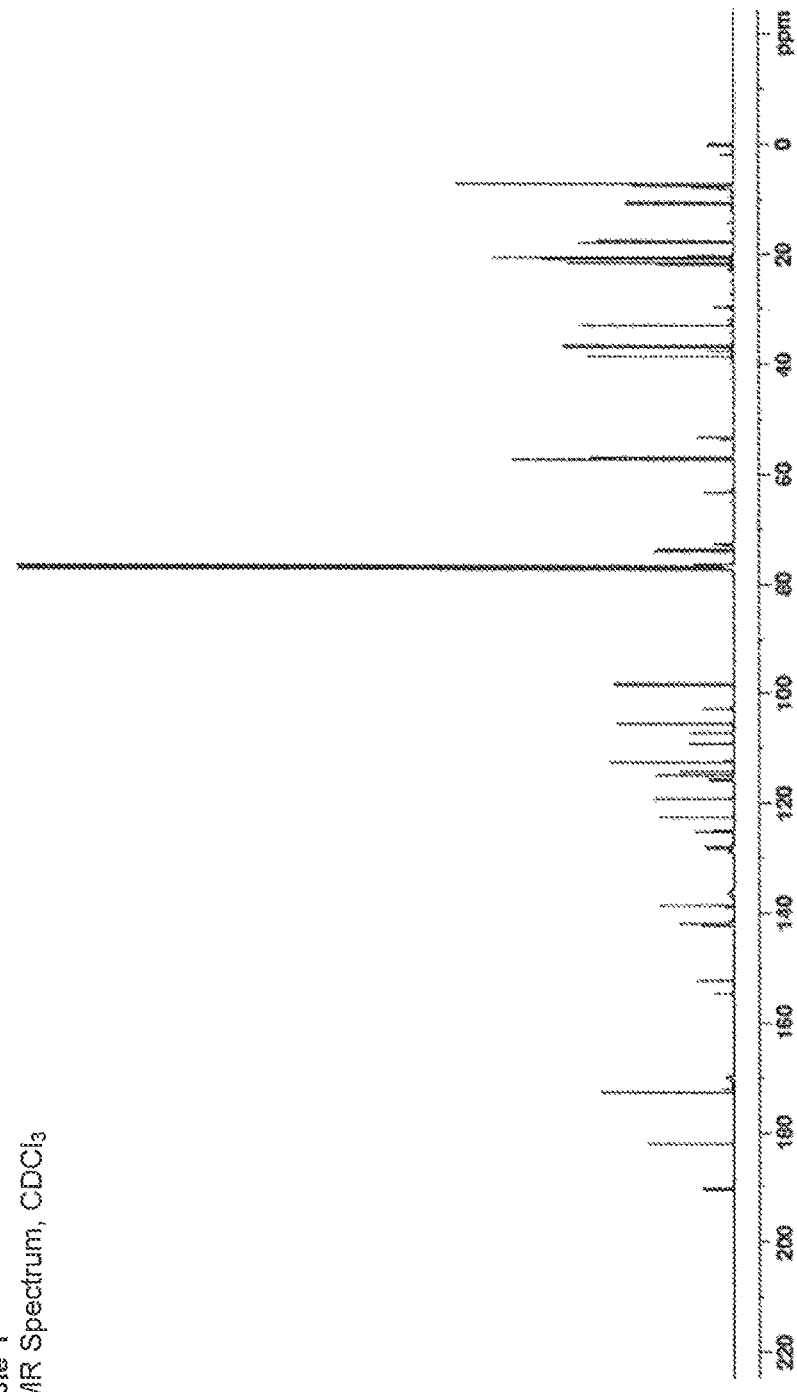
FIG. 6 shows the $^{13}$C NMR spectrum in CDCl$_3$ of the compound 4'-methylol-4-desoxypyrido[1',2'-1,2]imidazo[5,4-c]rifamycin SV obtained in the Example 1.
Figure 7:
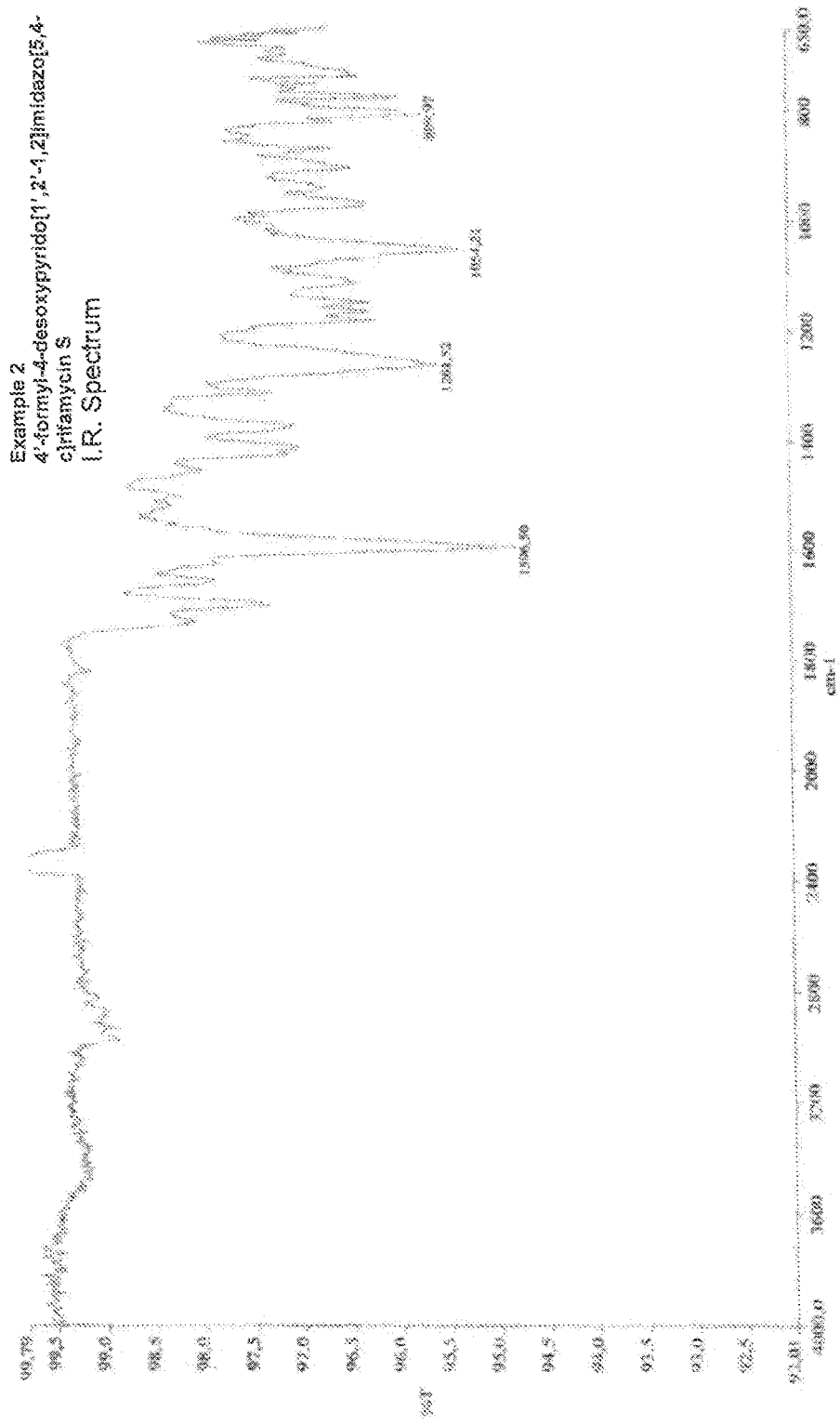
FIG. 7 shows the I.R. spectrum of the compound 4'-formyl-4-desoxypyrido[1',2'-1,2]imidazo[5,4-c]rifamycin S obtained in the Example 2.
Figure 8:
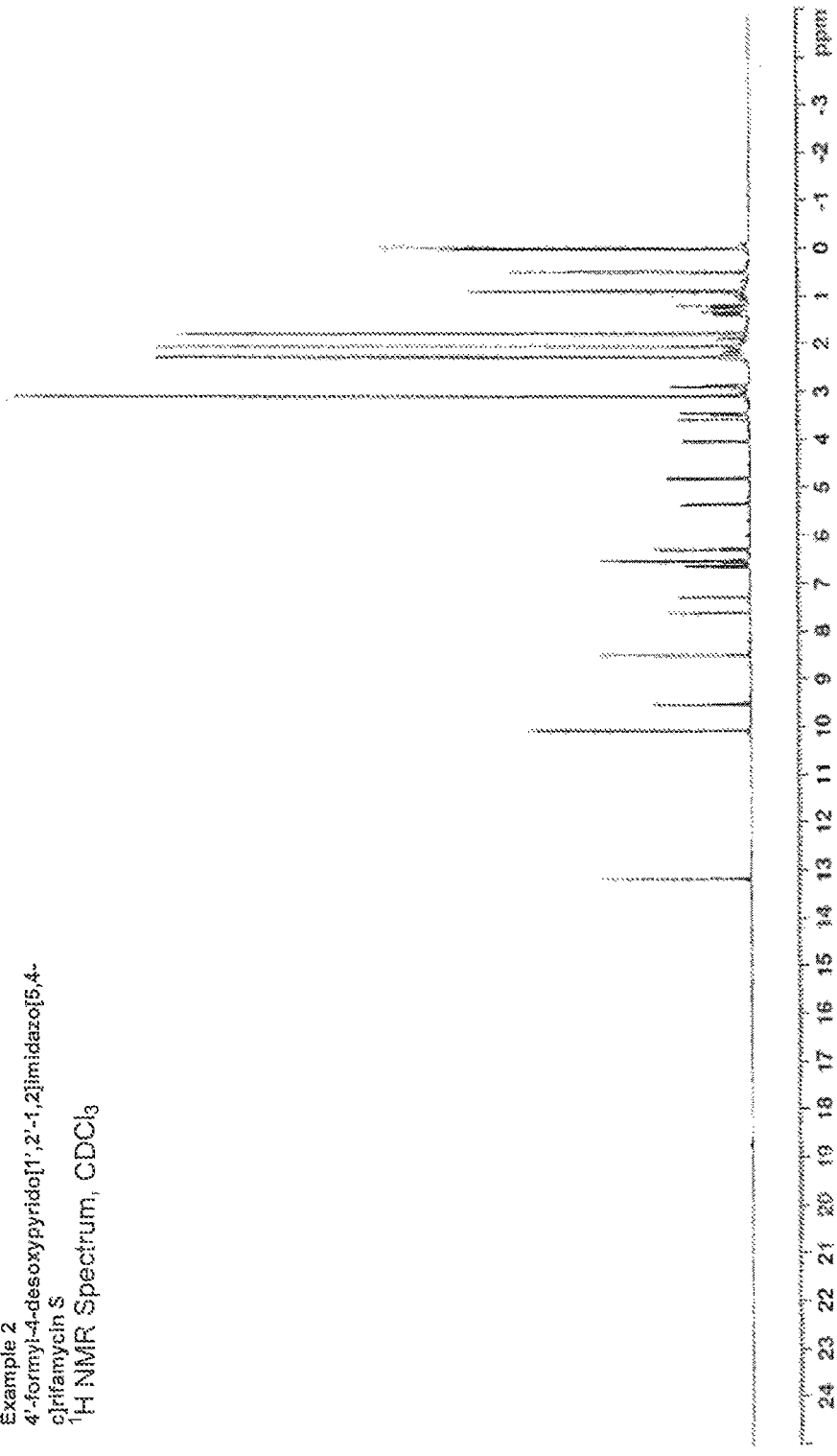
FIG. 8 shows the $^1$H NMR spectrum in CDCl$_3$ of the compound 4'-formyl-4-desoxypyrido[1',2'-1,2]imidazo[5,4-c]rifamycin S obtained in the Example 2.
Figure 9:
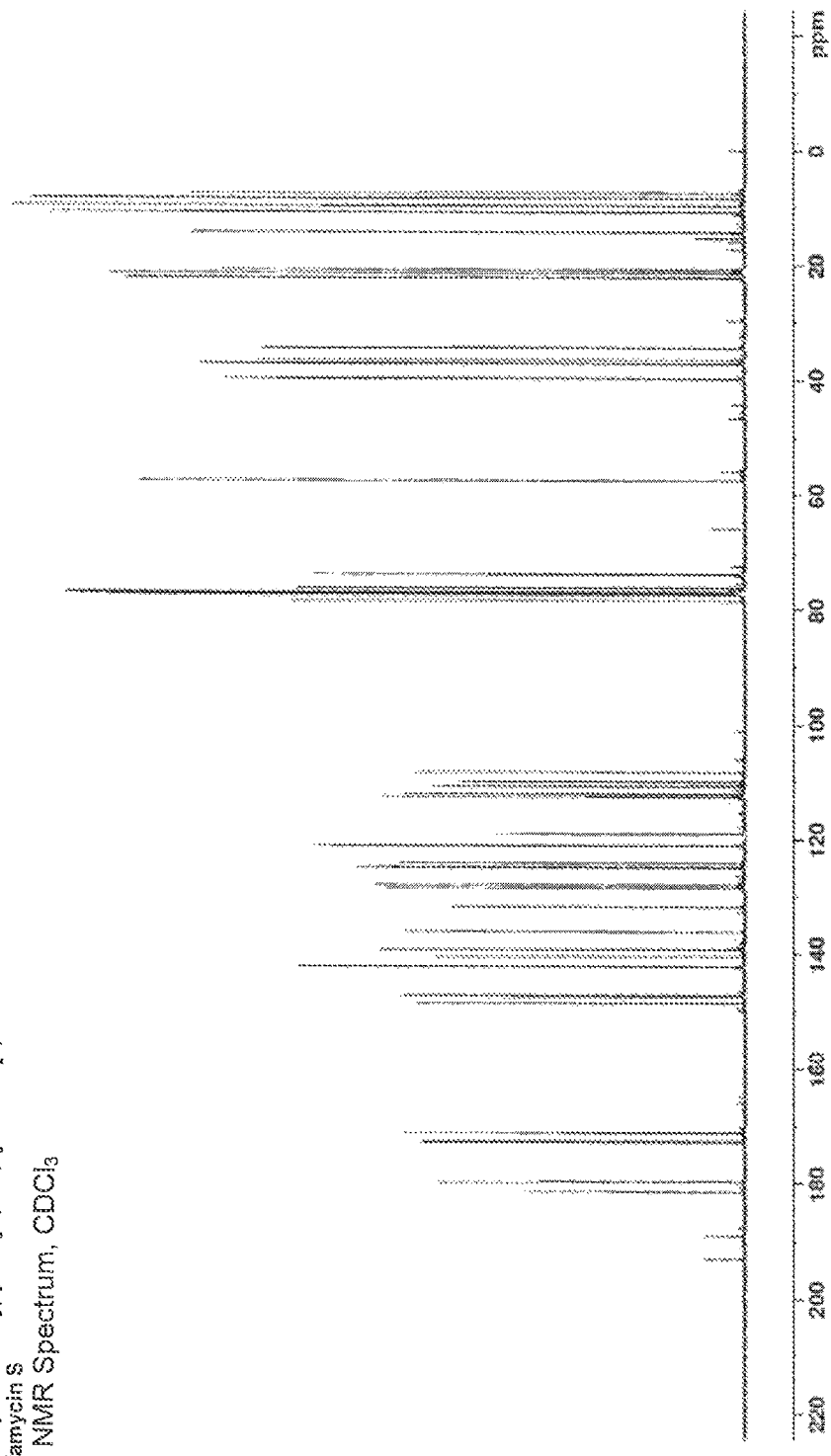
FIG. 9 shows the $^{13}$C NMR spectrum in CDCl$_3$ of the compound 4'-formyl-4-desoxypyrido[1',2'-1,2]imidazo[5,4-c]rifamycin S obtained in the Example 2.
Figure 10:
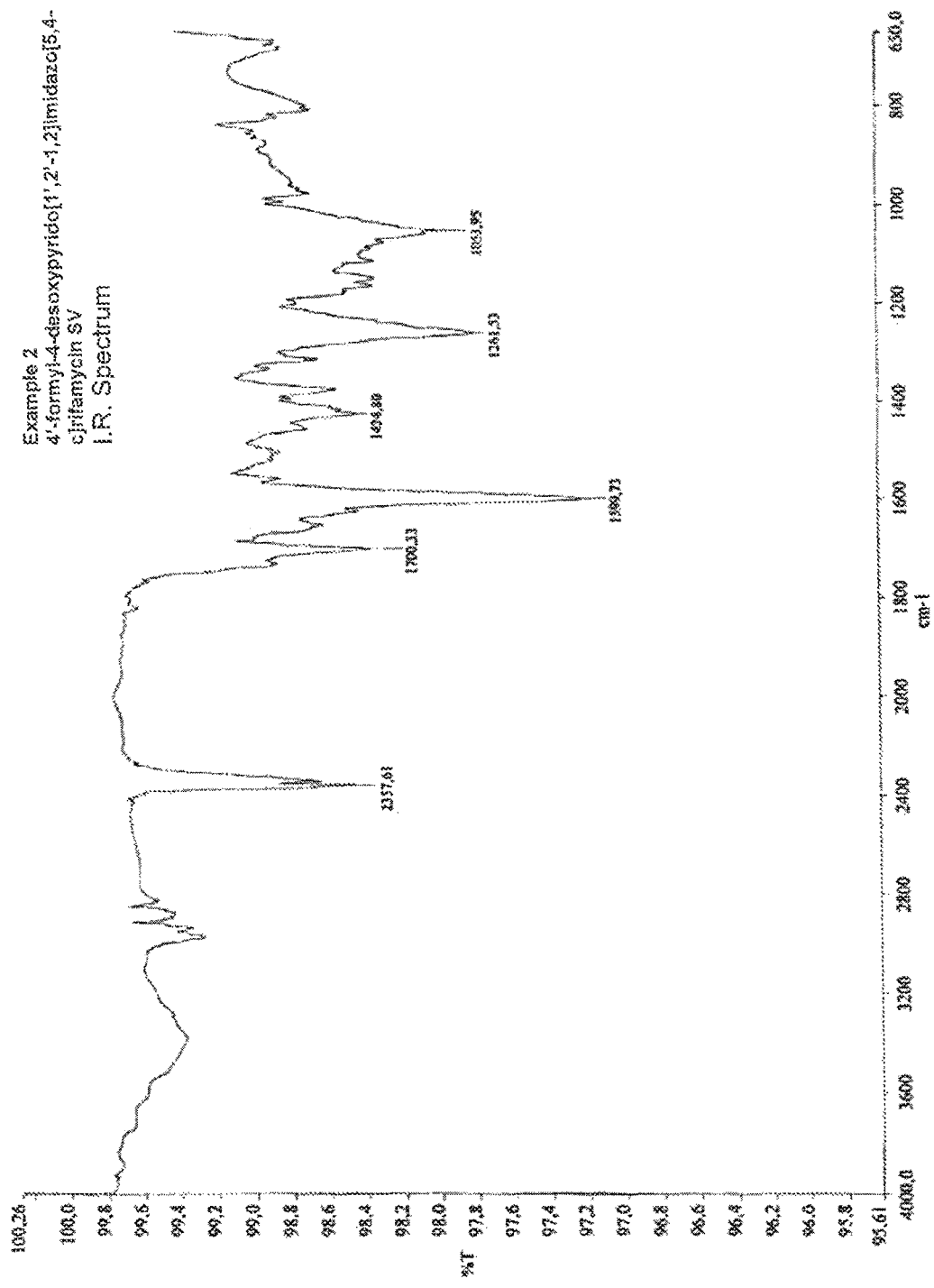
FIG. 10 shows the I.R. spectrum of the compound 4'-formyl-4-desoxypyrido[1',2'-1,2]imidazo[5,4-c]rifamycin SV obtained in the Example 2.
Figure 11:
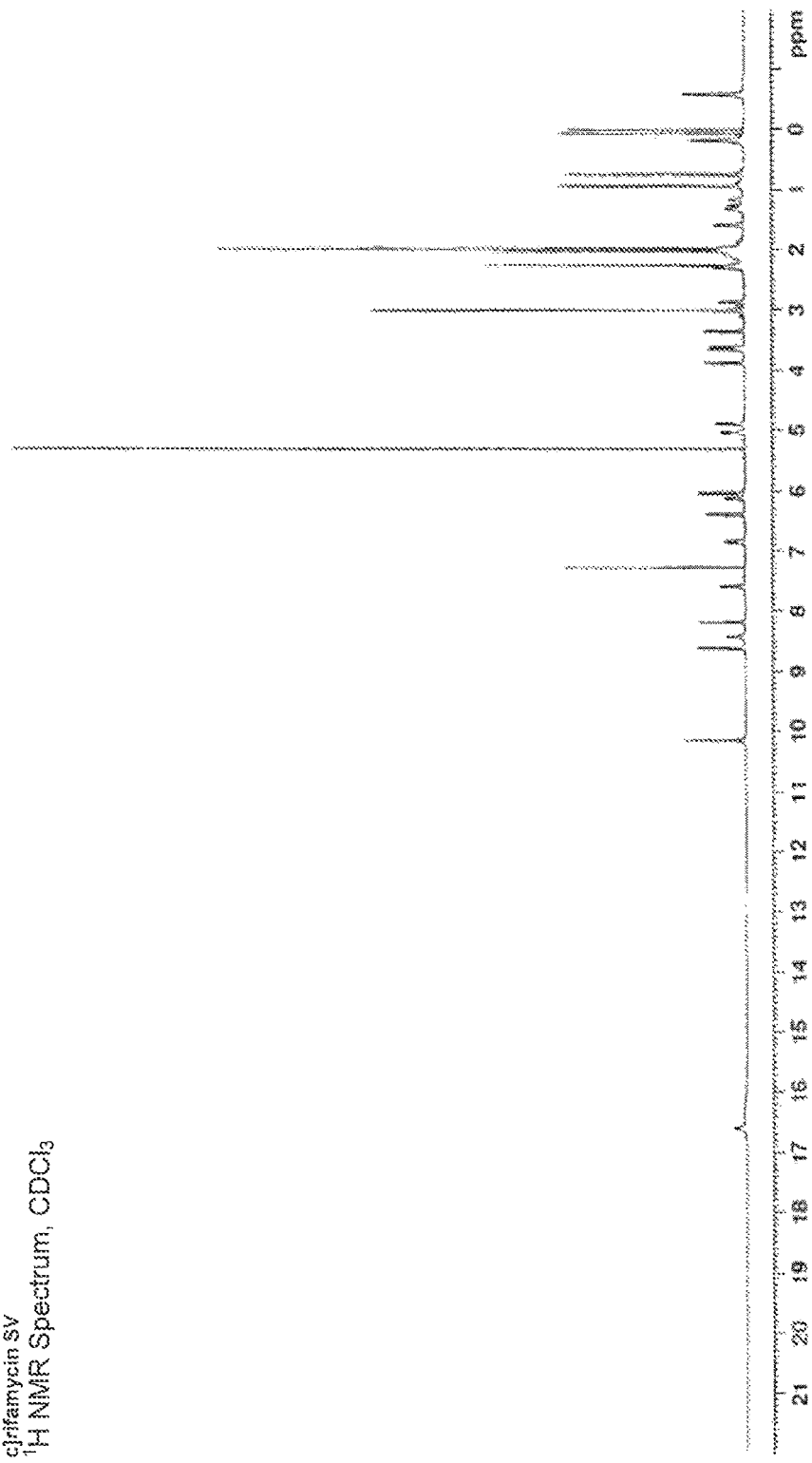
FIG. 11 shows the $^1$H NMR spectrum in CDCl$_3$ of the compound 4'-formyl-4-desoxypyrido[1',2'-1,2]imidazo[5,4-c]rifamycin SV obtained in the Example 2.
Figure 12:
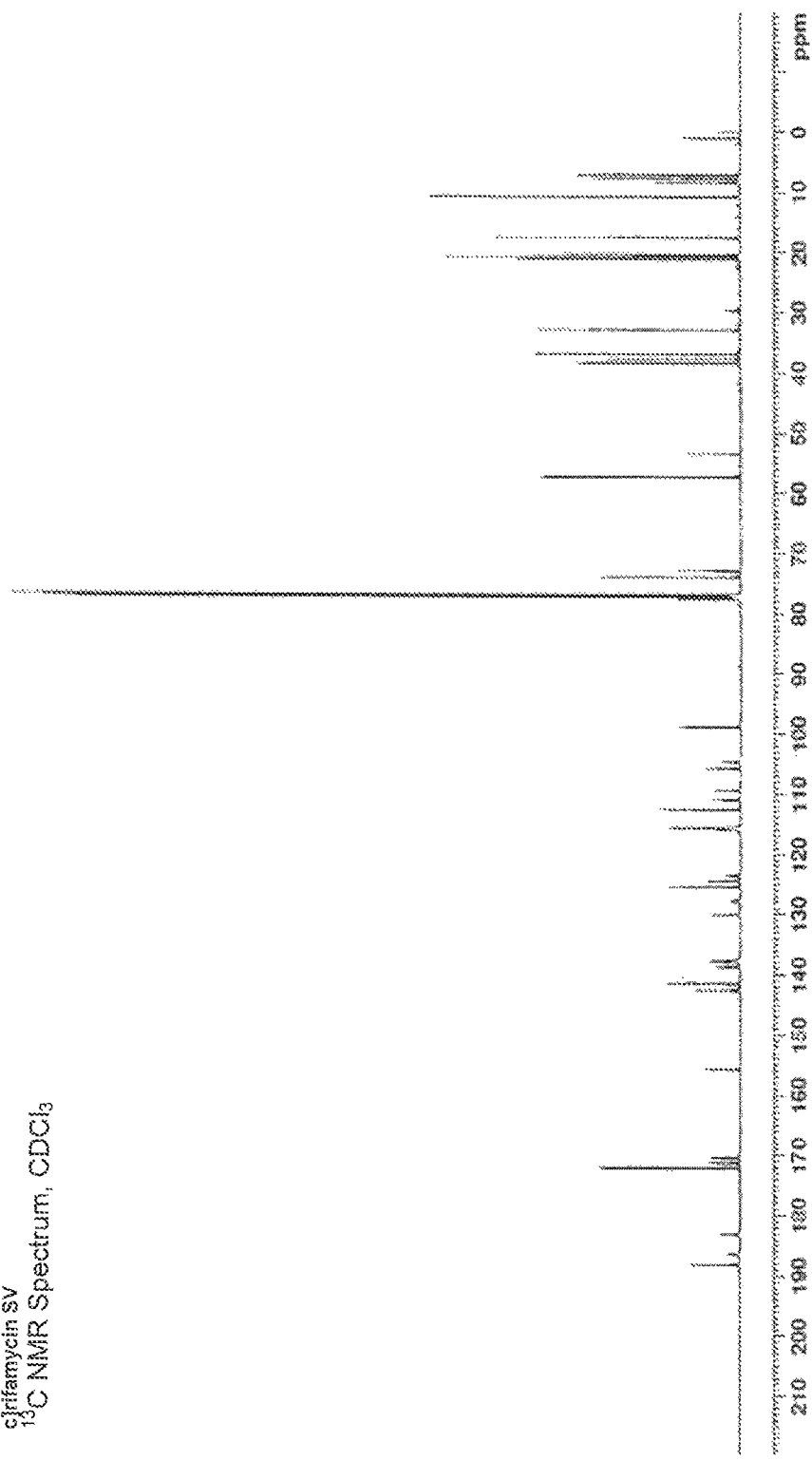
FIG. 12 shows the $^{13}$C NMR spectrum in CDCl$_3$ of the compound 4'-formyl-4-desoxypyrido[1',2'-1,2]imidazo[5,4-c]rifamycin SV obtained in the Example 2.
Figure 13:
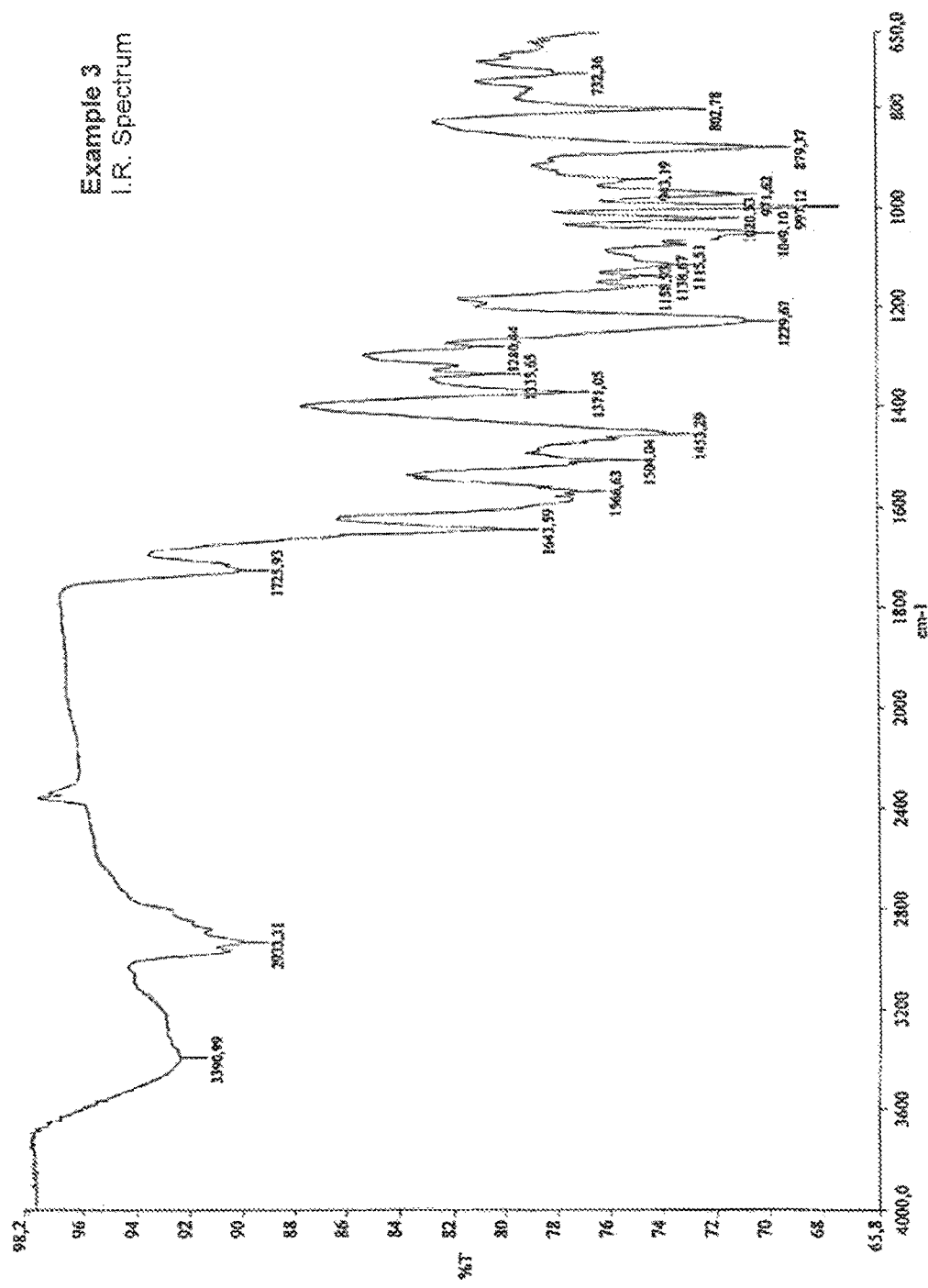
FIG. 13 shows the I.R. spectrum of the compound 4'-[(4-methyl-1-piperazinyl)iminomethyl]-4-desoxypyrido[1',2'-1,2]imidazo[5,4-c]rifamycin SV obtained in the Example 3.
Figure 14:
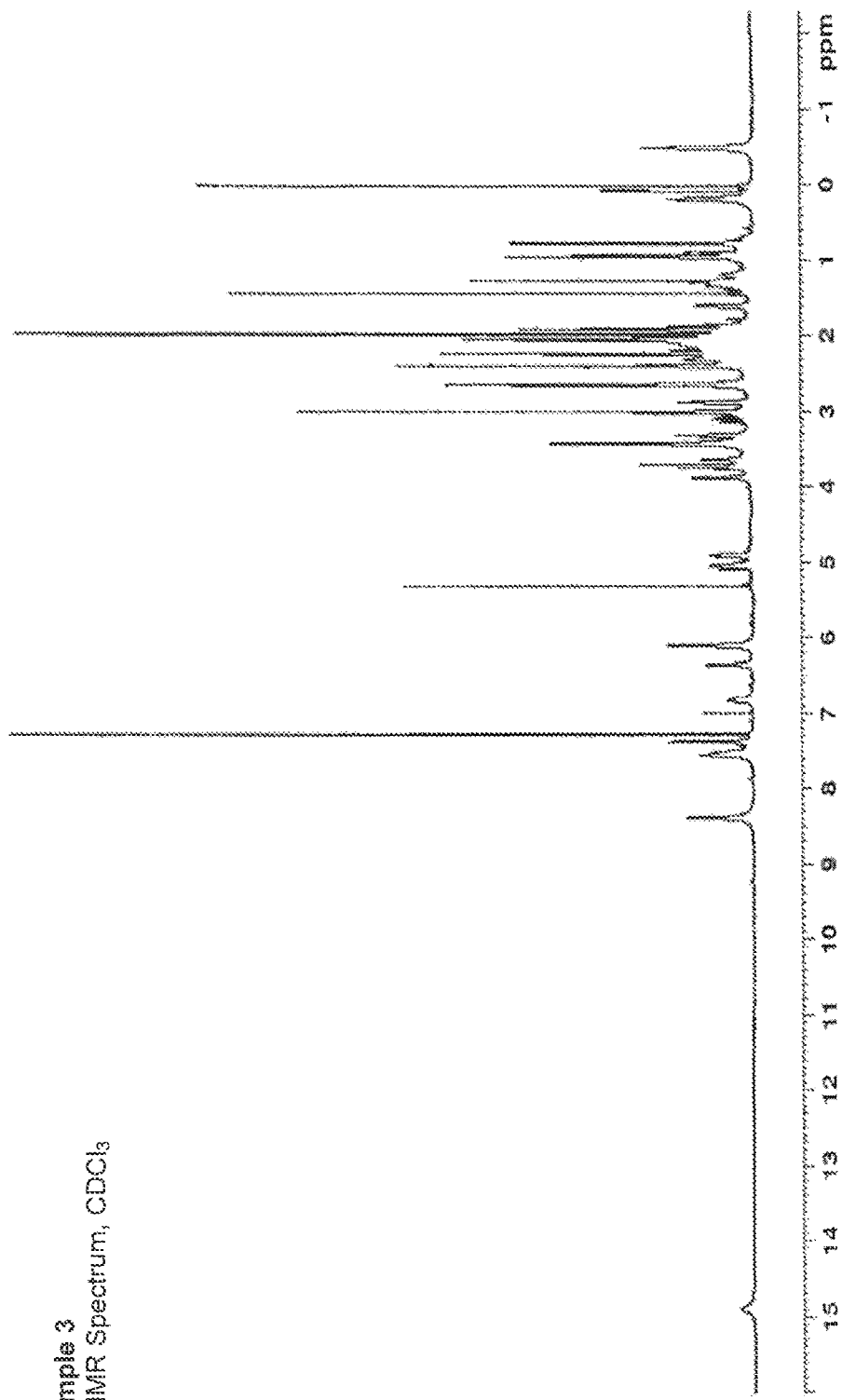
FIG. 14 shows the $^1$H NMR spectrum in CDCl$_3$ of the compound 4'-[(4-methyl-1-piperazinyl)iminomethyl]-4-desoxypyrido[1',2'-1,2]imidazo[5,4-c]rifamycin SV obtained in the Example 3.
Figure 15:
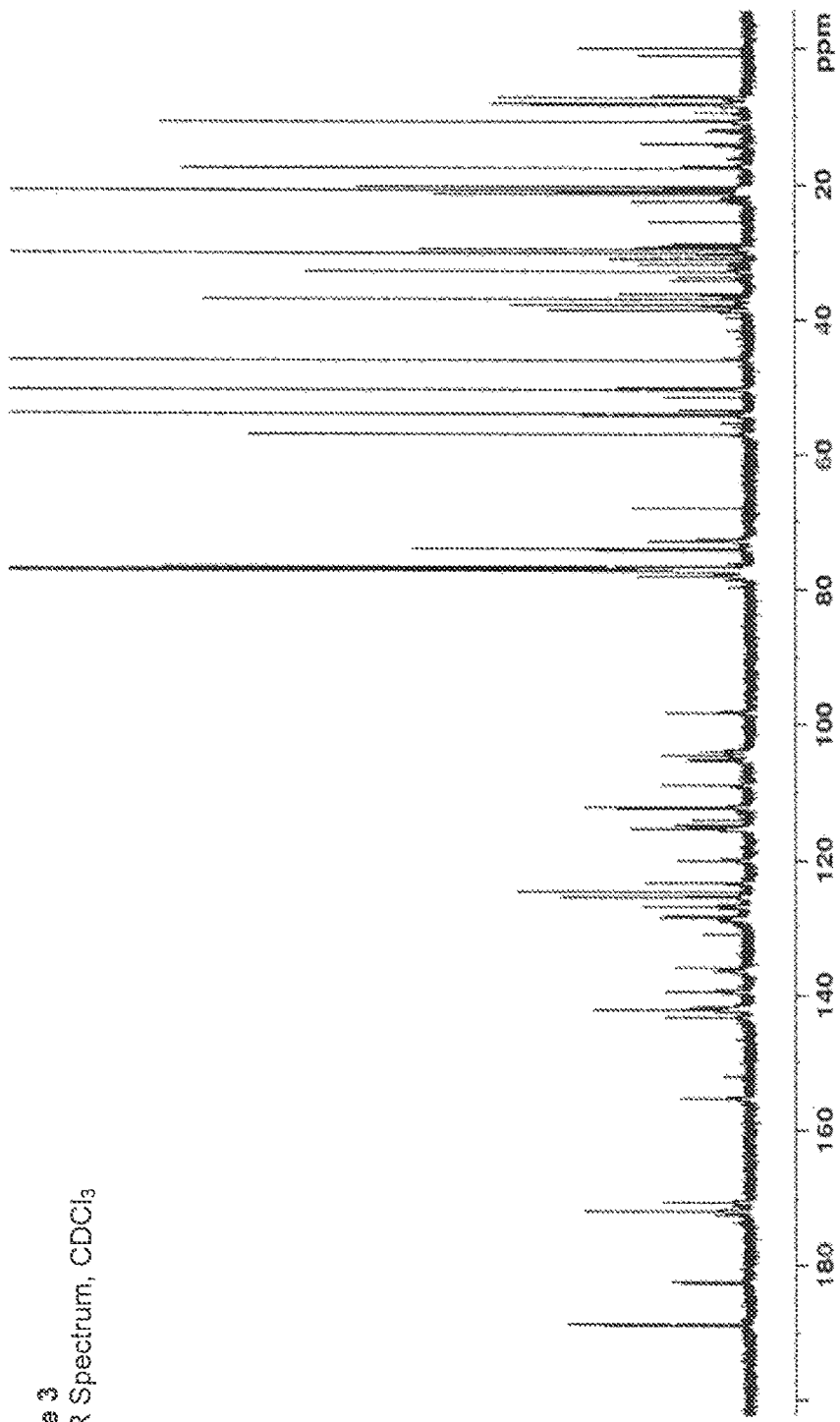
FIG. 15 shows the $^{13}$C NMR spectrum in CDCl$_3$ of the compound 4'-[(4-methyl-1-piperazinyl)iminomethyl]-4-desoxypyrido[1',2'-1,2]imidazo[5,4-c]rifamycin SV obtained in the Example 3.
Figure 16:
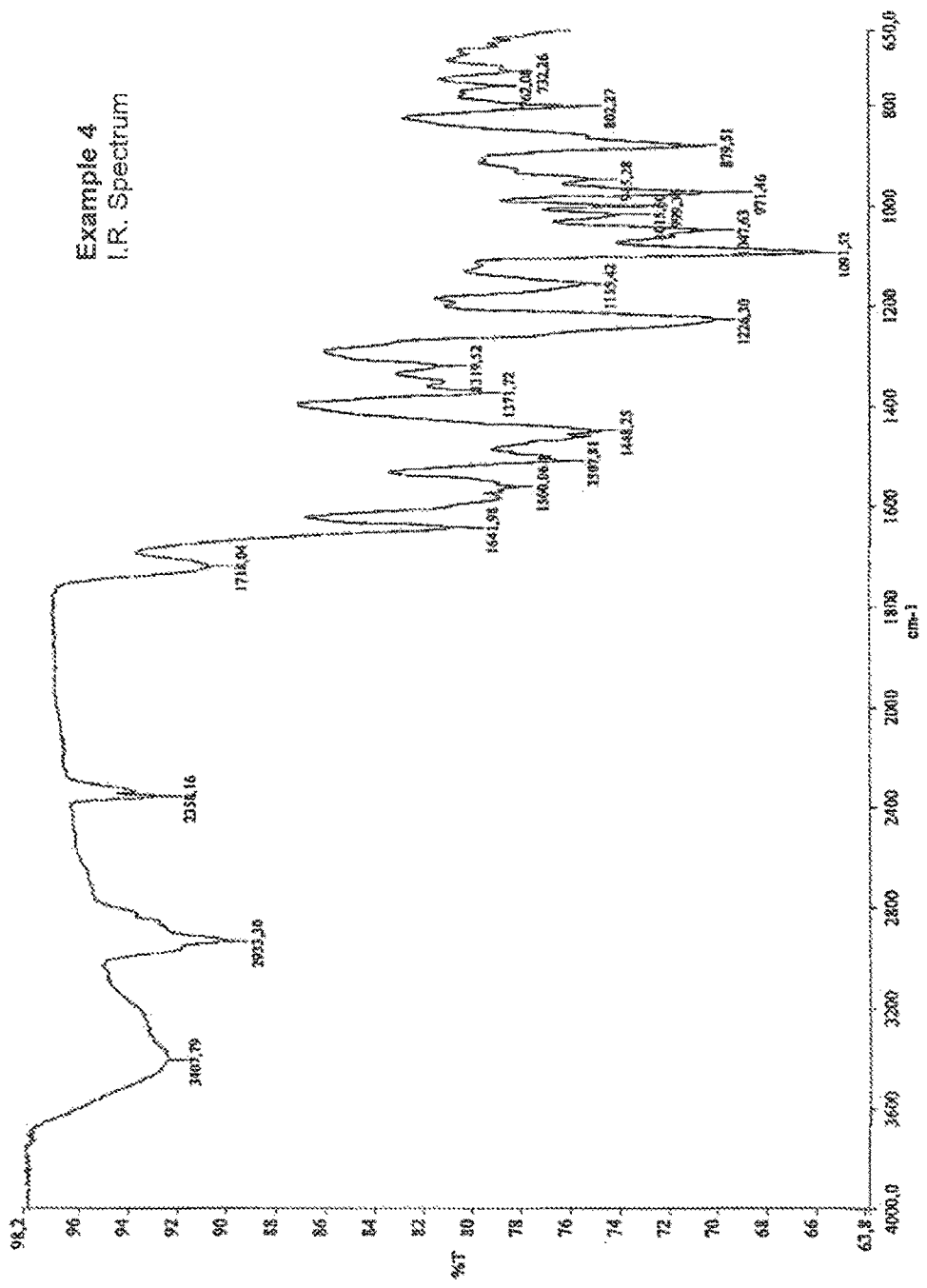
FIG. 16 shows the I.R. spectrum of the compound 4'-[(1-piperidinyl)iminomethyl]-4-desoxypyrido[1',2'-1,2]imidazo[5,4-c]rifamycin SV obtained in the Example 4.
Figure 17:
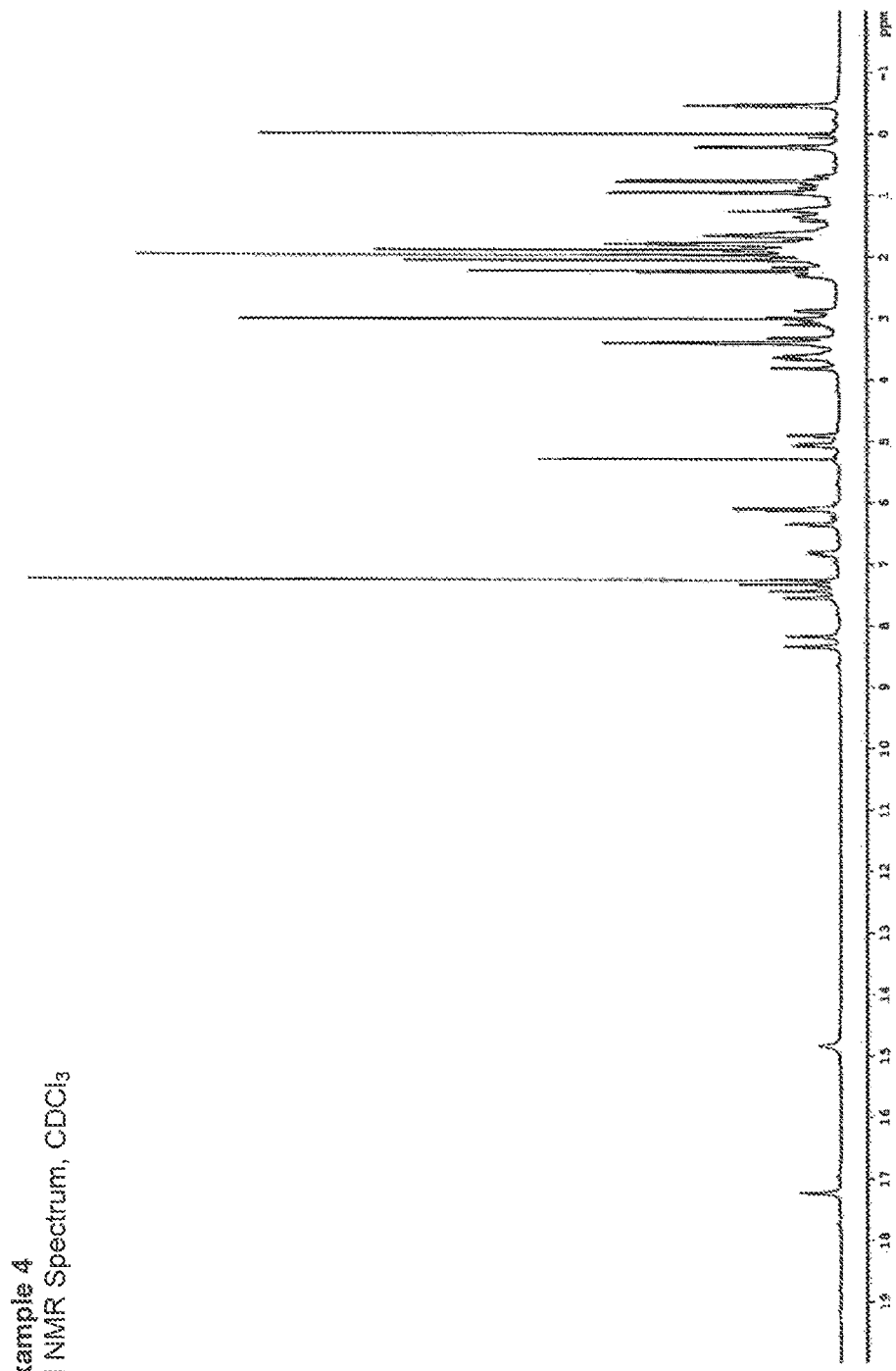
FIG. 17 shows the $^1$H NMR spectrum in CDCl$_3$ of the compound 4'-[(1-piperidinyl)iminomethyl]-4-desoxypyrido[1',2'-1,2]imidazo[5,4-c]rifamycin SV obtained in the Example 4.
Figure 18:
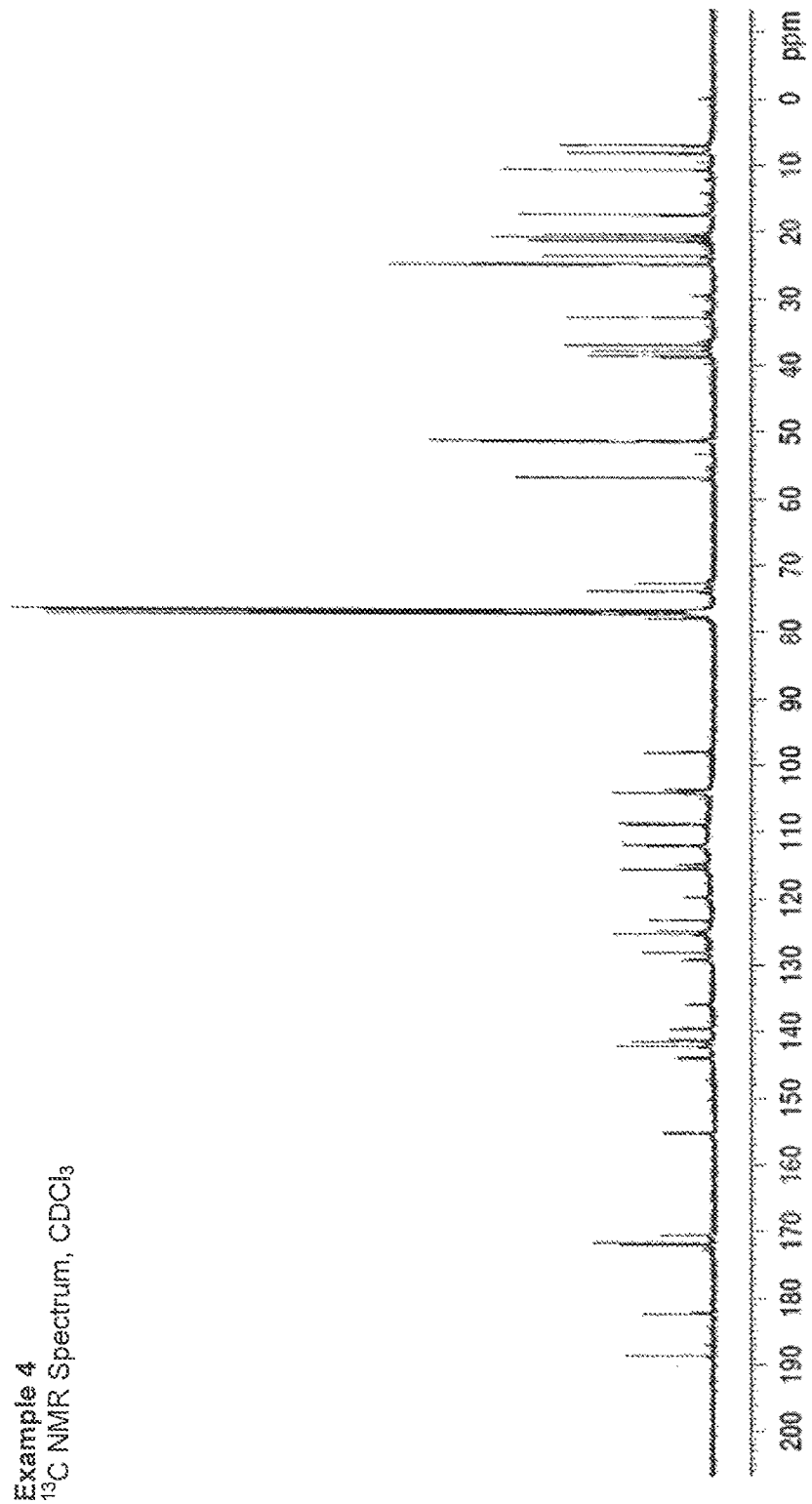
FIG. 18 shows the $^{13}$C NMR spectrum in CDCl$_3$ of the compound 4'-[(1-piperidinyl)iminomethyl]-4-desoxypyrido[1',2'-1,2]imidazo[5,4-c]rifamycin SV obtained in the Example 4.
Figure 19:
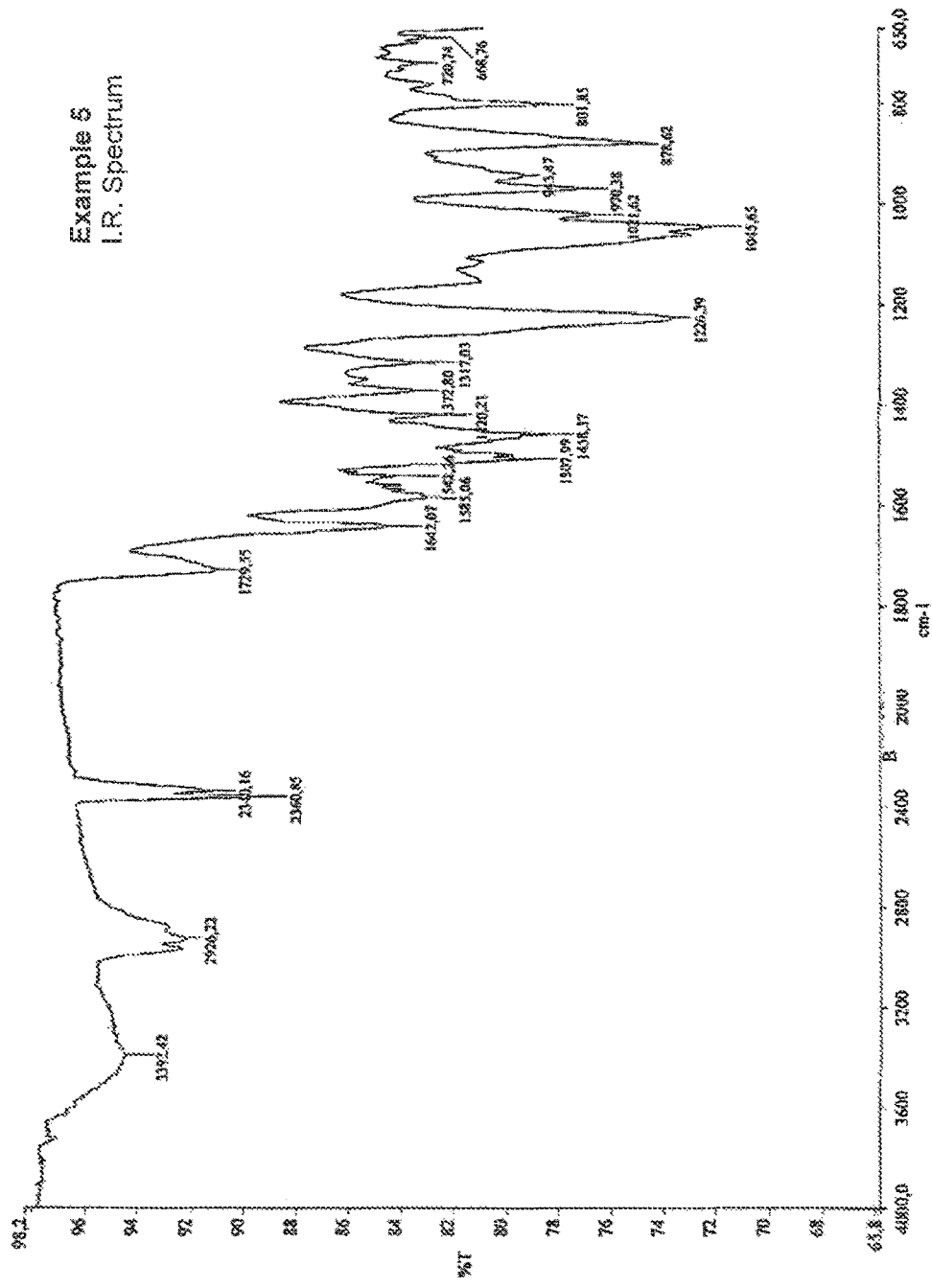
FIG. 19 shows the I.R. spectrum of the compound 4'-[(N,N-dimethylamino)iminomethyl]-4-desoxypyrido[1',2'-1,2]imidazo[5,4-c]rifamycin SV obtained in the Example 5.
Figure 20:
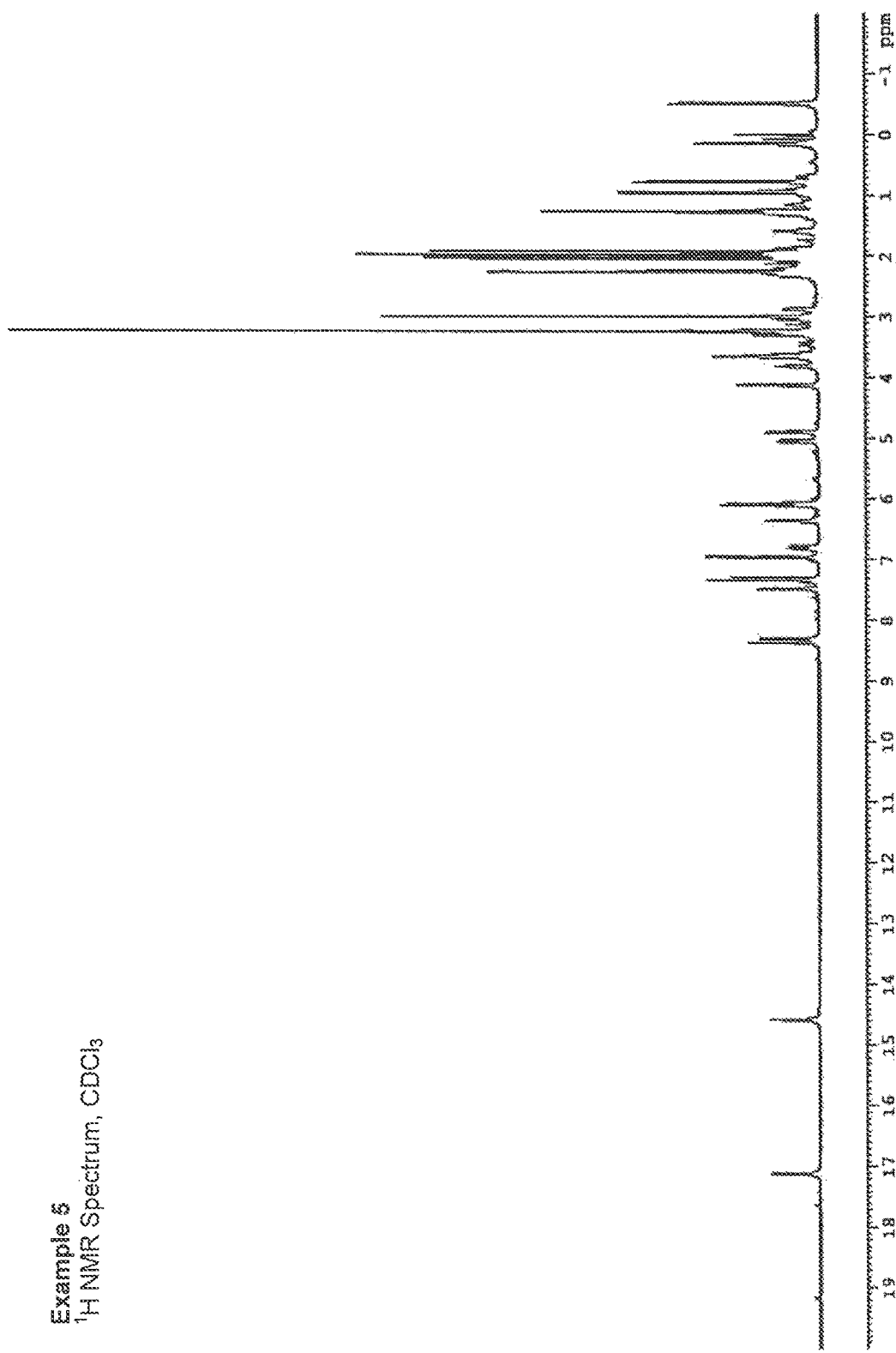
FIG. 20 shows the $^1$H NMR spectrum in CDCl$_3$ of the compound 4'-[(N,N-dimethylamino)iminomethyl]-4-desoxypyrido[1',2'-1,2]imidazo[5,4-c]rifamycin SV obtained in the Example 5.
Figure 21:
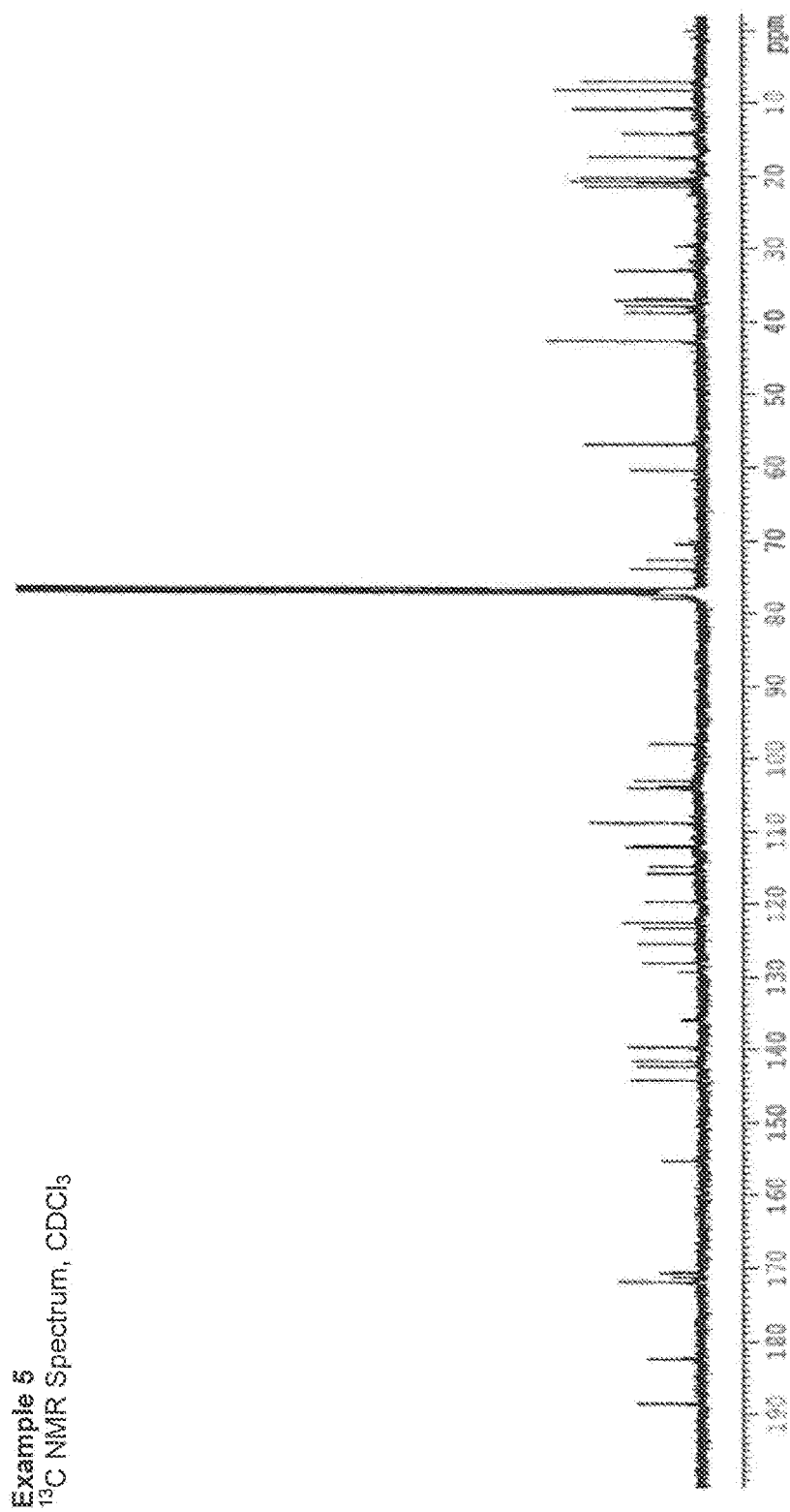
FIG. 21 shows the $^{13}$C NMR spectrum in CDCl$_3$ of the compound 4'-[(N,N-dimethylamino)iminomethyl]-4-desoxypyrido[1',2'-1,2]imidazo[5,4-c]rifamycin SV obtained in the Example 5.
Figure 22:
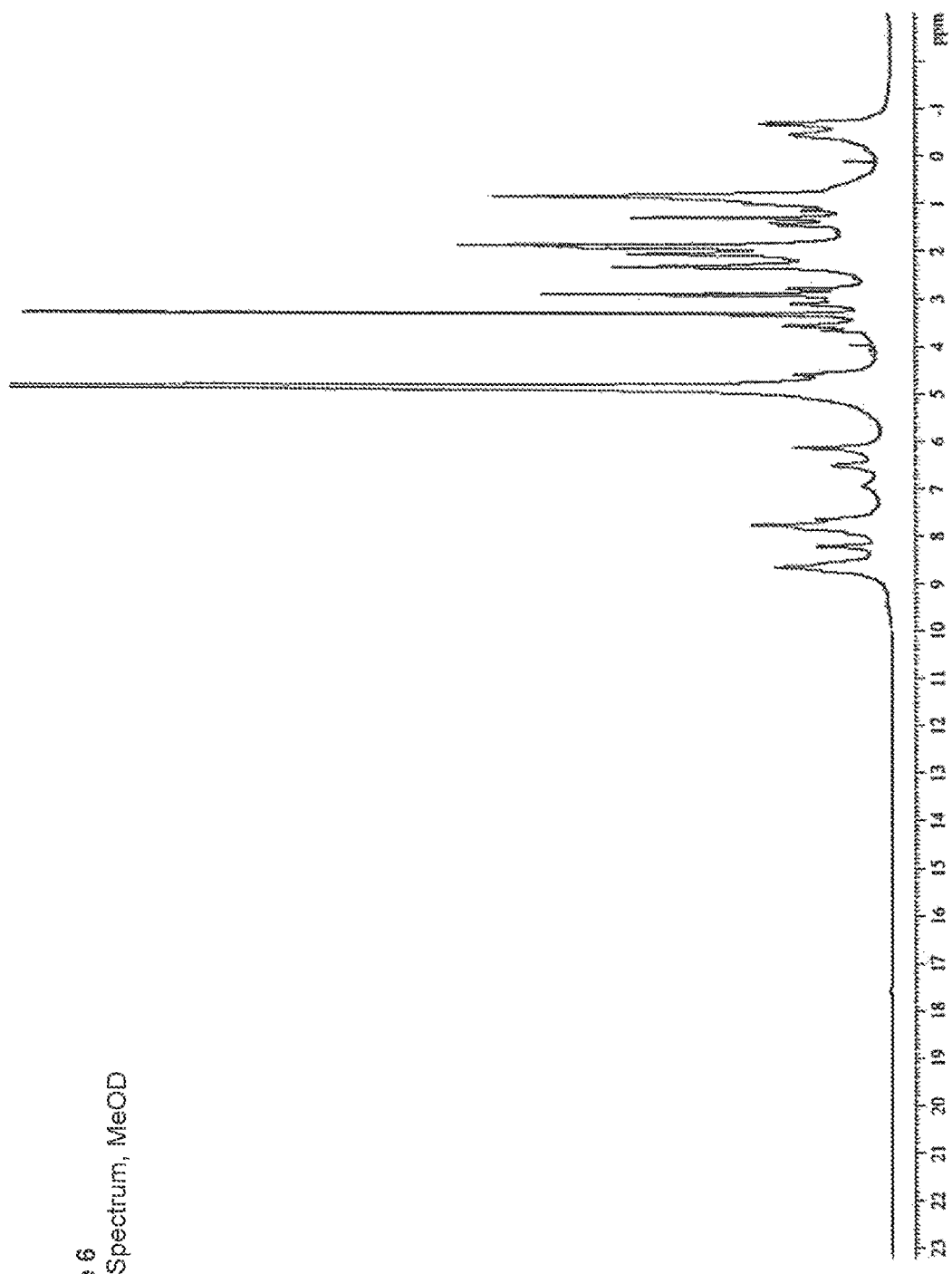
FIG. 22 shows the $^1$H NMR spectrum in MeOD of the compound 4'-[(4-carboxyamidopyridyl)iminomethyl]-4-desoxypyrido[1',2'-1,2]imidazo[5,4-c]rifamycin SV obtained in the Example 6.
Figure 23:
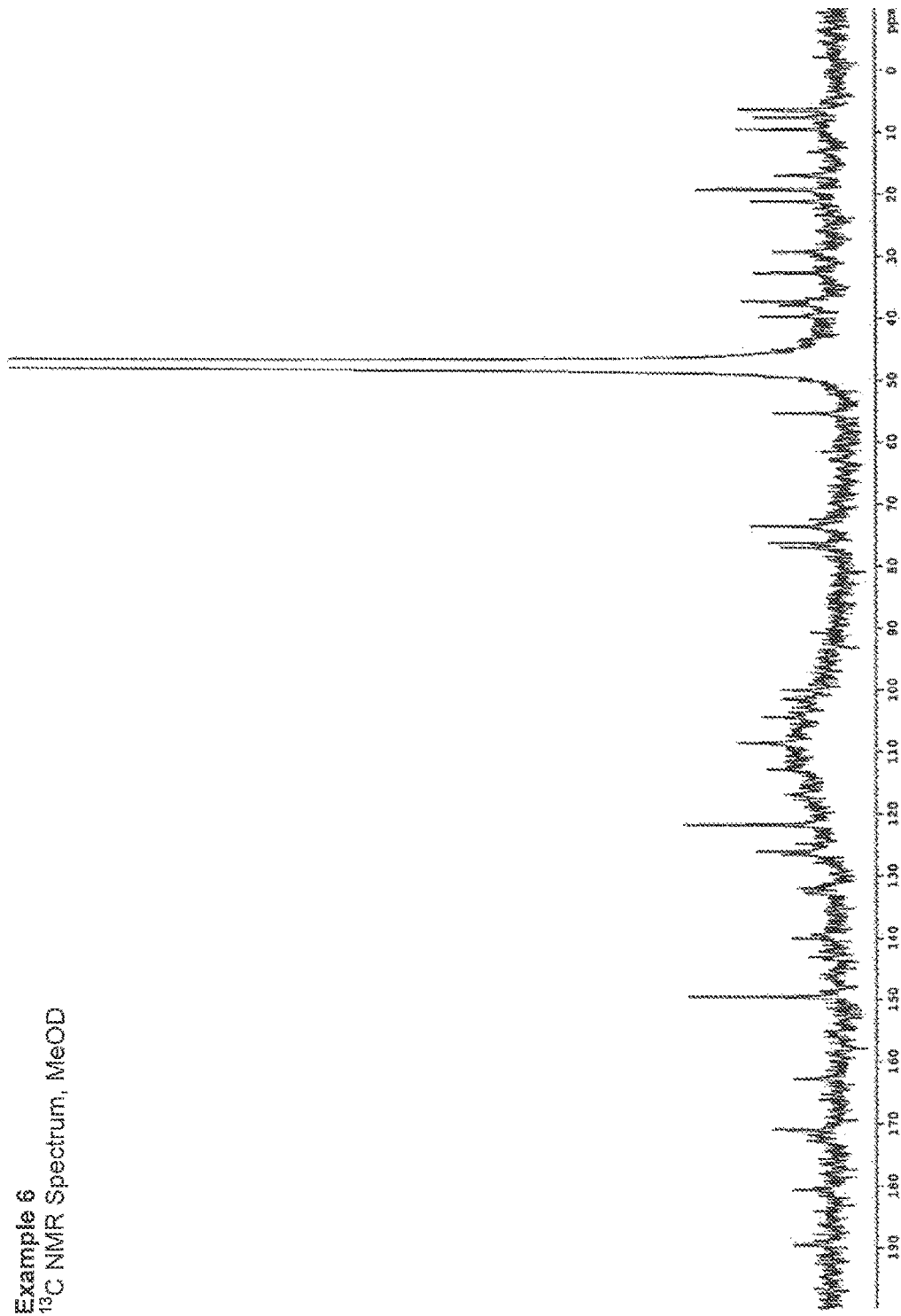
FIG. 23 shows the $^{13}$C NMR spectrum in MeOD of the compound 4'-[(4-carboxyamidopyridyl)iminomethyl]-4-desoxypyrido[1',2'-1,2]imidazo[5,4-c]rifamycin SV obtained in the Example 6.
Figure 24:
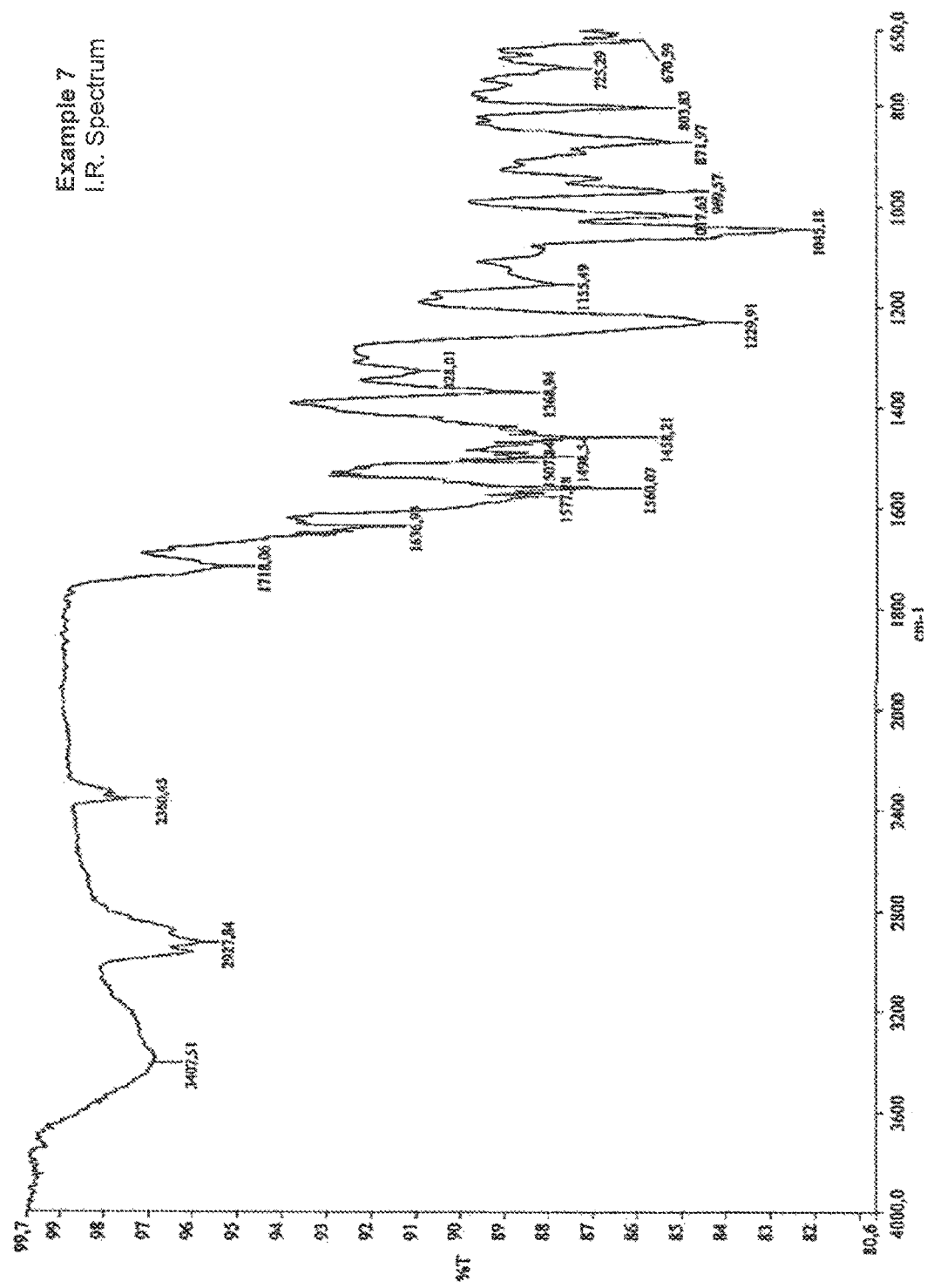
FIG. 24 shows the I.R. spectrum of the compound 5'-[(N,N-dimethylamino)iminomethyl]-4-desoxypyrido[1',2'-1,2]imidazo[5,4-c]rifamycin SV obtained in the Example 7.
Figure 25:
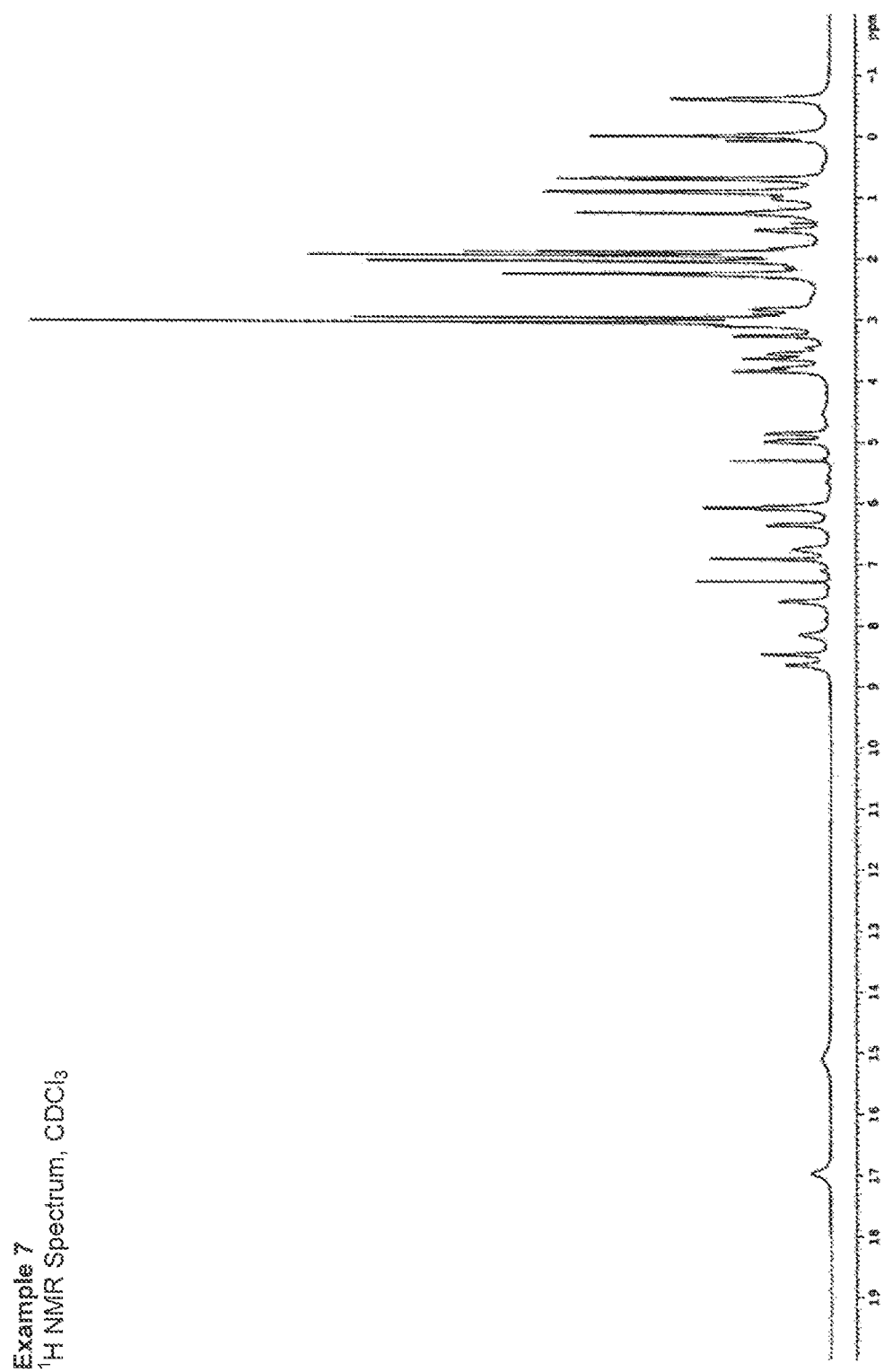
FIG. 25 shows the $^1$H NMR spectrum in CDCl$_3$ of the compound 5'-[(N,N-dimethylamino)iminomethyl]-4-desoxypyrido[1',2'-1,2]imidazo[5,4-c]rifamycin SV obtained in the Example 7.
Figure 26:
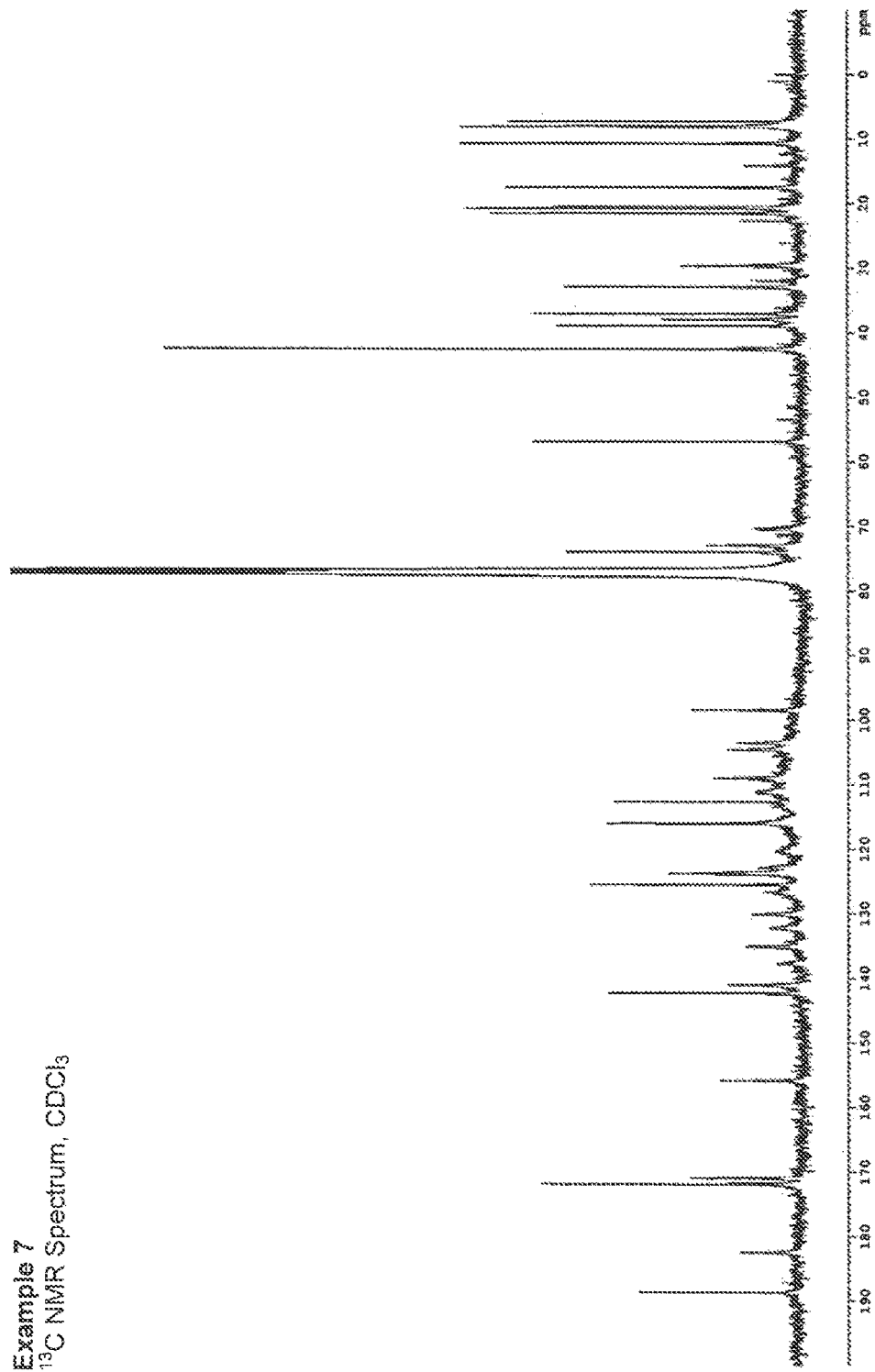
FIG. 26 shows the $^{13}$C NMR spectrum in CDCl$_3$ of the compound 5'-[(N,N-dimethylamino)iminomethyl]-4-desoxypyrido[1',2'-1,2]imidazo[5,4-c]rifamycin SV obtained in the Example 7.
Figure 27:
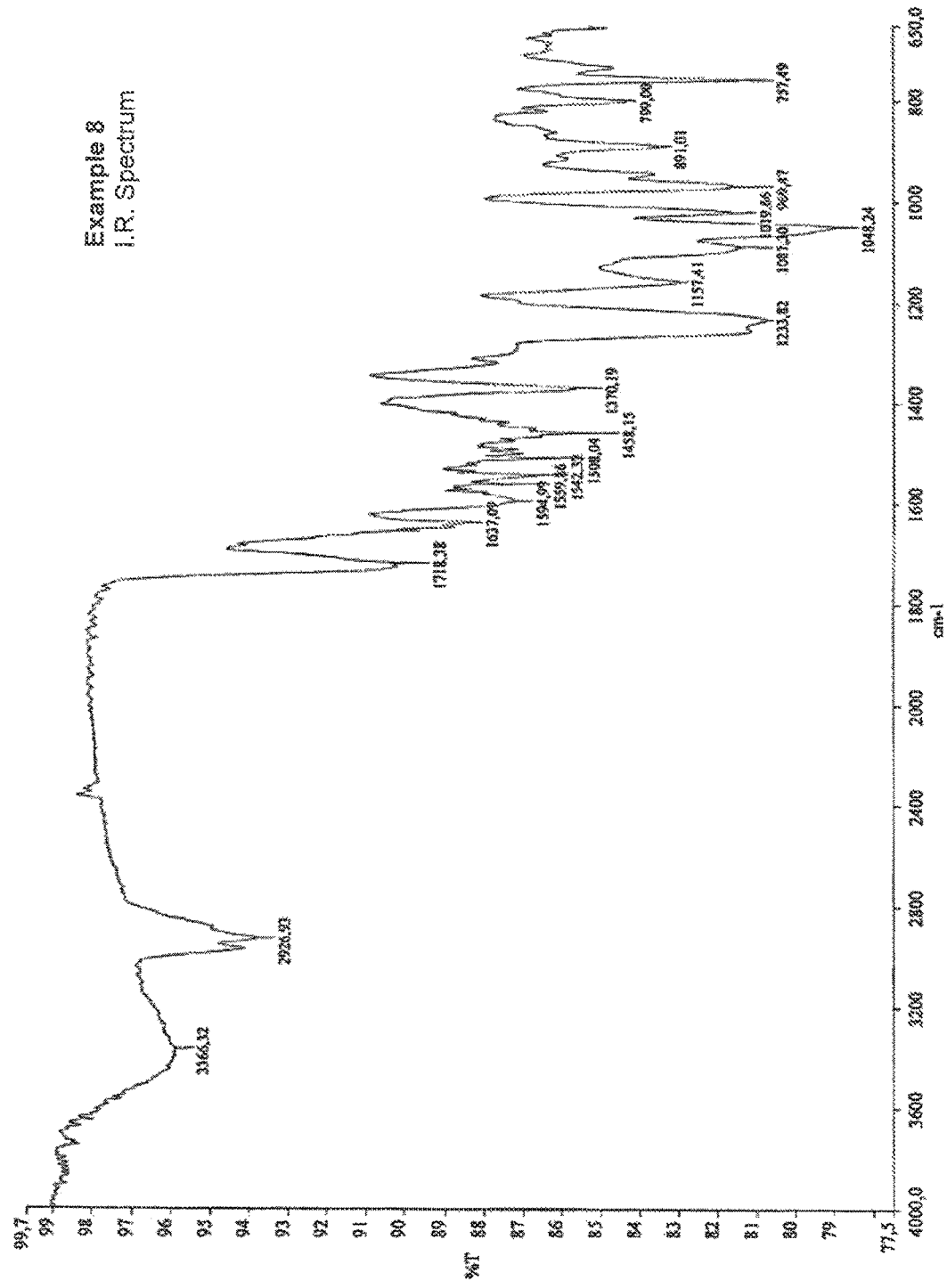
FIG. 27 shows the I.R. spectrum of the compound 5'-[(1-piperidinyl)iminomethyl]-4-desoxypyrido[1',2'-1,2]imidazo[5,4-c]rifamycin SV obtained in the Example 8.
Figure 28:
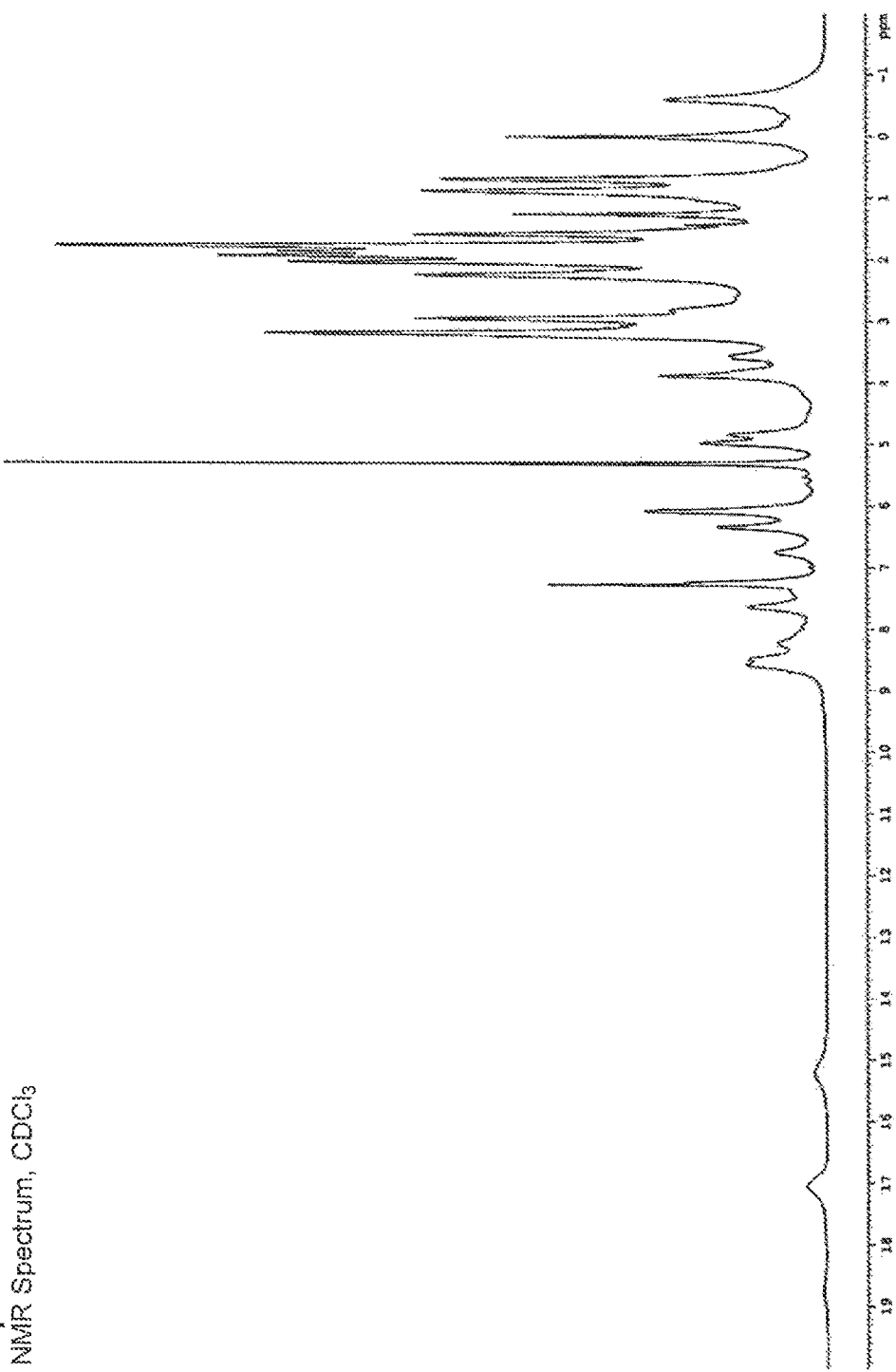
FIG. 28 shows the $^1$H NMR spectrum in CDCl$_3$ of the compound 5'-[(1-piperidinyl)iminomethyl]-4-desoxypyrido[1',2'-1,2]imidazo[5,4-c]rifamycin SV obtained in the Example 8.
Figure 29:
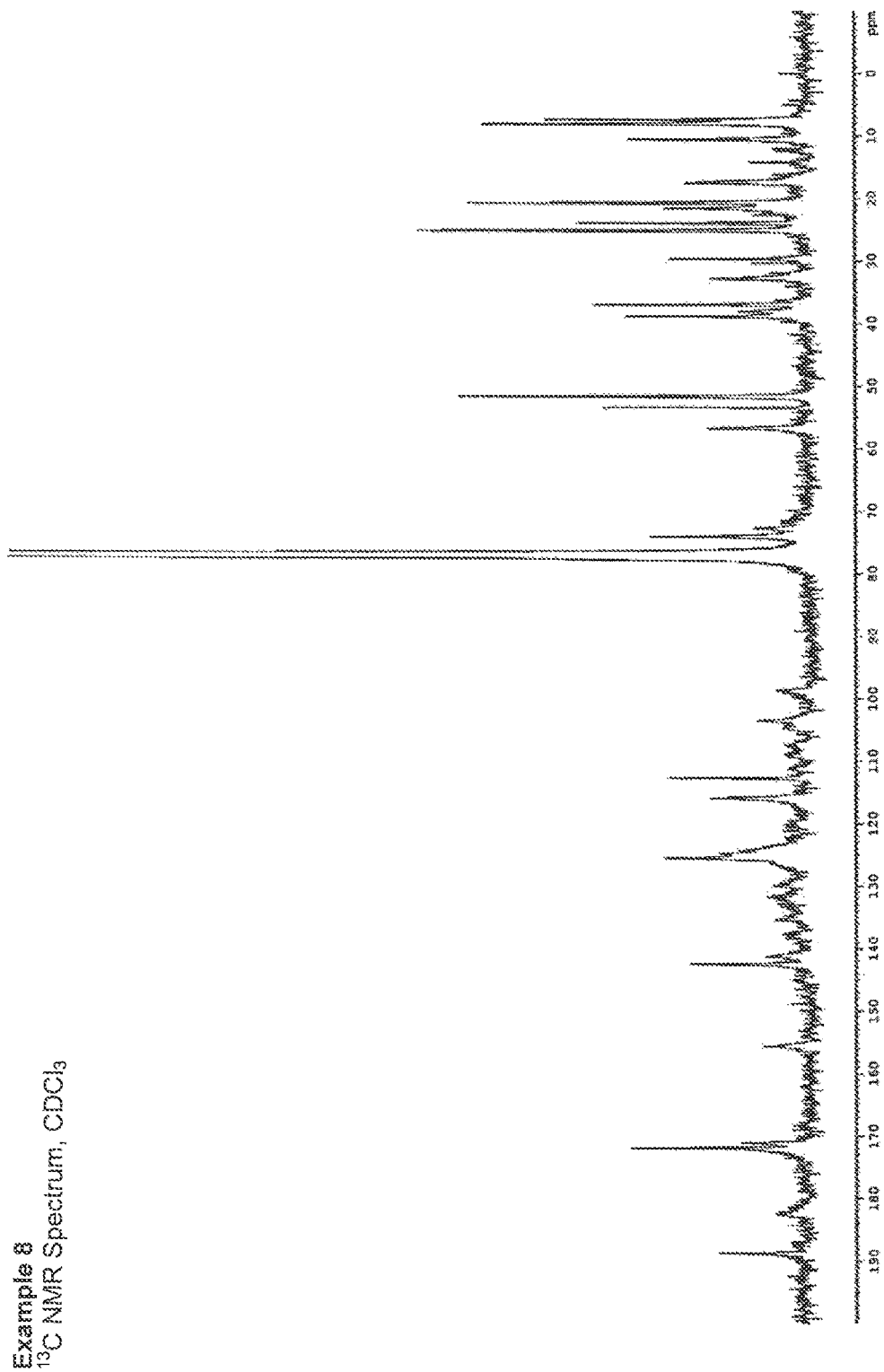
FIG. 29 shows the $^{13}$C NMR spectrum in CDCl$_3$ of the compound 5'-[(1-piperidinyl)iminomethyl]-4-desoxypyrido[1',2'-1,2]imidazo[5,4-c]rifamycin SV obtained in the Example 8.
Figure 30:
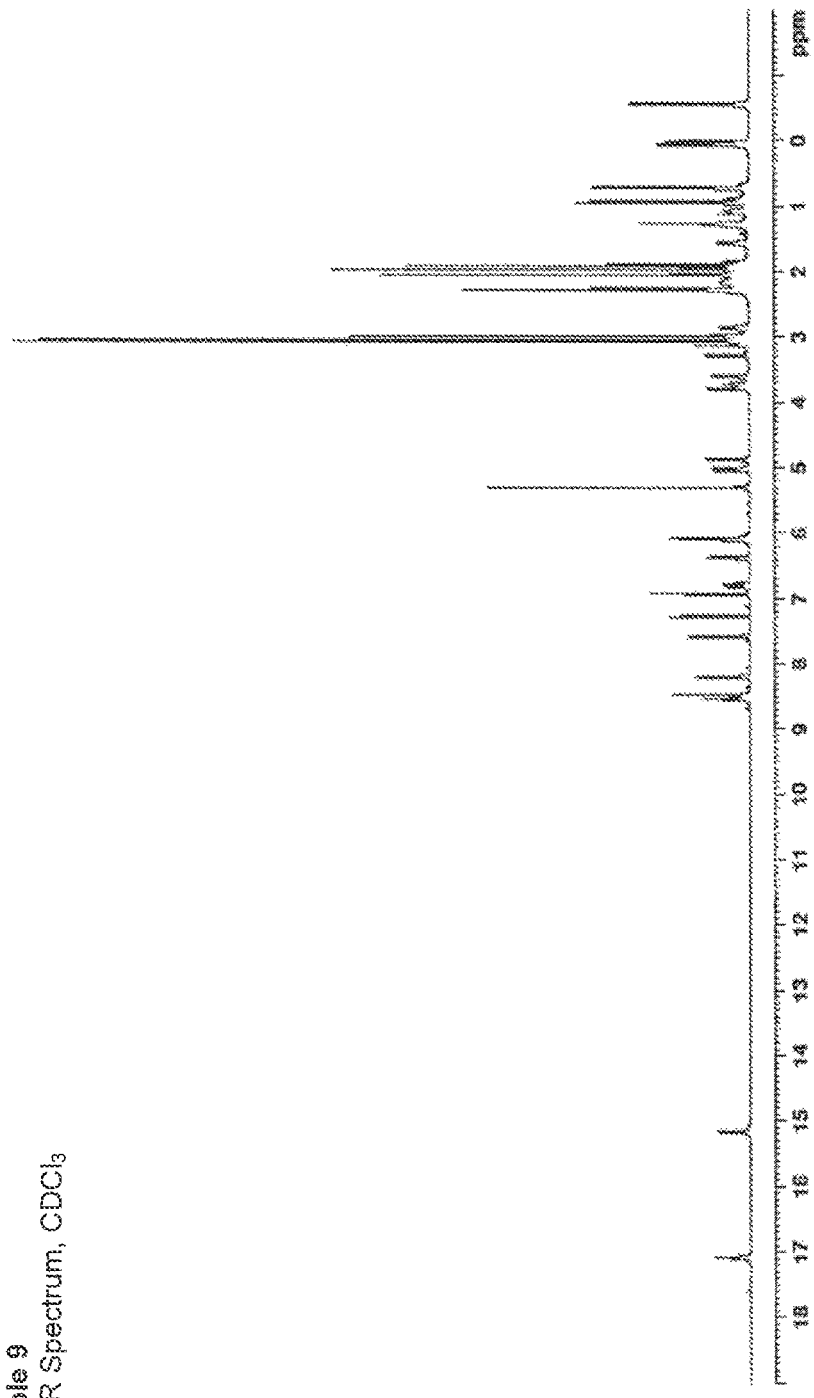
FIG. 30 shows the $^1$H NMR spectrum in CDCl$_3$ of the compound 5'-[(N,N-dimethylamino)iminomethyl]-4-desoxypyrido[1',2'-1,2]imidazo[5,4-c]rifamycin SV obtained in the Example 9.
Figure 31:
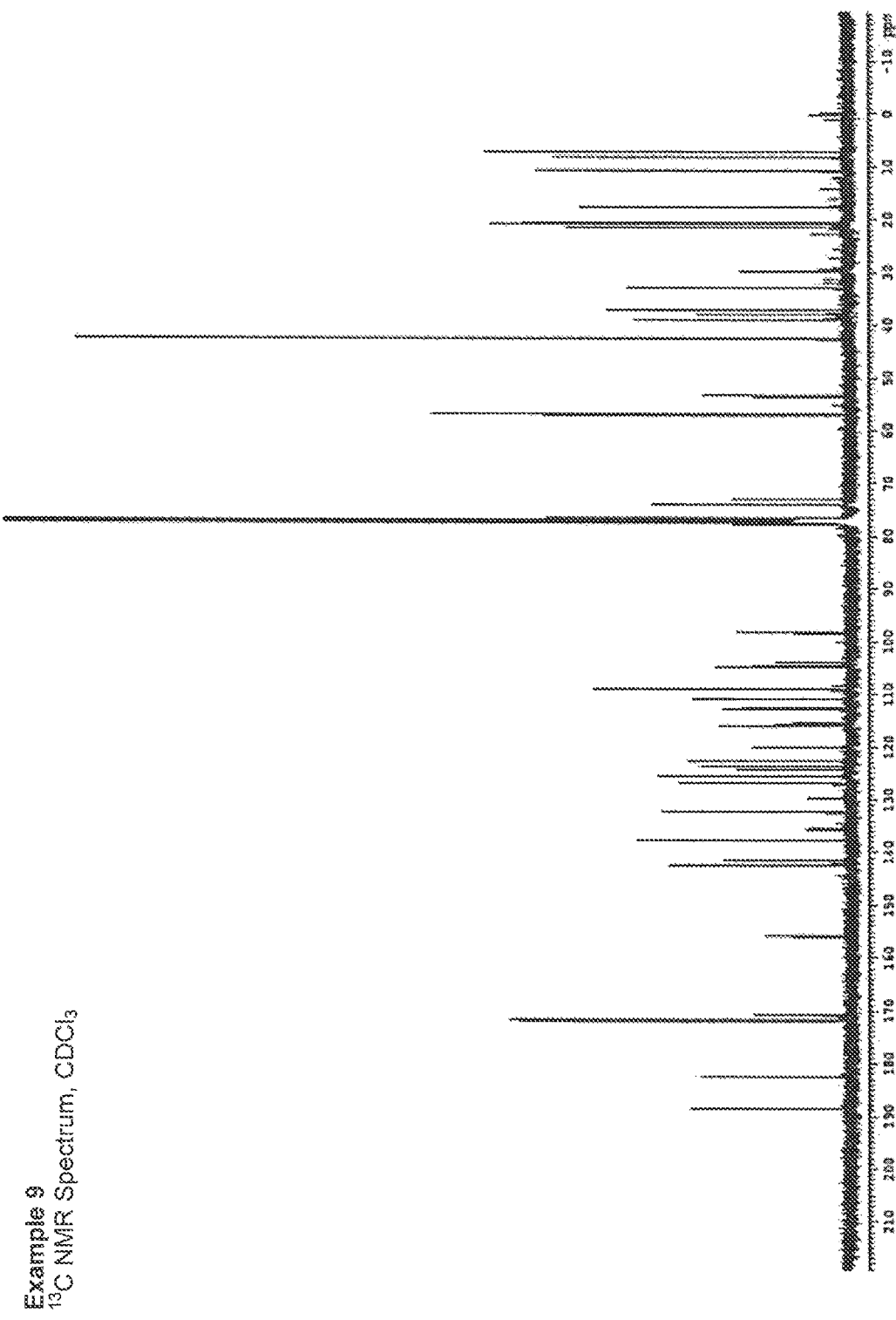
FIG. 31 shows the $^{13}$C NMR spectrum in CDCl$_3$ of the compound 5'-[(N,N-dimethylamino)iminomethyl]-4-desoxypyrido[1',2'-1,2]imidazo[5,4-c]rifamycin SV obtained in the Example 9.
Figure 32:
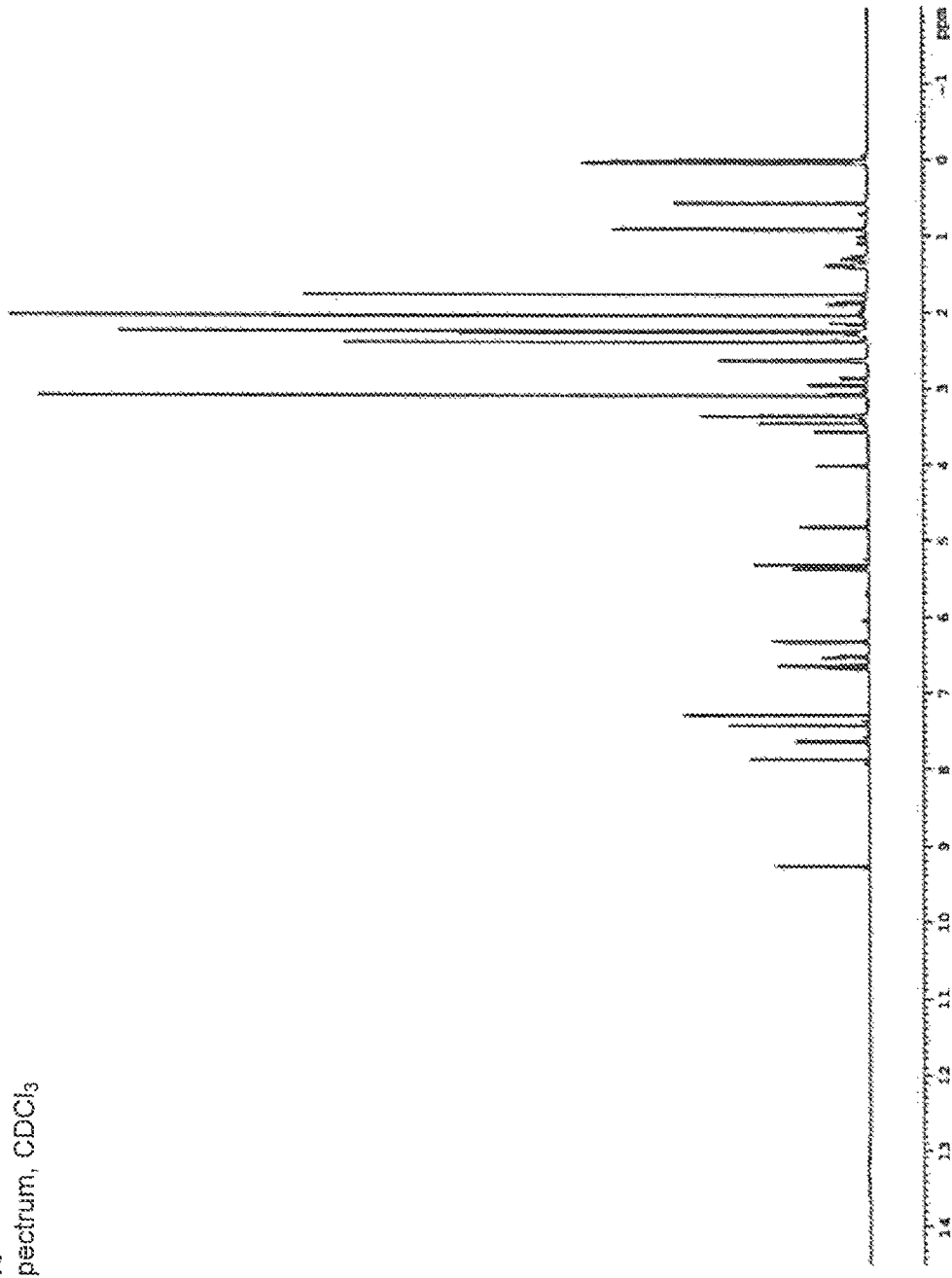
FIG. 32 shows the $^1$H NMR spectrum in CDCl$_3$ of the compound 4'-[(4-methyl-1-piperazinyl)iminomethyl]-4-desoxypyrido[1',2'-1,2]imidazo[5,4-c]rifamycin S obtained in the Example 10.
Figure 33:
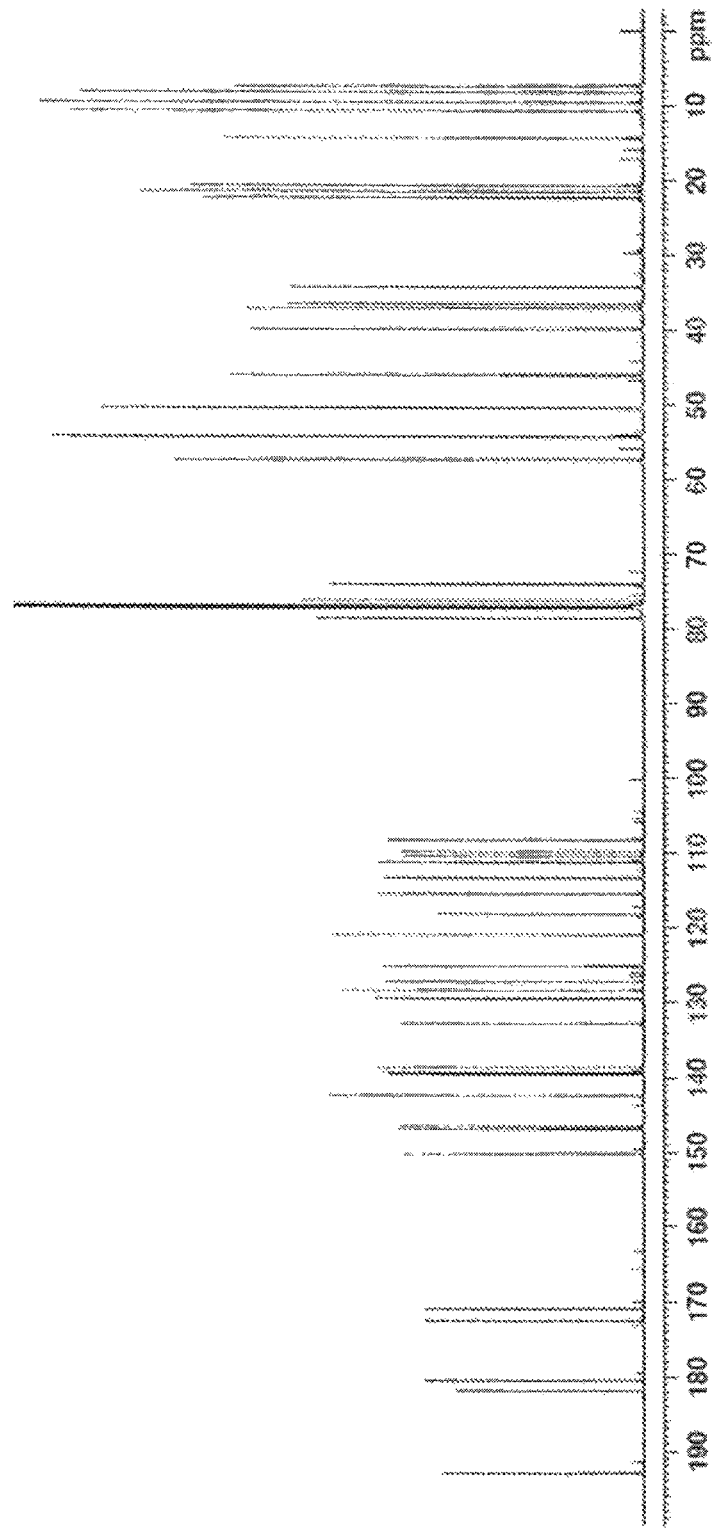
FIG. 33 shows the $^{13}$C NMR spectrum in CDCl$_3$ of the compound 4'-[(4-methyl-1-piperazinyl)iminomethyl]-4-desoxypyrido[1',2'-1,2]imidazo[5,4-c]rifamycin S obtained in the Example 10.
Figure 34:
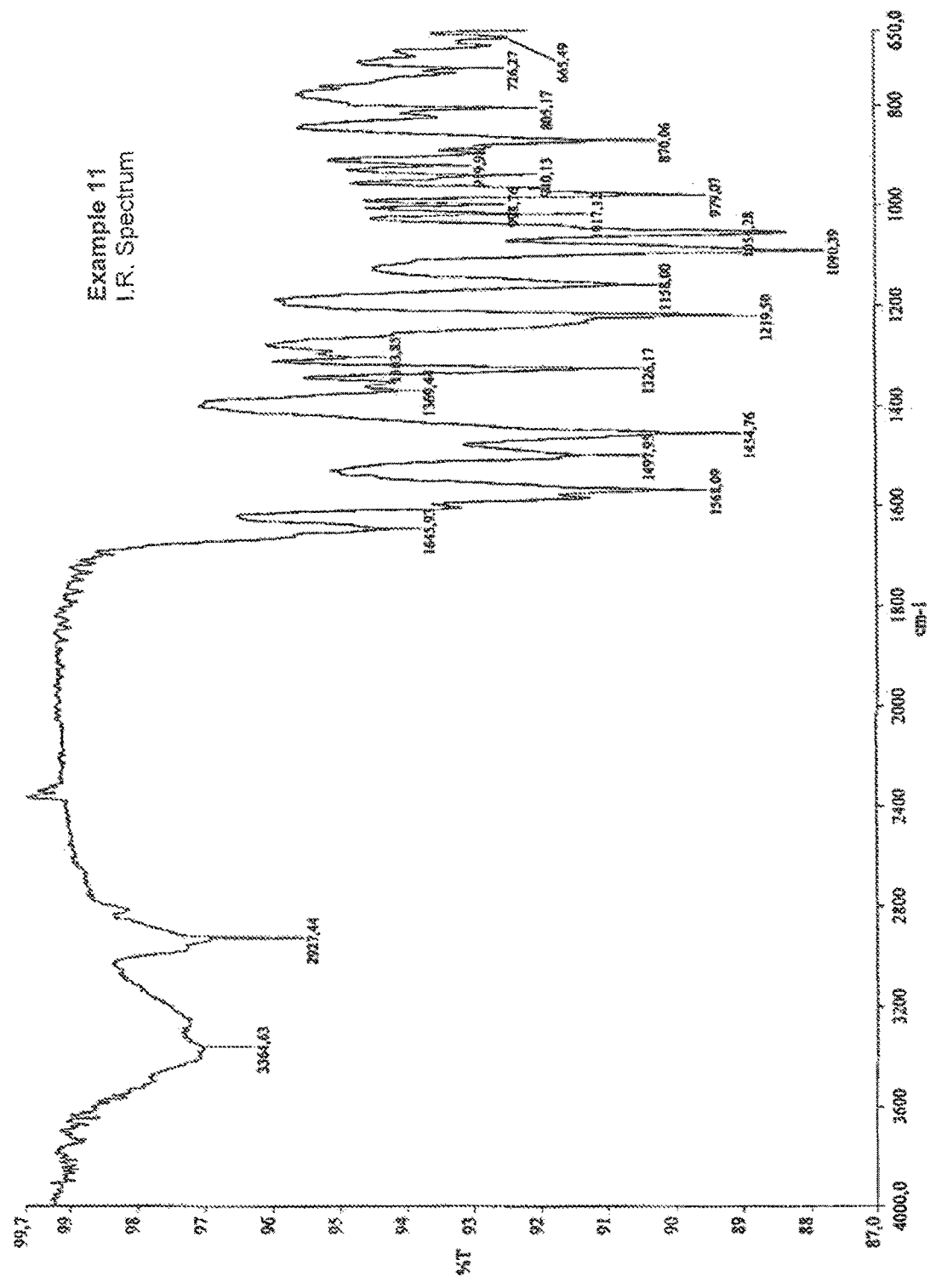
FIG. 34 shows the I.R. spectrum of the compound 25-desacetyl-5'-[(1-piperidinyl)iminomethyl]-4-desoxypyrido[1',2'-1,2]imidazo[5,4-c]rifamycin SV obtained in the Example 11.
Figure 35:
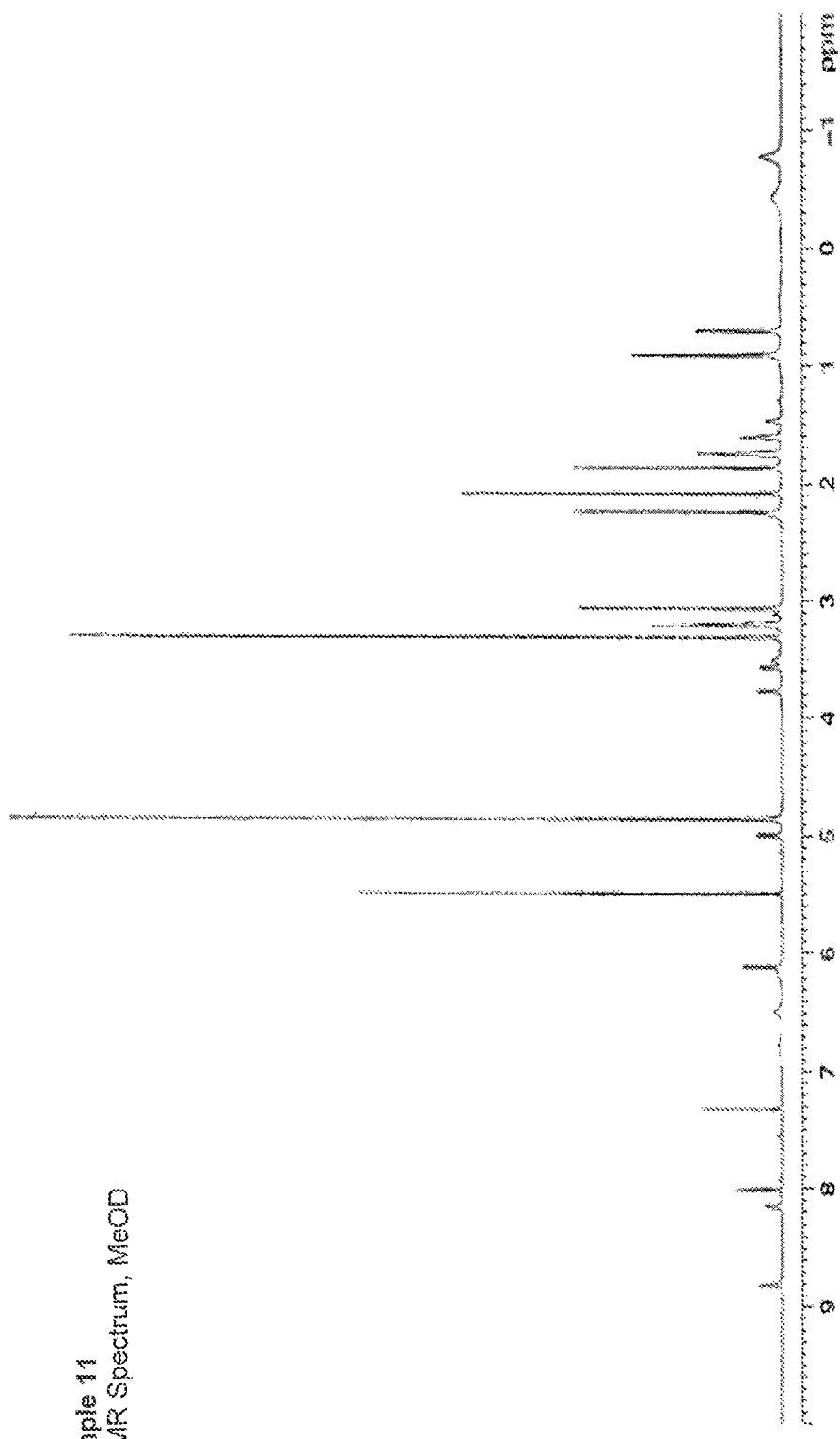
FIG. 35 shows the $^1$H NMR spectrum in MeOD of the compound 25-desacetyl-5'-[(1-piperidinyl)iminomethyl]-4-desoxypyrido[1',2'-1,2]imidazo[5,4-c]rifamycin SV obtained in the Example 11.
Figure 36:
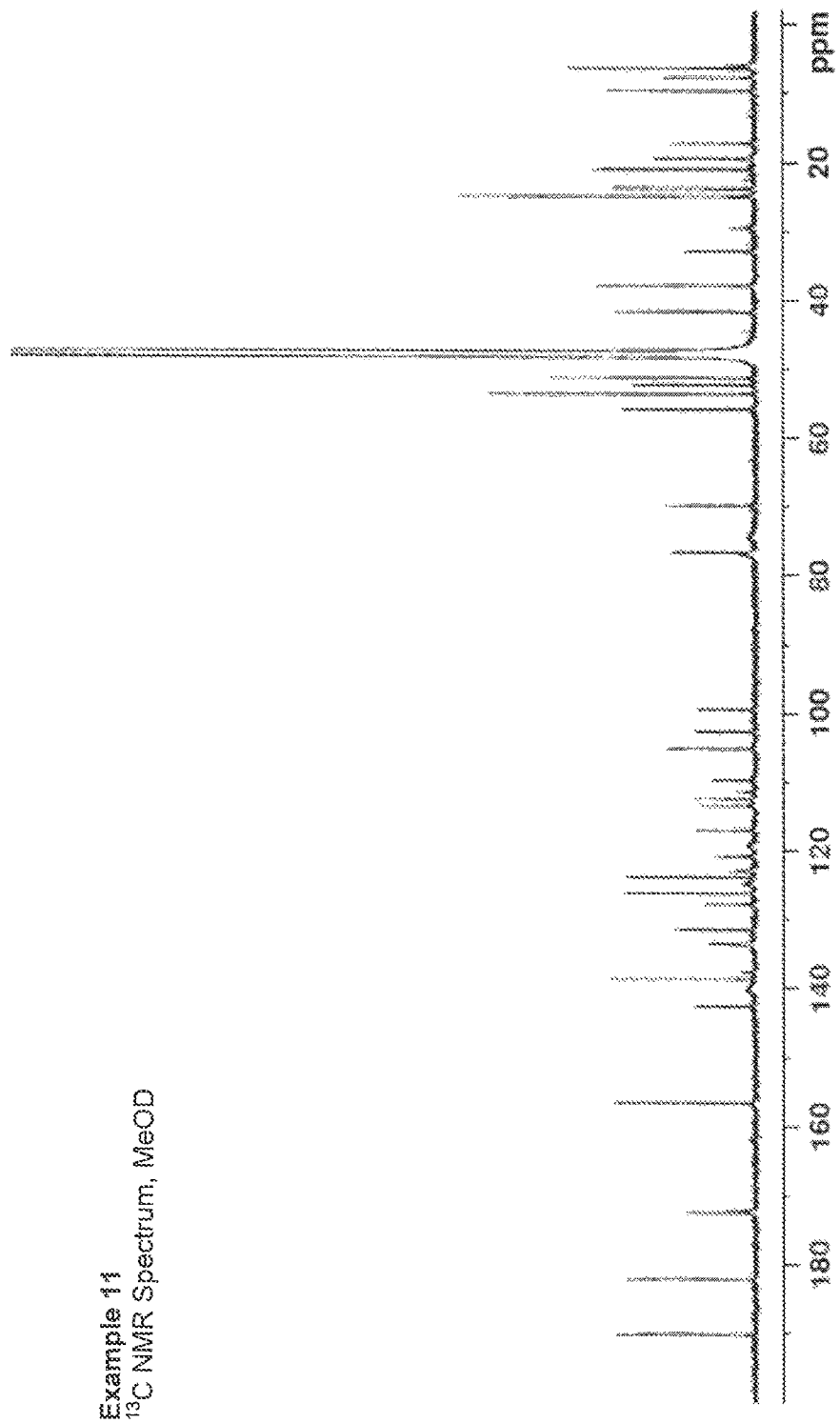
FIG. 36 shows the $^{13}$C NMR spectrum in MeOD of the compound 25-desacetyl-5'-[(1-piperidinyl)iminomethyl]-4-desoxypyrido[1',2'-1,2]imidazo[5,4-c]rifamycin SV obtained in the Example 11.
Figure 37:
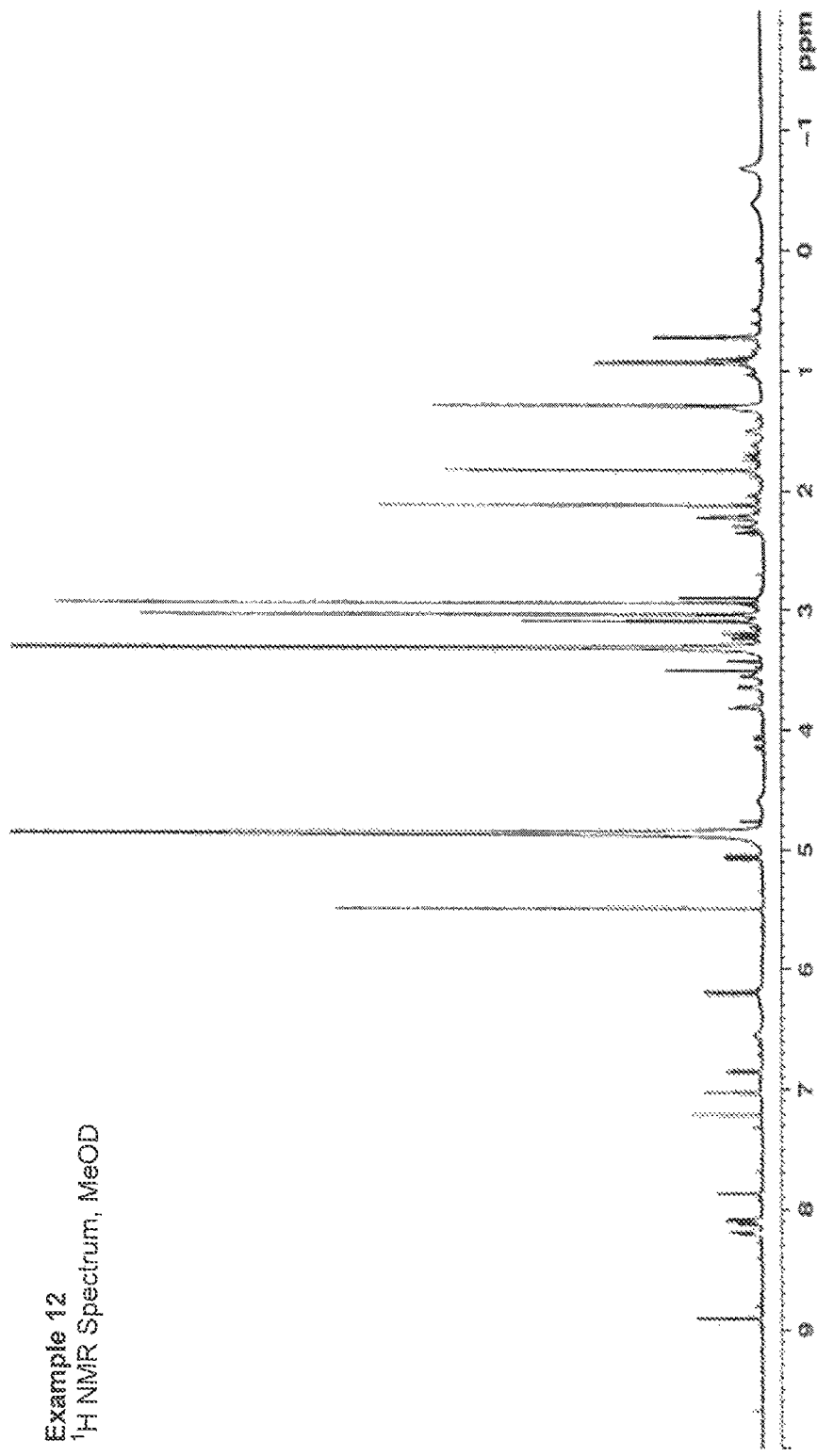
FIG. 37 shows the $^1$H NMR spectrum in MeOD of the compound 25-desacetyl-5'-[(N, N-dimethylamino)iminomethyl]-4-desoxypyrido[1',2'-1,2]imidazo[5,4-c]rifamycin SV obtained in the Example 12.
Figure 38:
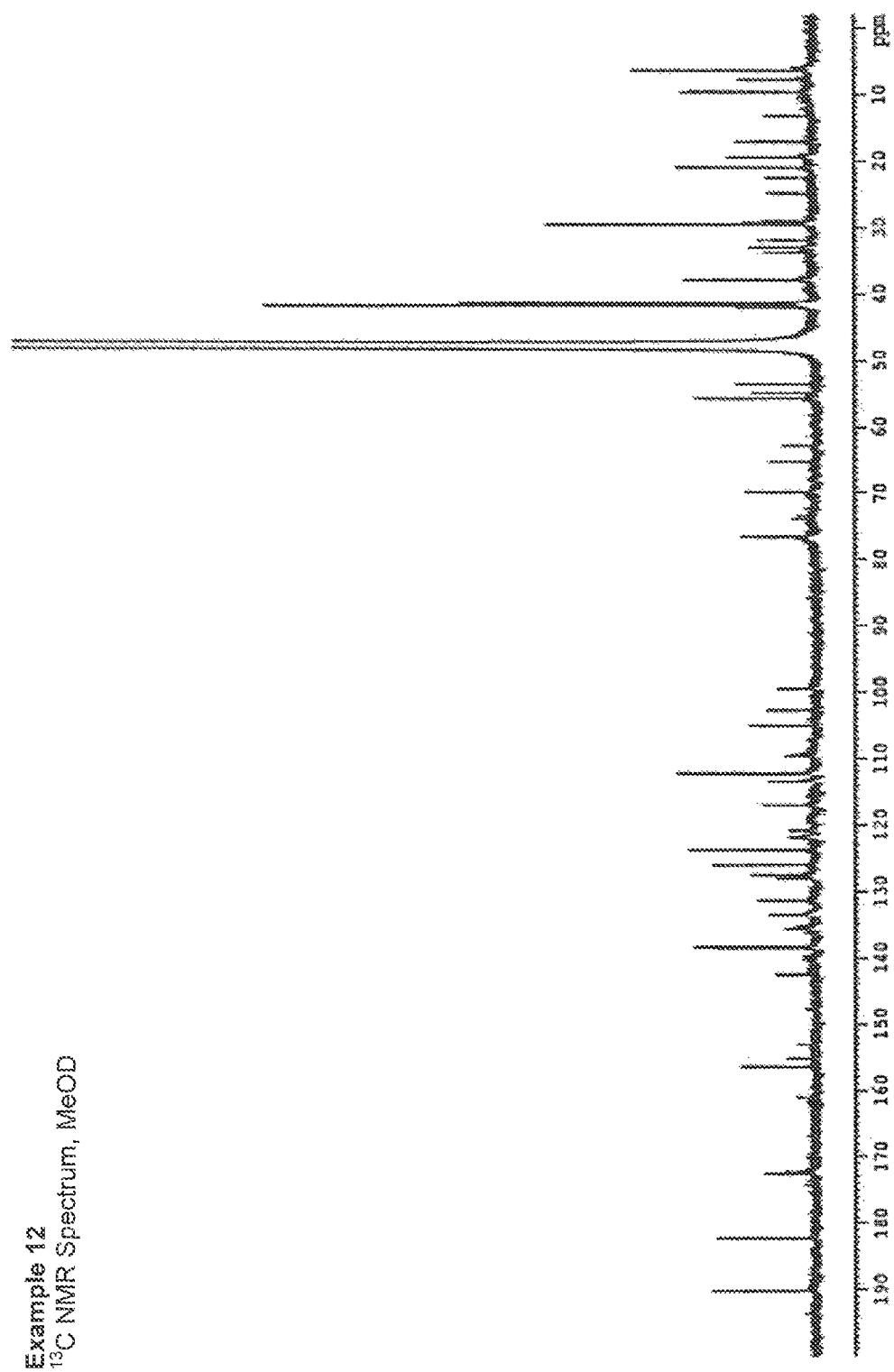
FIG. 38 shows the $^{13}$C NMR spectrum in MeOD of the compound 25-desacetyl-5'-[(N, N-dimethylamino)iminomethyl]-4-desoxypyrido[1',2'-1,2]imidazo[5,4-c]rifamycin SV obtained in the Example 12.
Figure 39:
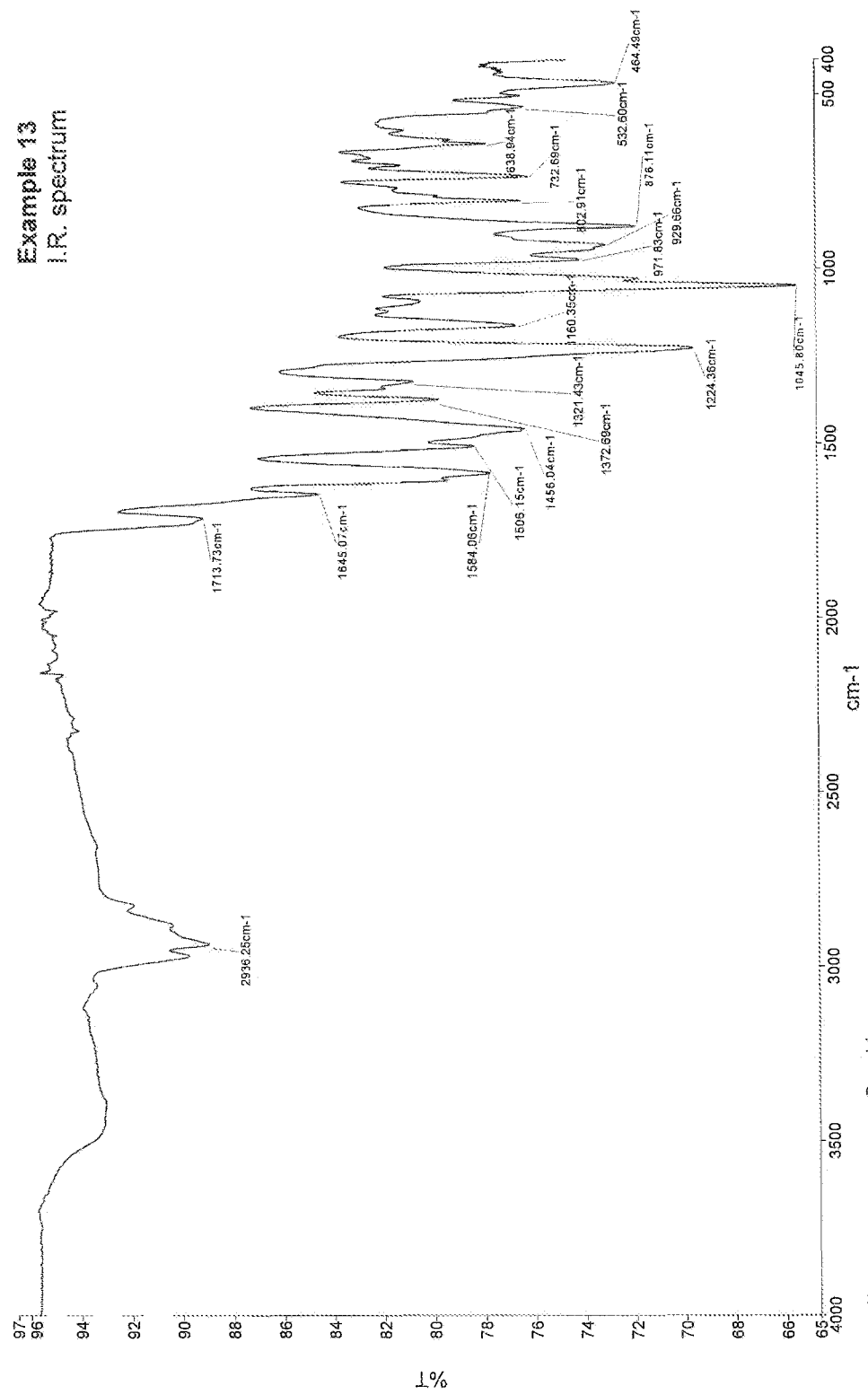
FIG. 39 shows the I.R. spectrum of the compound 4'-(N-methoxy)-iminomethyl-4-desoxypyrido[1',2'-1,2]imidazo[5,4-c]rifamycin SV obtained in the Example 13.
Figure 40:
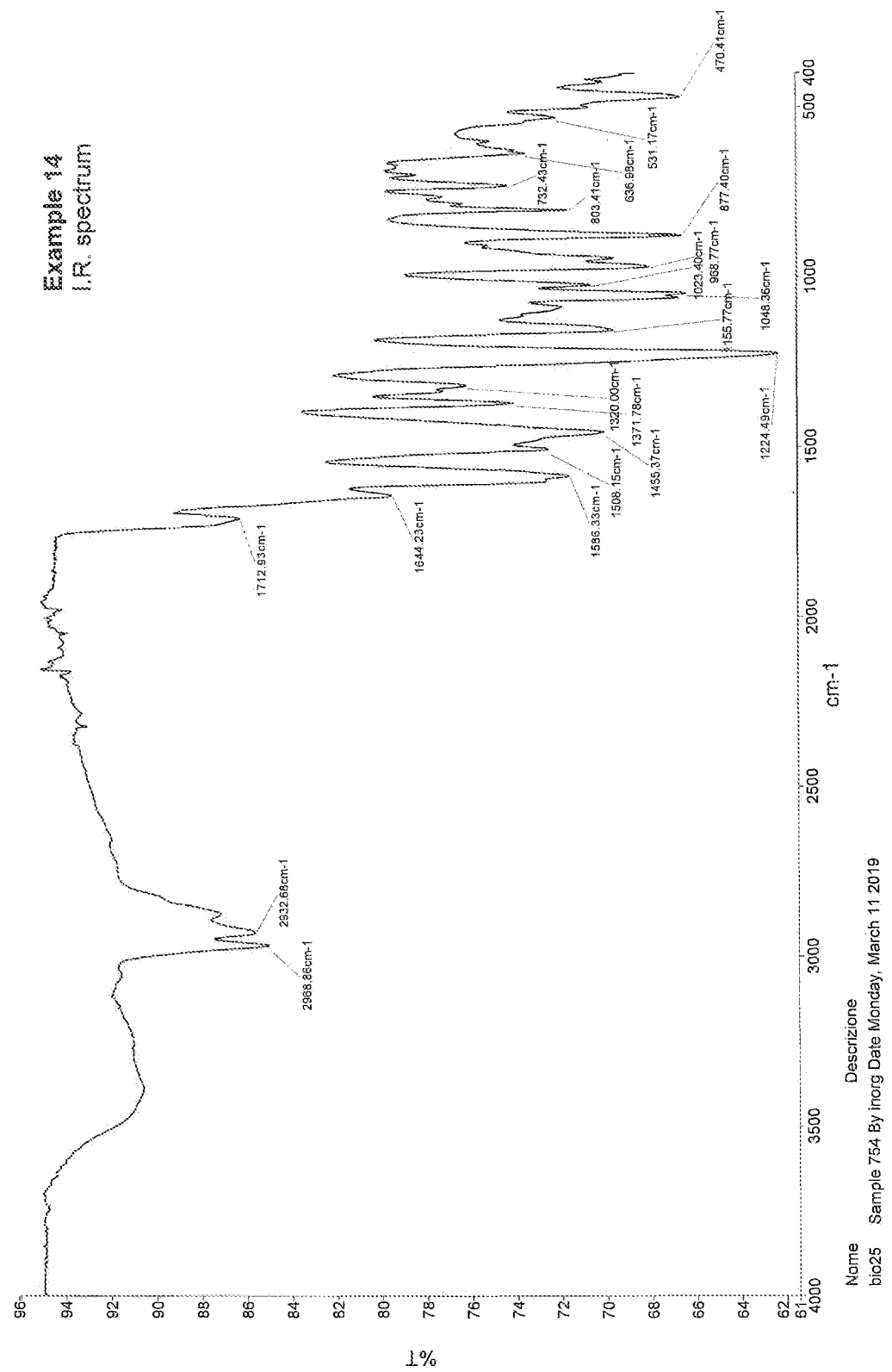
FIG. 40 shows the I.R. spectrum of the compound 4'-(N-isopropyl)-iminomethyl]-4-desoxypyrido[1',2'-1,2]imidazo[5,4-c]rifamycin SV obtained in the Example 14.
Figure 41:
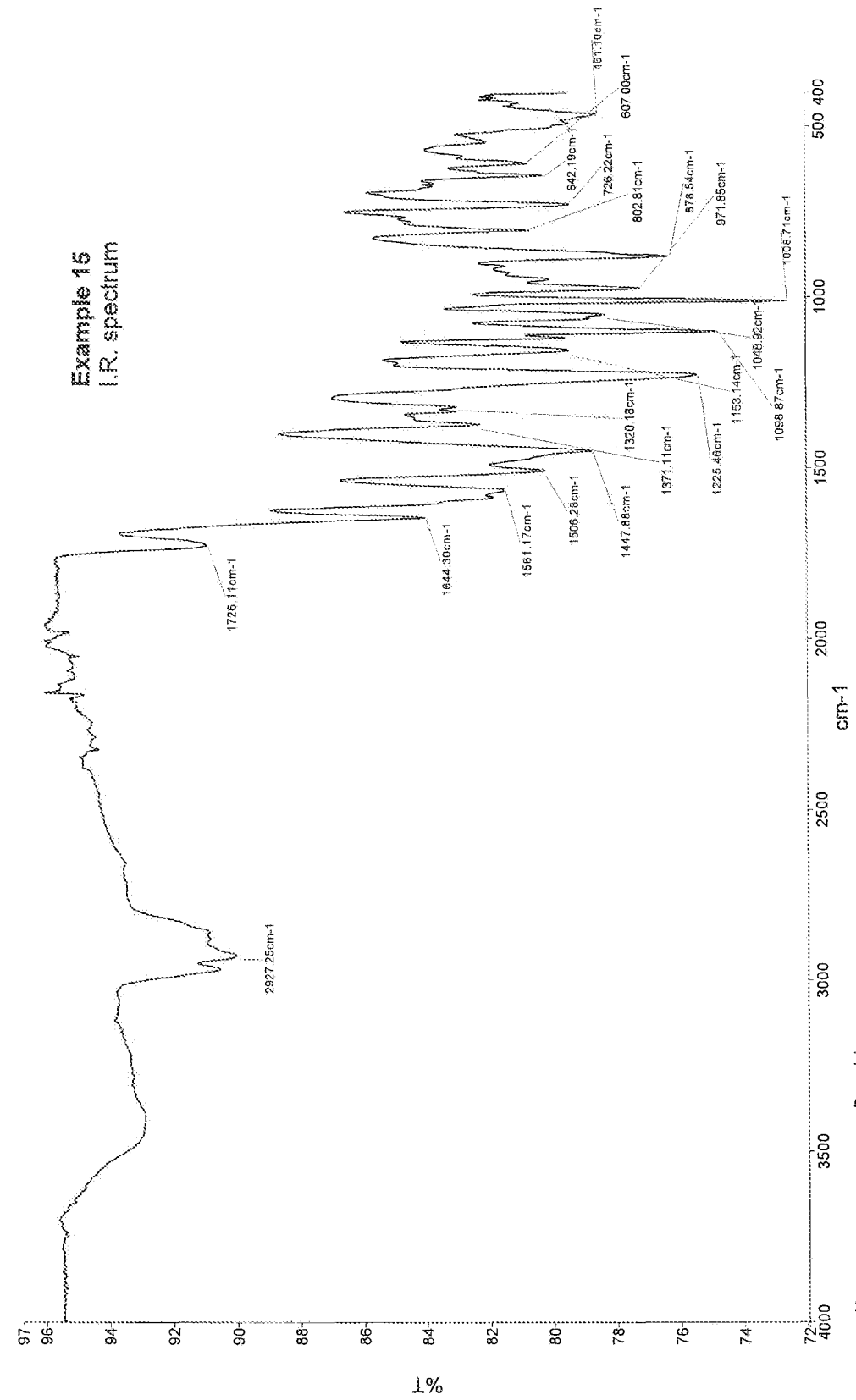
FIG. 41 shows the I.R. spectrum of the compound 4'-(4-morpholyl)-iminomethyl)-4-desoxypyrido[1',2'-1,2]imidazo[5,4-c]rifamycin SV obtained in the Example 15.

FIG. 3 represents the ratio between the number of bacterial cells, for each genus, at T5/T0, for each rat in the two groups. Tables 7-9 below show Ct values, cell counts per mg of stool obtained from the Ct values, respectively, and finally Table 9 shows the cell count average values for each bacteria genus, at T0 and T5, for each product.

TABLE 7

Average Ct for three qPCR analysis values

| | | | Ct Values | | | |
|---|---|---|---|---|---|---|
| Sample | Treatment | Time | Bifidobacterium | Eterococcus | Enterobacter | Lactobacillus |
| 1 | 3 | T0 | 14.687 | 22.913 | 25.862 | 18.459 |
| 2 | 3 | T0 | 14.914 | 24.536 | 23.335 | 18.559 |
| 3 | 3 | T0 | 15.525 | 22.221 | 28.170 | 16.317 |
| 4 | 3 | T0 | 15.586 | 23.426 | 23.199 | 18.290 |
| 5 | 3 | T0 | 15.517 | 21.939 | 23583 | 18.224 |
| 6 | 3 | T0 | 18.057 | 24.485 | 27.377 | 21.140 |
| 7 | RFX | T0 | 15.880 | 23.236 | 17.704 | 20.565 |
| 8 | RFX | T0 | 14.080 | 22.741 | 23.688 | 20.928 |
| 9 | RFX | T0 | 22.166 | 14.976 | 16.284 | 19.111 |
| 10 | RFX | T0 | 21.412 | 16.124 | 17.749 | 20.465 |
| 11 | RFX | T0 | 24.420 | 18.925 | 17.616 | 17.200 |
| 12 | RFX | T0 | 23.158 | 14.203 | 18.371 | 17.852 |
| 1 | 3 | T5 | 22.927 | 21.069 | 28.751 | 18.622 |
| 2 | 3 | T5 | 23.533 | 28.115 | 21.537 | 16.419 |
| 3 | 3 | T5 | 20.349 | 20.173 | 27.515 | 22.558 |
| 4 | 3 | T5 | 20.842 | 23.936 | 26.971 | 24.670 |
| 5 | 3 | T5 | 16.509 | 21.097 | 21.048 | 19.597 |
| 6 | 3 | T5 | 16.638 | 22.809 | 25.443 | 20.852 |
| 7 | RFX | T5 | 13.747 | 23.676 | 20.143 | 20.364 |
| 8 | RFX | T5 | 16.114 | 24.09 | 25.467 | 19.891 |
| 9 | RFX | T5 | 24.545 | 24.608 | 17.828 | 18.746 |
| 10 | RFX | T5 | 18.232 | 23.121 | 21.542 | 19.308 |
| 11 | RFX | T5 | 27.172 | 25.293 | 23.096 | 19.872 |
| 12 | RFX | T5 | 26.104 | 26.739 | 20.066 | 20.306 |

TABLE 8

Number of cells per mg of stool, derived from Ct values of Table 7

| | | | Cell Count | | | |
|---|---|---|---|---|---|---|
| Sample | Treatment | Time | Bifidobacterium | Eterococcus | Enterobacter | Lactobacillus |
| 1 | 3 | T0 | 2.08E+07 | 6.96E+04 | 9.02E+03 | 1.53E+06 |
| 2 | 3 | T0 | 1.78E+07 | 2.26E+04 | 5.20E+04 | 1.42E+06 |
| 3 | 3 | T0 | 1.17E+07 | 1.12E+05 | 1.82E+03 | 6.73E+06 |
| 4 | 3 | T0 | 1.12E+07 | 4.88E+04 | 5.71E+04 | 1.72E+06 |
| 5 | 3 | T0 | 1.17E+07 | 1.37E+05 | 4.37E+04 | 1.80E+06 |
| 6 | 3 | T0 | 2.02E+06 | 2.34E+04 | 3.15E+03 | 2.38E+05 |
| 7 | RFX | T0 | 9.11E+06 | 5.56E+04 | 2.57E+06 | 3.55E+05 |
| 8 | RFX | T0 | 3.17E+07 | 7.84E+04 | 4.07E+04 | 2.75E+05 |
| 9 | RFX | T0 | 1.17E+05 | 1.71E+07 | 6.89E+06 | 9.71E+05 |
| 10 | RFX | T0 | 1.97E+05 | 7.70E+06 | 2.50E+06 | 3.80E+05 |
| 11 | RFX | T0 | 2.45E+04 | 1.10E+06 | 2.74E+06 | 3.65E+06 |
| 12 | RFX | T0 | 5.87E+04 | 2.91E+07 | 1.62E+06 | 2.32E+06 |
| 1 | 3 | T5 | 6.90E+04 | 2.50E+05 | 1.22E+03 | 1.36E+06 |
| 2 | 3 | T5 | 4.53E+04 | 1.89E+03 | 1.81E+05 | 2.27E+06 |
| 3 | 3 | T5 | 4.12E+05 | 4.65E+05 | 2.87E+03 | 8.90E+04 |
| 4 | 3 | T5 | 2.92E+05 | 3.43E+04 | 4.18E+03 | 2.06E+04 |
| 5 | 3 | T5 | 5.89E+06 | 2.45E+05 | 2.54E+05 | 6.93E+05 |
| 6 | 3 | T5 | 5.39E+06 | 7.48E+04 | 1.21E+04 | 2.90E+05 |
| 7 | RFX | T5 | 4.00E+07 | 4.10E+04 | 4.75E+05 | 4.07E+05 |
| 8 | RFX | T5 | 7.75E+06 | 3.06E+04 | 1.19E+04 | 5.65E+05 |
| 9 | RFX | T5 | 2.25E+04 | .15E+04 | 2.36E+06 | 1.25E+06 |
| 10 | RFX | T5 | 1.79E+06 | 6.03E+04 | 1.80E+05 | 8.47E+05 |
| 11 | RFX | T5 | 3.64E+03 | 1.34E+04 | 6.13E+04 | 5.73E+05 |
| 12 | RFX | T5 | 7.62E+03 | 4.91E+03 | 5.01E+05 | 4.24E+05 |

TABLE 9

| Sample | Time | Bifidobacterium | Enterococcus | Enterobacter | Lactobacillus |
|---|---|---|---|---|---|
| 3 | T0 | $15.1 \times 10^6$ | $6.9 \times 10^4$ | $27.8 \times 10^3$ | $2.24 \times 10^6$ |
| | T5 | $2.02 \times 10^6$ | $17.8 \times 10^4$ | $44.3 \times 10^3$ | $1.45 \times 10^6$ |
| RFX | T0 | $6.87 \times 10^6$ | $9.2 \times 10^6$ | $2.69 \times 10^6$ | $1.3 \times 10^6$ |
| | T5 | $8.26 \times 10^6$ | $28 \times 10^4$ | $5.98 \times 10^5$ | $6.6 \times 10^5$ |

As it can be seen from FIG. 3 and from Tables 7-8-9, the oral treatment at 5 days, at a dose of 50 mg/kg, with product 3 induces a decrease of a factor of 10 in the bacterial count for the *Bifidobacterium* genus, while it does not induce significant changes in the cell counts of the other genera, i.e. *Enterococcus, Enterobacter*, and *Lactobacillus*. Conversely, treatment at 5 days at the same oral dose with Rifaximin induces a significant drop for the *Enterococcus* genus (about 100 times), a lower drop for the *Enterobacter* genus (about 10 times) while there are no significant differences for *Bifidobacterium* and *Lactobacillus*, although a decrease is detectable for both species. It is apparent that the product 3 shows a higher selectivity than Rifaximin towards the *Enterococcus, Enterobacter* and, to a lesser extent, towards *Lactobacillus* genera, while the selectivity towards *Bifidobacterium* is similar to that of Rifaximin.

Advantageously, due to its irrelevant absorption and its high selectivity in keeping intestinal eukaryotic bacterial flora virtually unchanged, the product 3 can be used in the therapy of all gastrointestinal diseases due to bacterial dismicrobism, especially in diseases requiring a chronic treatment.

The invention claimed is:

1. A compound of Formula (I) or pharmaceutically acceptable salts thereof

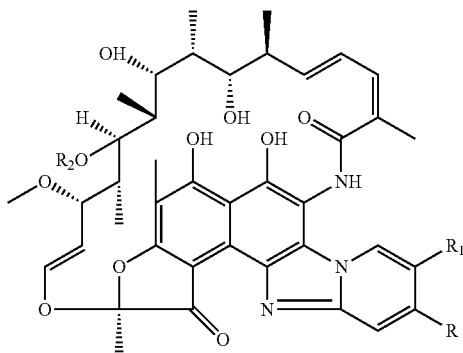

wherein
R and $R_1$ may be H,

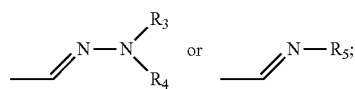

with the proviso that:
when

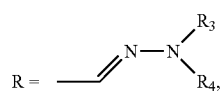

then $R_1$=H and $R_2$=CH$_3$CO— or H;
when

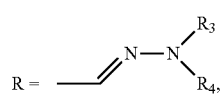

then R=H and $R_2$=CH$_3$CO— or H;
when

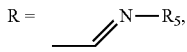

then $R_1$=H and $R_2$=CH$_3$CO— or H; and
when

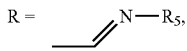

then R=H and $R_2$=CH$_3$CO— or H;
wherein $R_3$ and $R_4$ are the same or different and selected from the group comprising hydrogen, linear or branched $C_1$-$C_{10}$ alkyl, optionally substituted with one or more substituents selected from aminoalkyl, alkoxy, phenoxy, or sulfo, and aryl, optionally mono- or disubstituted with $C_1$-$C_4$ alkyl or alkoxy groups, halogen, amino, nitro; or
$R_3$ and $R_4$ taken together with two consecutive carbon atoms of the pyridine core may form a phenyl ring, optionally substituted with $C_1$-$C_4$ alkyl, or a 5- or 6-membered heterocyclic ring, optionally substituted with $C_1$-$C_4$ alkyl,
$R_5$ is selected from the group comprising hydrogen, hydroxy, linear or branched $C_1$-$C_{10}$ alkyl, optionally substituted with one or more substituents selected from aminoalkyl, alkoxy, phenoxy, or sulfo, and aryl optionally mono- or disubstituted with $C_1$-$C_4$ alkyl or alkoxy groups, halogen, amino, nitro.

2. A compound according to claim 1, wherein the aryl, optionally mono- or disubstituted with $C_1$-$C_4$ alkyl or alkoxy groups, halogen, amino, nitro, is selected from phenyl and benzyl.

3. A compound according to claim 1, wherein when $R_3$ and $R_4$ are taken together with two consecutive carbon atoms of the pyridine core to form a 5- or 6-membered heterocyclic ring, optionally substituted with $C_1$-$C_4$ alkyl, said 5- or 6-membered heterocyclic ring is selected from the group comprising pyrrolidine, piperidine, piperazine, and morpholine.

4. A compound according to claim 1, selected from the group consisting of:
4'-[(4-methyl-1-piperazinyl)iminomethyl]-4-desoxypyrido[1',2'-1,2]imidazo[5,4-c]rifamycin SV;
4'-[(1-piperidinyl)iminomethyl]-4-desoxypyrido[1',2'-1,2]imidazo[5,4-c]rifamycin SV;
4'-[(N,N-dimethylamino)iminomethyl]-4-desoxypyrido[1',2'-1,2]imidazo[5,4-c]rifamycin SV;
4'-[(4-carboxyamidopyridyl)iminomethyl]-4-desoxypyrido[1',2'-1,2]imidazo[5,4-c]rifamycin SV;
5'-[(N,N-dimethylamino)iminomethyl]-4-desoxypyrido[1',2'-1,2]imidazo[5,4-c]rifamycin SV;
5'-[(1-piperidinyl)iminomethyl]-4-desoxypyrido[1',2'-1,2]imidazo[5,4-c]rifamycin SV;
5'-[(N,N-dimethylamino)iminomethyl]-4-desoxypyrido[1',2'-1,2]imidazo[5,4-c]rifamycin SV;
4'-[(4-methyl-1-piperazinyl)iminomethyl]-4-desoxypyrido[1',2'-1,2]imidazo[5,4-c]rifamycin S;
25-desacetyl-5'-[(1-piperidinyl)iminomethyl]-4-desoxypyrido[1',2'-1,2]imidazo[5,4-c]rifamycin SV;
25-desacetyl-5'-[(N,N-dimethylamino)iminomethyl]-4-desoxypyrido[1',2'-1,2]imidazo[5,4-c]rifamycin SV;

4'-[(N-morpholinyl)iminomethyl]-4-desoxypyrido[1',2'-1,2]imidazo[5,4-c]rifamycin SV;
5'-[(N-morpholinyl)iminomethyl]-4-desoxypyrido[1',2'-1,2]imidazo[5,4-c]rifamycin SV;
25-desacetyl-4'-[(N-morpholinyl)iminomethyl]-4-desoxypyrido[1',2'-1,2]imidazo[5,4-c]rifamycin SV;
25-desacetyl-5'-[(N-morpholinyl)iminomethyl]-4-desoxypyrido[1',2'-1,2]imidazo[5,4-c]rifamycin SV;
4'-[(N-propyl,N-butyl)iminomethyl]-4-desoxypyrido[1',2'-1,2]imidazo[5,4-c]rifamycin SV;
5'-[(N-propyl,N-butyl)iminomethyl]-4-desoxypyrido[1',2'-1,2]imidazo[5,4-c]rifamycin SV;
25-desacetyl-4'-[(N-propyl,N-butyl)iminomethyl]-4-desoxypyrido[1',2'-1,2]imidazo[5,4-c]rifamycin SV;
25-desacetyl-5'-[(N-propyl,N-butyl)iminomethyl]-4-desoxypyrido[1',2'-1,2]imidazo[5,4-c]rifamycin SV;
4'-[(N,N-dipentyl)iminomethyl]-4-desoxypyrido[1',2'-1,2]imidazo[5,4-c]rifamycin SV;
5'-[(N,N-dipentyl)iminomethyl]-4-desoxypyrido[1',2'-1,2]imidazo[5,4-c]rifamycin SV;
25-desacetyl-4'-[(N,N-dipentyl)iminomethyl]-4-desoxypyrido[1',2'-1,2]imidazo[5,4-c]rifamycin SV;
25-desacetyl-5'-[(N,N-dipentyl)iminomethyl]-4-desoxypyrido[1',2'-1,2]imidazo[5,4-c]rifamycin SV;
4'-[(4-ethyl-1-piperazinyl)iminomethyl]-4-desoxypyrido[1',2'-1,2]imidazo[5,4-c]rifamycin SV;
5'-[(4-ethyl-1-piperazinyl)iminomethyl]-4-desoxypyrido[1',2'-1,2]imidazo[5,4-c]rifamycin SV;
25-desacetyl-4'-[(4-ethyl-1-piperazinyl)iminomethyl]-4-desoxypyrido[1',2'-1,2]imidazo[5,4-c]rifamycin SV;
25-desacetyl-5'-[(4-ethyl-1-piperazinyl)iminomethyl]-4-desoxypyrido[1',2'-1,2]imidazo[5,4-c]rifamycin SV;
4'-[(4-propyl-1-piperazinyl)iminomethyl]-4-desoxypyrido[1',2'-1,2]imidazo[5,4-c]rifamycin SV;
5'-[(4-propyl-1-piperazinyl)iminomethyl]-4-desoxypyrido[1',2'-1,2]imidazo[5,4-c]rifamycin SV;
25-desacetyl-4'-[(4-propyl-1-piperazinyl)iminomethyl]-4-desoxypyrido[1',2'-1,2]imidazo[5,4-c]rifamycin SV; and
25-desacetyl-5'-[(4-propyl-1-piperazinyl)iminomethyl]-4-desoxypyrido[1',2'-1,2]imidazo[5,4-c]rifamycin SV;
or pharmaceutically acceptable salts thereof.

5. A compound selected from the group consisting of 4'-[(alkyloxy-iminomethyl]-4-desoxypyrido[1',2'-1,2]imidazo[5,4-c]rifamycin and 4'-[N-alkyliminomethyl]-4-desoxypyrido[1',2'-1,2]imidazo[5,4-c]rifamycin SV.

6. A compound according to claim 5, selected from the group consisting of 4'-(N-methoxy)-iminomethyl-4-desoxypyrido[1',2'-1,2]imidazo[5,4-c]rifamycin SV and 4'-(N-isopropyl)-iminomethyl]-4-desoxypyrido[1',2'-1,2]imidazo[5,4-c]rifamycin SV.

7. The compound: 4'-hydroxymethyl-4-desoxypyrido[1',2'-1,2]imidazo[5,4-c]rifamycin S or SV, or pharmaceutically acceptable salts thereof.

8. The compound: 4'-formyl-4-desoxypyrido[1',2'-1,2]imidazo[5,4-c]rifamycin S or SV, e or pharmaceutically acceptable salts thereof.

9. A compound according to claim 1, for use as a medicament.

10. A compound according to claim 9, for use in the treatment of a gastrointestinal tract disease or in a skin, eye, vaginal or dental infection.

11. A compound according to claim 9, for use in the treatment dry mastitis, in vaginal diseases in cows, in intestinal diseases in pets, or as auxinic therapy in animal husbandry.

12. The compound according to claim 10, wherein the gastrointestinal tract disease is selected from the group consisting of diseases due to dismicrobism, IBD, Crohn's disease, diverticulosis, and traveler's diarrhea.

13. The compound according to claim 10, wherein the skin, eye, vaginal or dental infection is an infection requiring a chronic treatment.

14. The compound according to claim 11, wherein the animal husbandry is husbandry of chickens, turkeys, ducks, or rabbits.

15. A pharmaceutical composition comprising at least one compound of Formula (I) according to claim 1, together with at least one pharmaceutically acceptable excipient.

16. A pharmaceutical composition according to claim 15, suitable to be administered topically.

17. The pharmaceutical composition according to claim 16, wherein the composition is suitable to be administered in the form of a solid, liquid or gel.

18. A process for producing a compound of Formula (I) according to claim 1 when R and $R_1$ may be H, or $$\diagup\!\!=\!\!N-N\diagup^{R_3}_{R_4},$$

comprising the steps of:
reacting Rifamycin O with 2-amino-4-hydroxymethylpyridine to obtain 4'-hydroxymethyl-4-desoxypyrido[1',2'-1,2]imidazo[5,4-c]rifamycin S or SV;
oxidizing in liquid phase 4'-hydroxymethyl-4-desoxypyrido[1',2'-1,2]imidazo[5,4-c]rifamycin S or SV with a suitable oxidant to obtain 4'-formyl-4-desoxypyrido[1',2'-1,2]imidazo[5,4-c]rifamycin S or SV; and
reacting 4'-formyl-4-desoxypyrido[1',2'-1,2]imidazo[5,4-c]rifamycin S or SV with a hydrazine of Formula (II) $NH_2-N(R_3)(R_4)$, wherein $R_3$ and $R_4$ are as defined in Formula (I), to obtain the corresponding hydrazone.

19. The process according to claim 18, wherein from about 1 to about 6 molar equivalents of 2-amino-4-hydroxymethylpyridine are used per mole of Rifamycin O and/or from about 1 to about 6 molar equivalents of hydrazine are used per mole of 4'-formyl-4-desoxypyrido[1',2'-1,2]imidazo[5,4-c]rifamycin S or SV.

20. The process according to claim 18, wherein the solvent used is an organic solvent selected from an aliphatic alkanol containing 1 to 4 carbon atoms, alone or in a mixture with water, or with DMF, or in a short-chain halogenated solvent.

21. The process according to claim 18, wherein the reaction temperature may vary from the temperature of 10° C. to the solvent boiling point and/or the reaction time may vary from a few minutes to 24 h.

22. The process according to claim 18, wherein the obtained compound of Formula (I) is oxidized by treatment with a suitable oxidant.

23. The process according to claim 18,
wherein the step of oxidizing in liquid phase is in an aprotic solvent, and
wherein the oxidant is manganese dioxide.

24. The process according to claim 20, wherein the short-chain halogenated solvent is dichloromethane.

25. The process according to claim 21, wherein the reaction temperature may vary from the temperature of 10° C. to a temperature not above 80° C. and/or the reaction time may vary from a few minutes to 24 h.

26. The process according to claim 22, wherein the oxidant is manganese dioxide.

27. A process for producing a compound of Formula (I) according to claim 1 when R and $R_1$ may be H,
or comprising the steps of:

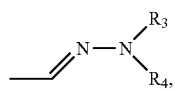

comprising the steps of:
reacting a hydrazine of Formula (II) $NH_2$—$N(R_3)(R_4)$, wherein $R_3$ and $R_4$ are as defined in Formula (I), with 2-amino-4-formylpyridine or with 2-amino-5-formylpyridine to obtain the corresponding hydrazone; and
reacting the obtained hydrazone with Rifamycin O, 3-iodorifamycin S, 3-bromorifamycin S, or 25-desacetyl-25-hydroxyrifamycin S.

28. The process according to claim 27, wherein from about 1 to about 6 moles of the obtained hydrazone are used per mole of Rifamycin O or 3-iodo/bromo rifamycin S.

* * * * *